US009782437B2

(12) United States Patent
Holmes et al.

(10) Patent No.: US 9,782,437 B2
(45) Date of Patent: Oct. 10, 2017

(54) METHODS AND COMPOSITIONS FOR TARGETED CLEAVAGE AND RECOMBINATION

(71) Applicant: Sangamo BioSciences, Inc., Richmond, CA (US)

(72) Inventors: Michael C. Holmes, Richmond, CA (US); Fyodor Urnov, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

(21) Appl. No.: 14/448,618

(22) Filed: Jul. 31, 2014

(65) Prior Publication Data

US 2014/0369980 A1    Dec. 18, 2014

Related U.S. Application Data

(63) Continuation of application No. 13/837,027, filed on Mar. 15, 2013, now Pat. No. 9,289,451, which is a continuation of application No. 12/804,234, filed on Jul. 16, 2010, now Pat. No. 8,524,500, which is a continuation of application No. 10/912,932, filed on Aug. 6, 2004, now Pat. No. 7,888,121.

(60) Provisional application No. 60/493,931, filed on Aug. 8, 2003, provisional application No. 60/518,253, filed on Nov. 7, 2003, provisional application No. 60/530,541, filed on Dec. 18, 2003, provisional application No. 60/542,780, filed on Feb. 5, 2004, provisional application No. 60/556,831, filed on Mar. 26, 2004, provisional application No. 60/575,919, filed on Jun. 1, 2004.

(51) Int. Cl.
| | |
|---|---|
| *A61K 35/12* | (2015.01) |
| *C12N 15/62* | (2006.01) |
| *C12N 15/85* | (2006.01) |
| *C07K 14/715* | (2006.01) |
| *C12N 9/14* | (2006.01) |
| *C07K 14/47* | (2006.01) |
| *C12N 9/22* | (2006.01) |
| *C07K 14/435* | (2006.01) |

(52) U.S. Cl.
CPC ........ *A61K 35/12* (2013.01); *C07K 14/43595* (2013.01); *C07K 14/4717* (2013.01); *C07K 14/715* (2013.01); *C12N 9/14* (2013.01); *C12N 9/22* (2013.01); *C12N 15/62* (2013.01); *C12N 15/85* (2013.01); *C07K 2319/00* (2013.01); *C07K 2319/09* (2013.01); *C07K 2319/81* (2013.01); *C12N 2800/80* (2013.01)

(58) Field of Classification Search
CPC ............. A61K 2035/122; A61K 35/12; C12N 15/907; C12N 9/22; C07K 2319/80; C07K 2319/81
See application file for complete search history.

(56) References Cited

U.S. PATENT DOCUMENTS

| | | | |
|---|---|---|---|
| 4,665,184 A | | 5/1987 | Dervan et al. |
| 4,795,184 A | | 1/1989 | Dervan et al. |
| 4,942,227 A | | 7/1990 | Dervan et al. |
| 5,176,996 A | * | 1/1993 | Hogan .................. C07H 21/00 435/6.12 |
| 5,356,802 A | | 10/1994 | Chandrasegaran |
| 5,416,260 A | * | 5/1995 | Koller et al. ................... 800/11 |
| 5,422,251 A | * | 6/1995 | Fresco ................ C12N 15/113 435/6.12 |
| 5,436,150 A | | 7/1995 | Chandrasegaran |
| 5,464,764 A | | 11/1995 | Capecchi et al. |
| 5,487,994 A | | 1/1996 | Chandrasegaran |
| 5,714,352 A | | 2/1998 | Jakobovits |
| 5,789,155 A | | 8/1998 | Dervan et al. |
| 5,789,538 A | | 8/1998 | Rebar et al. |
| 5,792,640 A | | 8/1998 | Chandrasegaran |
| 5,916,794 A | | 6/1999 | Chandrasegaran |
| 5,945,577 A | | 8/1999 | Stice et al. |

(Continued)

FOREIGN PATENT DOCUMENTS

| | | |
|---|---|---|
| EP | 0419621 B1 | 4/1991 |
| EP | 0 957 165 | 11/1999 |

(Continued)

OTHER PUBLICATIONS

Elsner et al. Non-expression of HLA-B*5111N is caused by an insertion into the cytosine island at exon 4 creating a frameshift stop codon. Tissue Antigens, vol. 57, pp. 369-372, 2001.*
Winters et al. Gene targeted agents: New opportunities for rational drug development. Current Opinion in Molecular Therapeutics, vol. 2, No. 6, pp. 670-681, 2000.*
Aggarwal, et al., "Novel Site-Specific DNA Endonucleases," *Current Opinion in Structural Biology* 8:19-25 (1998).
Abremski, et al., "Bacteroiphage P1 Site Specific Recombination," *J. Biol. Chem.* 259:1509-1514 (1984).

(Continued)

*Primary Examiner* — Jennifer Dunston
(74) *Attorney, Agent, or Firm* — Pasternak Patent Law; Susan Abrahamson

(57) ABSTRACT

Disclosed herein are methods and compositions for targeted cleavage of a genomic sequence, targeted alteration of a genomic sequence, and targeted recombination between a genomic region and an exogenous polynucleotide homologous to the genomic region. The compositions include fusion proteins comprising a cleavage domain (or cleavage half-domain) and an engineered zinc finger domain and polynucleotides encoding same. Methods for targeted cleavage include introduction of such fusion proteins, or polynucleotides encoding same, into a cell. Methods for targeted recombination additionally include introduction of an exogenous polynucleotide homologous to a genomic region into cells comprising the disclosed fusion proteins.

8 Claims, 42 Drawing Sheets

(56) References Cited

U.S. PATENT DOCUMENTS

| | | | |
|---|---|---|---|
| 5,955,341 | A | 9/1999 | Kang et al. |
| 6,007,988 | A | 12/1999 | Choo et al. |
| 6,013,453 | A | 1/2000 | Choo et al. |
| 6,077,710 | A | 6/2000 | Susko-Parrish et al. |
| 6,140,081 | A | 10/2000 | Barbas |
| 6,140,466 | A | 10/2000 | Barbas et al. |
| 6,147,276 | A | 11/2000 | Campbell et al. |
| 6,242,568 | B1 | 6/2001 | Barbas et al. |
| 6,265,196 | B1 | 7/2001 | Chandrasegaran |
| 6,326,166 | B1 | 12/2001 | Pomerantz et al. |
| 6,331,658 | B1 | 12/2001 | Cooper et al. |
| 6,395,523 | B1 | 5/2002 | Kong et al. |
| 6,453,242 | B1 | 9/2002 | Eisenberg et al. |
| 6,479,626 | B1 | 11/2002 | Kim et al. |
| 6,534,261 | B1 | 3/2003 | Cox, III et al. |
| 6,576,443 | B2 | 6/2003 | Hennecke et al. |
| 6,750,378 | B2 | 6/2004 | Derose et al. |
| 2002/0022021 | A1 | 2/2002 | Emerson |
| 2002/0107214 | A1 | 8/2002 | Choulika et al. |
| 2002/0110898 | A1 | 8/2002 | Choulika et al. |
| 2002/0152488 | A1 | 10/2002 | Cooper et al. |
| 2003/0131365 | A1 | 7/2003 | Cooper et al. |
| 2003/0232410 | A1 | 12/2003 | Liljedahl et al. |
| 2004/0019002 | A1 | 1/2004 | Choulika et al. |
| 2004/0121357 | A1 | 6/2004 | Franklin |
| 2004/0203153 | A1 | 10/2004 | Le Mouellic et al. |
| 2005/0208489 | A1 | 9/2005 | Carroll et al. |
| 2006/0242726 | A1 | 10/2006 | Collodi et al. |

FOREIGN PATENT DOCUMENTS

| | | |
|---|---|---|
| EP | 1007714 B1 | 12/2005 |
| WO | WO 90/05180 | 5/1990 |
| WO | WO 91/06666 | 5/1991 |
| WO | WO 93/21320 | 10/1993 |
| WO | WO 93/25567 | 12/1993 |
| WO | WO 95/09233 | 4/1995 |
| WO | 95/17911 A1 | 7/1995 |
| WO | WO 95/31560 | 11/1995 |
| WO | WO 96/40882 | 12/1996 |
| WO | WO 97/47758 | 12/1997 |
| WO | WO 98/53058 | 11/1998 |
| WO | WO 98/53059 | 11/1998 |
| WO | WO 98/53060 | 11/1998 |
| WO | WO 99/05267 | 2/1999 |
| WO | WO 99/15650 | 4/1999 |
| WO | WO 99/31260 | 6/1999 |
| WO | WO 00/09755 | 2/2000 |
| WO | WO 00/28008 | 5/2000 |
| WO | WO 00/42219 | 7/2000 |
| WO | WO 00/46385 | 8/2000 |
| WO | WO 00/46386 | 8/2000 |
| WO | WO 00/63365 | 10/2000 |
| WO | WO 01/05961 | 1/2001 |
| WO | WO 01/19981 | 3/2001 |
| WO | WO 01/40798 | 6/2001 |
| WO | WO 01/66717 | 9/2001 |
| WO | WO 02/04488 | 1/2002 |
| WO | WO 03027247 A2 * | 4/2003 |
| WO | WO 03/080809 | 10/2003 |
| WO | WO 03/087341 | 10/2003 |
| WO | WO 2004/037977 | 5/2004 |
| WO | WO 2007/035962 | 3/2007 |
| WO | WO 2007/115886 | 10/2007 |

OTHER PUBLICATIONS

Akopian, et al., "Chimeric Recombinases with Designed DNA Sequence Recopition," *Proc. Natl. Acad. Sci. USA* 100:8688-8691 (2003).
Baubonis, et al., "Genomic Targeting with Purified Cre Recombinase," *Nucleic Acids Res.* 21:2025-2029 (1993).
Beerli, et al., "Engineering Polydactyl Zinc-Finger Transcription Factors," *Nature Biotechnology* 20:135-141 (2000).
Bibikova, et al., "Stimulation of Homologous Recombination through Targeted Cleavage by Chimeric Nucleases," *Molecular and Cellular Biology* 21(1):289-297 (2001).
Bibikova, et al., "Targeted Chromosomal Cleavage and Mutagenesis in *Drosophila* Using Zinc-Finger Nucleases," *Genetics* 161:1169-1175 (2002).
Bibikova, et al., "Enhancing Gene Targeting with Designed Zinc Finger Nucleases," *Science* 300:764 (2003) Including Supporting Online Materials.
Bitiniate, et al., "Fold Dimerization is Required for DNA Cleavage," *Proc. Natl. Acad. Sci.* 95:10570-10575 (1998).
Brenneman, et al., "Stimulation of Intrachromosomal Homologous Recombination in Human Cells by Electroporation with Site Specific Endonucleases," *Proc. Natl. Acad. Sci.* 93:3608-3612 (1996).
Brisson, et al., "Expression of a Bacterial Gene in Plants by Using a Viral Vector," *Nature* 310:511-514 (1984).
Broglie, et al., "Light Regulated Expression of a Pea Ribulose-1, 5-Biphosphate Carboxylase Small Subunit Gene in Transformed Plant Cells," *Science* 224:838-843 (1984).
Campbell, et al., "Sheep Cloned by Nuclear Transfer from a Cultured Cell Line," *Nature* 380:64-66 (1996).
Cappechi, et al., "Altering the Genome by Homologous Recombination," *Science* 244:1288-1292 (1989).
Chandrasegaran, et al., "Chimeric Restriction Enzymes: What is Next?" *Biol Chem.* 380:841-848 (1999).
Chevalier, et al., "Design, Activity, and Structure of a Highly Specific Artificial Endonuclease," *Molecular Cell* 10:895-905 (2002).
Choulika, et al., "Induction of Homologous Recombination in Mammalian Chromosomes by using the I-SceI System of *Saccharomyces cerevisiae*," *Molecular and Cellular Biology* 15 (4):1968-1973 (1995).
Cohen-Tannoudji, et al., "I-SceI-Induced Gene Replacement at a Natural Locus in Embryonic Stem Cells," *Molecular and Cellular Biology* 18(3):1444-1448 (1998).
Corruzzi, et al., "Tissue Specific and Light-Regulated Expression of a Pea Nuclear Gene Encoding the Small Subunit of Ribulose-1, 5-Biphosphate Carboxylase," *Embo. J.* 3:1671-1679 (1984).
Desjarlais, et al., "Use of a Zinc-Finger Consensus Sequence Framework and Specificity Rules to Design Specific DNA Binding Proteins," *Proc. Natl. Acad. Sci. USA* 90:2256-2260 (1993).
Desjarlais, et al., "Towards Rules Relating Zinc Finger Protein Sequences and DNA Binding Site Preferences," *Proc. Natl. Acad. Sci. USA* 89:7345-7349 (1992).
Donoho, et al., "Analysis of Gene targeting and Intrachromosomal Homologous Recombination Stimulated by Genomic Double-Strand Breaks in Mouse Embryonic Stem Cells," *Molecular and Cellular Biology* 18(7):4070-4078 (1998).
Dreier, et al., "Development of Zinc Finger Domains for Recognition of the 5'-Ann-3' Family of DNA Sequences and Their Use in the Construction of Artificial Transcription Factors," *J. Biol. Chem.* 276(31):29466-29478 (2001).
Edelstein, et al., "Gene therapy clinical trials worldwide 1989-2004—an overview," *J. Gene Med*, 6:597-602 (2004).
Elliot, et al., "Gene Conversion Tracts from Double Strand Break Repair in Manunalian Cells," *Molecular and Cellular Biology* 18(1):93-101 (1998).
Elrod-Erickson, et al., "Binding Studies with Mutants of Zif268," *J. Biol. Chem.* 274(27):19281-19285 (1999).
Evans, et al., Establishment in Culture of Pluripotential Cells from Mouse Embryos, *Nature* 292:154-156 (1981).
Fujioka, et al., "Targeted Recombination with Single-Stranded DNA Vectors in Mammalian Cells," *Nucleic Acids Research* 21:407-412 (1993).
Furguson-Smith, "Imprinting and the Epigenetic Asymmetry Between Parental Genomes," *Science* 293:1086-1089 (2001).
GenBank Accession No. J01749, GI:208958, publicly available Jun. 2002, printed as pp. 1/7-7/7.
Gorlich, et al., "Nucleocytoplasmic Transport." *Science* 271:1513-1518 (1996).

(56) References Cited

OTHER PUBLICATIONS

Gowda, et al., "Identification of Promoter Sequences for the Major RNA Transcripts of Figwort Mosaic and Peanut Chloritic Streak Virus (Caulimovirus Group)," *J. Cell. Biochem.* 13D:301 (1989).
Greisman, et al., "A General Strategy for Selecting High-Affinity Zinc Finger Proteins for Diverse DNA Target Sites," *Science* 275:657-661 (1997).
Gu, et al., "Independent Control of Immunoglobulin Switch Recombination at Individual Switch Regions Evidenced through Cre-IoxP-Mediated Gene Targeting," *Cell* 73:1155-1164 (1993).
Gu, et al., "Deletion of a DNA Polymerase B Gene Segment in T Cells Using Cell Type-Specific Gene Targeting," *Science* 265:103-106 (1994).
Gurley, et al., "Upstream Sequences Required for Efficient Expression of a Soybean Heat Shock Gene," *Mol. Cell. Biol.* 6:559-565 (1986).
Hanson, et al., "Analysis of Biological Selections for High-Efficiency Gene Targeting," *Mol. Cell. Biol.* 15:45-51 (1995).
Hicks, et al., "Three Classes of Nuclear Import Signals Bind to Plant Nuclei," *Plant Physiol.* 107:1055-1058 (1995).
High, et al., "Gene Therapy: The Moving Finger," *Nature* 435:577-579 (2005).
Huang, et al., "Splase: A New Class IIS Zinc-Finger Restriction Endonuclease with Specificity for Sp1 Binding Sites," *Journal of Protein Chemistry* 15(5):481-489 (1996).
Jallepalli, et al., "Securin is Required for Chromosomal Stability in Human Cells," Cell 105:445-457 (2001).
Jaenisch, "Transgenic Animals," *Science* 240:1468-1474 (1988).
Jasin, "Genetic Manipulation of Genomes with Rare-Cutting Endonucleases," *Trends Genet.* 12:224-228 (1996).
Jeggo, et al., "Identification of Genes Involved in Repair of Dna Double-Strand Breaks in Mammalian Cells," *Radiation Research* 150:S80-S91 (1998).
Johnson, et al., "Double-Strand-Break-Induced Homologous Recombination in Mammalian Cells." *Biochemical Society Transactions* 29:196-201 (2001).
Khanna, et al., "DNA Double-Strand Breaks: Signaling, Repair and the Cancer Connection." *Nature Genetics* 27:247-254 (2001).
Kim, et at., "Construction of a Z-Dna-Specific Restriction Endonuclease," *Proc. Natl. Acad. Sci. USA* 94:12875-12879 (1997).
Kim, et al., "Hybrid Restriction Enzymes: Zinc Finger Fusions of FokI Cleavage Domain." *Proc. Natl. Acad. Sci. USA* 93:1156-1160 (1996).
Kim, et al., "Chimeric Restriction Endonuclease," *Proc. Natl. Acad. Sci. USA* 91:883-887 (1994).
Kim, et al., "Chimeric Restriction Enzyme: Gal4 Fusion to Fold Cleavage Domain," *Biol. Chem.* 379:489-495 (1998).
Kim, et al., "Insertion and Deletion of Mutants of FokI Restriction Endonuclease," *Journal of Biol. Chem.* 269(50):31978-31982 (1994).
Kita et al., "Cloning and Sequence Analysis of the Stsi Restriction-Modification Gene: Presence of Homology to Foki Restrictions-Modifcation Enzymes," *Nucleic Acids Research* 20:4167-4172 (1992).
Klein, et al., "Transformation of Microbes, Plants and Animals by Particle Bombardment," *Bio/Techniques* 10:286-291 (1992).
Klein, et al., "High-Velocity Microprojectiles for Delivering Nucleic Acids into Living Cells," *Nature* 327:70-73 (1987).
Kuehn, et al., "A Potential Animal Model for Lesch-Nyhan Syndrome Through Introduction of HPRT Mutations into Mice," *Nature* 326:295-298 (1987).
Kohn, et al., "Letter to the Editor of Nature for the American Society of Gene Therapy (Asgt) and the European Society of Gene Therapy (ESGT)," *The Journal of Gene Medicine* 5:641 (2003).
Lai, et al., Production of a-1,3-Galctosyltransferase Knockout Pigs by Nuclear Transfer Cloning, *Science* 295:1089-1092 (2002).
Li, et al., "Alteration of the Cleavage Distance of FokI Restriction Endonuclease by Insertion Mutagenesis," *Proc. Natl. Acad. Sci. USA* 90:2764-2768 (1993).

Li, et al., "Functional Domains in Fold Restriction Endonuclease," *Proc. Natl. Acad. Sci. USA* 89:4275-4279 (1992).
Liu, et al., "Validated Zinc Finger Protein Designs for All 16 GNN DNA Triplet Targets," *J. Biol. Chem.* 277(6):3850-3856 (2002).
Luo, et al., "Synthetic DNA delivery systems," *Nature Biotechnology* 18:33-37 (2000).
Maryon, et al., "Degradation of Linear DNA by a strand-specific Endonuclease Activity n Xenopus laevis oocytes," *Mol and Cell Biol* 9:4862-4871 (1989).
Mattaj, et al., "Nucleocytoplasmic Transport: The Soluble Phase," *Annu. Rev. Biochem.* 67:265-306 (1998).
McCreath, et al., "Production of Gene-Targeted Sheep by Nuclear Transfer from Cultured Somatic Cells," *Nature* 405:1066-1069 (2000).
Nahon, et al., "Targeting a Truncated Ho-Endonuclease of Yeast to Novel DNA Sites with Foreign Zinc Fingers," *Nucleic Acids Research* 26(5):1233-1239 (1998).
Odell, et al., "Identification of DNA Sequences Required for Activity of the Cauliflower Mosaic Virus 35S Promoter," *Nature* 313:810-812 (1985).
Pabo, et al., "Design and Selection of Novel Cys2his2 Zinc Finger Proteins," *Annu. Rev. Biochem.* 70:313-340 (2001).
Palu, et al., "In pursuit of new developments for gene therapy of human diseases," *J. Biotechnol* 68:1-13 (1999).
Pingoud et al., "Type II Restriction Endonucleases: Structure and Mechanism," *CMLS, Cell. Mol. Life Sci.* 62:685-707 (2005).
Porteus, et al., "Efficient Gene Targeting Mediated by Adeno-Associated Virus and DNA Double-Strand Breaks," *Mol. Cell. Biol.* 23:3558-3565 (2003).
Porteus, et al., "Chimeric Nucleases Stimulate Gene Targeting in Human Cells," *Science* 300:763 (2003) Including Supporting Online Materials.
Porteus, et al., "Gene Targeting Using Zinc Finger Nucleases," *Nature Biotechnology* 23:967-973 (2005).
Puchta, et al., "Homologous Recombination in Plant Cells is Enhanced by In Vivo Induction of Double Strand Breaks into DNA by a Site-Specific Endonuclease," *Nucleic Acids Res.* 21:5034-5040 (1993).
Rebar, et al., "Zinc Finger Phage: Affinity Selection of Fingers with New DNA-Binding Specificities," *Science* 263:671-673 (1994).
Rebar, et al., "Induction of Angiogenesis in a Mouse Model Using Engineered Transcription Factors," *Nat Med* 8(12): 1427-1432 (2002).
Ridout III, et al., "Nuclear Cloning and Epigenetic Reprogramming of the Genome," *Science* 293:1093-1098 (2001).
Rouet, et al., "Expression of a Site-Specific Endonuclease Stimulates Homologous Recombination in Mammalian Cells," *Proc. Natl. Acad. Sci. USA* 91:6064-6068 (1994).
Rouet, et al., "Introduction of Double-Strand Breaks into the Genome of Mouse Cells by Expression of a Rare-Cutting Endonuclease," *Molecular and Cellular Biology* 14(12):8096-8106 (1994).
Sanford, et al., "An Improved, Helium-Driven Biolistic Device," *Tech.-A J. of Meth. In Cell and Mol. Biol.* 3:3-16 (1991).
Sapranauskas, et al., "Novel Subtype of Type IIs Restriction Enzymes: Bfii Endonuclease Exhibits Similarities to the Edta-resistant Nuclease nuc of *Salmonella typhimurium*," *J. Biol. Chem.* 275:30878-30885 (2000).
Sapranauskas, et al., "Random Gene Dissection: A Tool for the Investigation of Protein Structural Organization," *BioTechniques* 39:395-402 (2005) Including On-Line Supplementary Material.
Sargent, et al., "Repair of Site-Specific Double-Strand Breaks in a Mammalian Chromosome by Homologous and Illegitimate Recombination," *Molecular and Cellular Biology* 17(1):267-277 (1997).
Schnieke, et al., "Human Factor IX Transgenic Sheep Produced by Transfer of Nuclei from Transfected Fetal Fibroblasts," *Science* 278:2130-2133 (1997).
Sedivy, et al., "Positive Genetic Selection for Gene Disruption in Mammalian Cells by Homologous Recombination," *Proc. Natl. Acad. Sci. USA* 86:227-231 (1989).
Segal, et al., "Endonuclease-Induced, Targeted Homologous Extrachromosomal Recombination in *Xenopus* Oocytes," *Proc. Natl. Acad. Sci. USA* 92:806-810 (1995).

(56) References Cited

OTHER PUBLICATIONS

Segal, et al., "Toward Controlling Gene Expression at Will: Selection and Design of Zinc Finger Domains Recognizing Each of the 5'-GNN-3' DNA Target Sequences," *Proc. Natl. Acad. Sci. USA* 96:2758-2763 (1999).
Segal, D. J., "The Use of Zinc Finger Peptides to Study the Role of the Specific factor Binding Sites in the Chromatin Environment," *Methods* 26:76-83 (2002).
Sera, et al., "Rational Design of Artificial Zinc-Finger Proteins Using a Nondegenerate Recognition Code table," *Biochemistry* 41:7074-7081 (2002).
Severin, et al., "Heat-Inducible Hygromycin Resistance in Transgenic Tobacco," *Plant Mol. Biol.* 15:827-833 (1990).
Shi, et al., "Specific DNA-RNA Hybrid Binding by Zinc Finger Proteins," *Science* 268:282-284 (1995).
Shin, et al., "A Cat Cloned by Nuclear Transplantation," *Nature* 415:859 (2002).
Shillito, et al., "Protoplast Isolation and Transformation," *Pint. Mol. Bio.-A Prac. App.*, Shaw, ed., IRL Press, pp. 161-186 (1988).
Simoncsits, et al., "Covalent Joining of the Subunits of a Homodimeric Type II Restriction Endonuclease: Single-Chain Pvu II Endonuclease," *J. Mol. Biol.* 309:89-97 (2001).
Smih, et al., "Double Strand Breaks at the target Locus Stimulate Gene targeting in Embryonic Stem Cells," *Nuc. Acids Res.* 23(24):5012-5019 (1995).
Smith, et al., "A Detailed Study of the Substrate Specificity of a Chimeric Restriction Enzyme," *Nuc. Acids Res.* 27(2):674-681 (1999).
Smith, et al., "Requirements for Double-Strand Cleavage by Chimeric Restriction Enzymes with Zinc Finger DNA Recognition Domains," *Nuc. Acids Res.* 28(17):3361-3369 (2000).
Sternberg, et al., "Bacteriophage P1 Site-Specific Recombination," *J. Mol. Biol.* 150:467-507 (1981).
Taghian, et al., "Chromosomal Double-Strand Breaks Induce Gene Conversion at High Frequency in Mammalian Cells," *Mole. And Cell. Biol.* 17(11):6386-6393 (1997).
Takamatsu, et al., "Expression of Bacterial Chloramphenicol Acetyltransferase Gene in Tobacco Plants Mediated by TMV-RNA," *EMBO J.* 6:307-311 (1987).
Takata, et al., "Homologous Recombination and Non-Homologous End-Joining Pathways of DNA Double-Strand Break Repair Have Overlapping Roles in the Maintenance of Chromosomal Integrity in Vertebrate Cells," *EMBO J.* 17:5497-5508 (1998).
Thierry, et al., "Cleavage of Yeast and Bacteriophage T& Genomes at a Single Site Using the Rare Cutter Endonuclease I-Sce I," *Nucleic Acids Res.* 19:189-190 (1991).
Vasileva et al., "Homologous Recombination Is Required for Aav-Mediated Gene Targeting," *Nucleic Acids Research* 34:3345-3360 (2006).
Velten, et al., "Isolation of a Dual Plant Promoter Fragment from the Ti Plasmid of Agrobacterium Tumefaciens," *EMBO J.* 3:2723-2730 (1984).
Verma, et al., "Gene therapy—promises, problems and prospects," *Nature* 389:239-242 (1997).
Verma, et al., "Gene Therapy: Twenty-First Century Medicine," *Annual Review of Biochemistry* 74:711-738 (2005).
Wah, et al., "Structure of the Multimodular Endonuclease FokI Bound to DNA," *Nature* 388:97-100 (1997).
Wang, et al., "Single-stranded Oligonucleotide-mediated Gene Repair in Mammalian Cells has a Mechanism Distinct from Homologous Recombination Repair," *Biochemical and Biophysical Research Communications* 350:568-573 (2006).
Wilmut, et al., "Viable Offspring Derived from Fetal and Adult Mammalian Cells," *Nature* 385:810-813 (1997).
Wilson, J. H., "Pointing Fingers at the Limiting Step in Gene targeting," *Nature Biotechnology* 21(7):759-760 (2003).
Wolfe, et al., "Beyond the Recognition Code: Structures of Two Cys2His2 Zinc Finger/TATA Box Complexes," *Structure* 9:727-723 (2001).
Wolfe, et al., "DNA Recognition by Cys2His2Zinc Finger Proteins." *Annu. Rev: Biophys. Biomol. Struct.* 3:183-212 (1999).
Xu, et al., "Engineering a Nicking Endonuclease N. Alwl by Domain Swapping," *PNAS* 98(23):12990-12995 (2001).
Yanez, et al., "Therapeutic Gene targeting," *Gene Therapy* 5:149-159 (1998).
Zuffrey, et al., "Woodchuck Hepatitis Virus Posttranscriptional Regulatory Element Enhances Expression of Transgenes Delivered by Retroviral Vectors," *Journal of Virology* 73(4): 2886-2892 (1999).
Koller, et al., "Inactivating the F32-Microglobulin Locus in Mouse Embryonic Stem Cells by Homologous in Recombination (Class I Antigens/ Gene Targeting)" *Genetics* 86(1):8932-8935 (1989).
Steuer, et al., "Chimeras of the Homing Endonuclease PI-SCEI and the Homologous Candida Tropicalis Intein: A Study to Explore the Possibility of Exchanging DNA-Binding Modules to Obtain Highly Specific Endonucleases With Altered Specificity," *Chembiochem.* 5(2):206-213 (2004).
Wah, et al., "Structure of FOK1 Has Implications for DNA Cleavage," *Proc. Natl. Acad. Sci. USA* (1998) vol. 95, No. 18, pp. 10564-10569.
Bicknell, et al., "β2-Microglobulin Gene Mutations: A Study of Established Colorectal Cell Lines and Fresh Tumors," *Proc. Natl. Acad. Sci. USA.* 91, pp. 4751-4755 (1994).
Bicknell, et al., "Selection for β2-Microglobulin Mutation in Mismatch Repair-Defective Colorectal Carcinomas," *Current Biology*, Vo. 6, No. 12, pp. 1695-1697 (1996).

\* cited by examiner

FIGURE 1

```
                          MetGlyPheLeuLysLeuIle  (SEQ ID NO:2)
CTGCCGCCGGCGCCGCGGCCGTCATGGGGTTCCTGAAACTGATT
GACGGCGGCCGCGGCGCCGGCAGTACCCCAAGGACTTTGACTAA  (SEQ ID NO:1)
    |    |    |    |    |    |    |    |
    5   10   15   20   25   30   35   40
```

FIGURE 6

```
TAGTCCTGCAGGTTTAAACGAATTCGCCCTTCTCAGCAAGCGTGAGCTCA      50
GGTCTCCCCCGCCTCCTTGAACCTCAAGAACTGCTCTGACTCCGCCCAGC     100
AACAACTCCTCCGGGGATCTGGTCCGCAGGAGCAAGTGTTTGTTGTTGCC     150
ATGCAACAAGAAAAGGGGGCGGAGGCACCACGCCAGTCGTCAGCTCGCTC     200
CTCGTATACGCAACATCAGTCCCCGCCCCTGGTCCCACTCCTGCCGGAAG     250
GCGAAGATCCCGTTAGGCCTGGACGTATTCTCGCGACATTTGCCGGTCGC     300
CCGGCTTGCACTGCGGCGTTTCCCGCGCGGGCTACCTCAGTTCTCGGGCG     350
TACGGCGCGGCCTGTCCTACTGCTGCCGGCGCCGCGGCCGTCATaagaag    400
cTTCCTGAAACTGATTGAAGGGCGAATTCGCGGCCGCTAAATTCAATTCG    450
CCCTATAGTGAGT
```

(SEQ ID NO: 6)

FIGURE 7

```
                        TyrLysAsnSerAspAsnAspLysVal      (SEQ ID NO:8)
CTTCCAACCTTTCTCCTCTAGGTACAAGAACTCGGATAATGATAAAGTCC
GAAGGTTGGAAAGAGGAGATCCATGTTCTTGAGCCTATTACTATTTCAGG      (SEQ ID NO:7)
    |    |    |    |    |    |    |    |    |    |
    5   10   15   20   25   30   35   40   45   50
```

FIGURE 12

```
TAGTCCTGCAGGTTTAAACGAATTCGCCCTTTCCTCTAGGTAaAAGAAtT    50
CcGAcAAcGATAAAGTCCAGAAGTGCAGCCACTATCTATTCCCTGAAGAA   100
ATCACTTCTGGCTGTCAGTTGCAAAAAAAGGAGATCCACCTCTACCAAAC   150
ATTTGTTGTTCAGCTCCAGGACCCACGGGAACCCAGGAGACAGGCCACAC   200
AGATGCTAAAACTGCAGAATCTGGGTAATTTGGAAAGAAAGGGTCAAGAG   250
ACCAGGGATACTGTGGGACATTGGAGTCTACAGAGTAGTGTTCTTTTATC   300
ATAAGGGTACATGGGCAGAAAAGAGGAGGTAGGGGATCATGATGGGAAGG   350
GAGGAGGTATTAGGGGCACTACCTTCAGGATCCTGACTTGTCTAGGCCAG   400
GGGAATGACCACATATGCACACATATCTCCAGTGATCCCCTGGGCTCCAG   450
AGAACCTAACACTTCACAAACTGAGTGAATCCCAGCTAGAACTGAACTGG   500
AACAACAGATTCTTGAACCACTGTTTGGAGCACTTGGTGCAGTACCGGAC   550
TAAGGGCGAATTCGCGGCCGCTAAATTCAATTCGCCCTATAGTGAGTCGT   600
ATTACAATTCACTGGCCGTCGTTT
```

(SEQ ID NO:12)

FIGURE 13

```
TACTGATGGTATGGGGCCAAGAGATATATCTTAGAGGGAGGGCTGAGGGT        50
TTGAAGTCCAACTCCTAAGCCAGTGCCAGAAGAGCCAAGGACAGGTACGG       100
CTGTCATCACTTAGACCTCACCCTGTGGAGCCACACCCTAGGGTTGGCCA       150
ATCTACTCCCAGGAGCAGGGAGGGCAGGAGCCAGGGCTGGGCATAAAAGT       200
CAGGGCAGAGCCATCTATTGCTTACATTTGCTTCTGACACAACTGTGTTC       250
ACTAGCAACCTCAAACAGACACCATGGTGCATCTGACTCCTGAGGAGAAG       300
TCTGCCGTTACTGCCCTGTGGGGCAAGGTGAACGTGGATGAAGTTGGTGG       350
TGAGGCCCTGGGCAGGTTGGTATCAAGGTTACAAGACAGGTTTAAGGAGA       400
CCAATAGAAACTGGGCATGTGGAGACAGAGAAGACTCTTGGGTTTCTGAT       450
AGGCACTGACTCTCTCTGCCTATTGGTCTATTTTCCCACCCTTAGGCTGC       500
TGGTGGTCTACCCTTGGACCCAGAGGTTCTTTGAGTCCTTTGGGGATCTG       550
TCCACTCCTGATGCTGTTATGGGCAACCCTAAGGTGAAGGCTCATGGCAA       600
GAAAGTGCTCGGTGCCTTTAGTGATGGCCTGGCTCACCTGGACAACCTCA       650
AGGGCACCTTTGCCACACTGAGTGAGCTGCACTGTGACAAGCTGCACGTG       700
```

(SEQ ID NO:13)

Beta globin human genomic TARGET
700 bp

FIGURE 18

```
TGCTTACCAAGCTGTGATTCCAAATATTACGTAAATACACTTGCAAAGGA      50
GGATGTTTTTAGTAGCAATTTGTACTGATGGTATGGGGCCAAGAGATATA     100
TCTTAGAGGGAGGGCTGAGGGTTTGAAGTCCAACTCCTAAGCCAGTGCCA     150
GAAGAGCCAAGGACAGGTACGGCTGTCATCACTTAGACCTCACCCTGTGG     200
AGCCACACCCTAGGGTTGGCCAATCTACTCCCAGGAGCAGGGAGGGCAGG     250
AGCCAGGGCTGGGCATAAAAGTCAGGGCAGAGCCATCTATTGCTTACATT     300
TGCTTCTGACACAACTGTGTTCACTAGCAACCTCAAACAGACACCATGGT     350
GCATCTGACTCCTGAGGAGAAGTCTGgCGTTAgTGCCCgaattccgAtcG     400
TcAACcac
```

(SEQ ID NO:14)

FIGURE 19

```
                                          5-8
CACGTTTCGTGTTCGGAGCCGCTTTAACCCACTCTGTGGAAG
GTGCAAAGCACAAGCCTCGGCGAAATTGGGTGAGACACCTTC
   5-10
```

(SEQ ID NO:15)

FIGURE 20

```
  1 MAPKKKRKVG IHGVPAAMAE RPFQCRICMR NFSRSDNLSE HIRTHTGEKP FACDICGRKF
 61 ARNAHRINHT KIHTGSQKPF QCRICMRNFS RSDTLSEHIR THTGEKPFAC DICGRKFAAR
121 STRTTHTKIH LRQKDAARGS QLVKSELEEK KSELRHKLKY VPHEYIELIE IARNSTQDRI
181 LEMKVMEFFM KVYGYRGKHL GGSRKPDGAI YTVGSPIDYG VIVDTKAYSG GYNLPIGQAD
241 EMQRYVEENQ TRNKHINPNE WWKVYPSSVT EFKFLFVSGH FKGNYKAQLT RLNHITNCNG
301 AVLSVEELLI GGEMIKAGTL TLEEVRRKFN NGEINF
```

(SEQ ID NO:16)

FIGURE 21

```
  1 MAPKKKRKVG IHGVPAAMAE RPFQCRICMR NFSRSDSLSR HIRTHTGEKP FACDICGRKF
 61 ADSSNRKTHT KIHTGGGGSQ KPFQCRICMR NFSRSDSLSV HIRTHTGEKP FACDICGRKF
121 ADRSNRITHT KIHLRQKDAA RGSQLVKSEL EEKKSELRHK LKYVPHEYIE LIEIARNSTQ
181 DRILEMKVME FFMKVYGYRG KHLGGSRKPD GAIYTVGSPI DYGVIVDTKA YSGGYNLPIG
241 QADEMQRYVE ENQTRNKHIN PNEWWKVYPS SVTEFKFLFV SGHFKGNYKA QLTRLNHITN
301 CNGAVLSVEE LLIGGEMIKA GTLTLEEVRR KFNNGEINF
```

(SEQ ID NO:17)

FIGURE 22

```
CGAATTCTGCAGTCGACGGTACCGCGGGCCCGGGATCCACCGGTCGCCACCATGGTGAGCAA
GGGCGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGTGACCACCCTGAC
CTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTAC
AAGACCCGCGCCGAGGTGAAGTTCGAGGGCGACACCCTGGTGAACCGCATCGAGCTGAAGGG
CATCGACTTCAAGGAGGACGGCAACATCCTGGGGCACAAGCTGGAGTACAACTACAACAGCC
ACAACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATCGG
CGACGGCCCCGTGCTGCTGCCCGACAACCACTACCTGAGCACCCAGTCCGCCCTGAGCAAAG
ACCCCAACGAGAAGCGCGATCACATGGTCCTGCTGGAGTTCGTGACCGCCGCCGGGATCACT
CTCGGCATGGACGAGCTGTACAAGTAAAGCGGCCGCGACTCTAGATCATAATC
```

(SEQ ID NO:18)

FIGURE 23

```
CGAATTCTGCAGTCGACGGTACCGCGGGCCCGGGATCCACCGGTCGCCACCATGGTGAGCAA
GGGCGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACCCTG
AAGTTCATCTGCACCACCGGCAAGCTGCCCGTGCCCTGGCCCACCCTCGTGACCACCCTGAC
CTACGGCGTGCAGTGCTTCAGCCGCTACCCCTAACACGAAGCAGCACGACTTCTTCAAGTCC
GCCATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGGGCA
TCGACTTCAAGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAGATCCGCCA
CAACATCGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCAAAGAC
CCCAACGAGAAGCGCGATCACATGGTCCTGCTGGAGTTCGTGACCGCCGCGGGATCACTCT
CGGCATGGACGAGCTGTACAAGTAAAGCGGCCGCGACTCTAGATCATAATC
```

(SEQ ID NO:19)

FIGURE 24
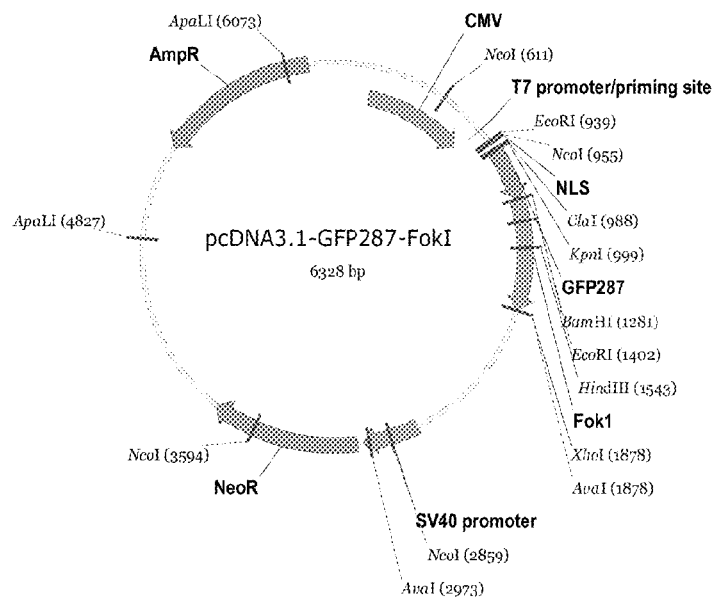
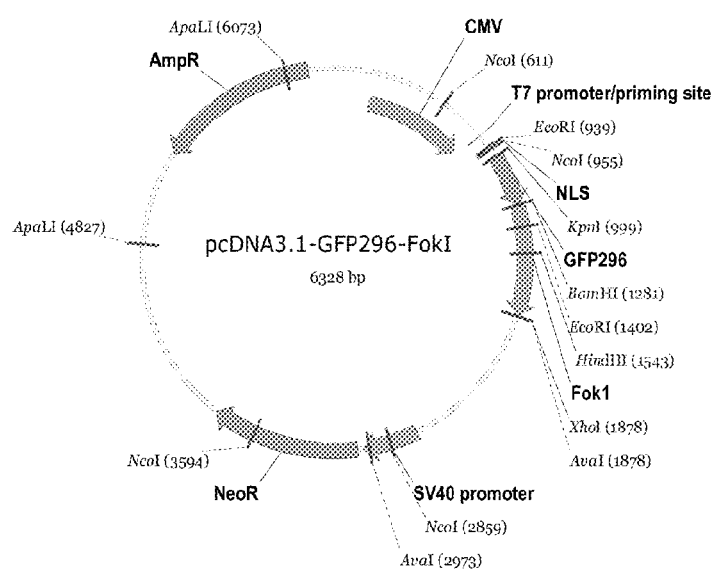

FIGURE 29

```
GGCGAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCCTGA
AGTTCATCTGCACCACCGGCAAGCTGCCCGTGCCCTGGCCCACCCTCGTGACCACCCTGACC
TACGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACA
AGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCA
CAACGTCTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCCATCGGC
GACGGCCCCGTGCTGCTGCCCGACAACCACTACCTGAGCACCCAGTCCGCCCTGAGCAAAGA
CCCCAACGAGAAGCGCGATCACATGGTCCTGCTGGAGTTCGTGACCGCCGCCGGGATCACTC
TCGGCATGGACGAGCTGTACAAGTAAAGCGGCCGCGACTCTAGATCATAATC
```

(SEQ ID NO:20)

FIGURE 32

```
GGCGAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCCTGA
AGTTCATCTGCACCACCGGCAAGCTGCCCGTGCCCTGGCCCACCCTCGTGACCACCCTGACC
TACGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACA
AGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCA
CAACGTCTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCCATCGGC
GACGGCCCCGTGCTGCTGCCCGACAACCACTACCTGAGCACCCAGTCCGCCCTGAGCAAAGA
CCCCAACGAGAAGCGCGATCACATGGTCCTGCTGGAGTTCGTGACCGCCGCCGGGATCACTC
TCGGCATGGACGAGCTGTACAAGTAAAGCGGCCGCTCGAGTCTAGAGGGCCCGTTTAAACCC
GCTGATCAGCCTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGG
GGGAGGATTGGGAAGACAATAGCAGGCATGCTGGGGATGCGGTGGGCTCTATGGCTTCTGAG
GCGGAAAGAACCAGCTGGGGCTCTAGGGGGTATCCCCACGCGCCCTGTAGCGGCGCATTAAG
CGCGGCGGGTGTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCAAGCTCTA
AATCGGGGGCTCCCTTTAGGGTTCCGATTTAGTGCTTTACGGCACCTCGACCCCAAAAAACT
TGATTAGGGTGATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAACACTCAACCCT
ATCTCGGTCTATTCTTTTGATTTATAAGGGATTTTGCCGATTTCGGCCTATTGGTTAAAAAA
TGAGCTGATTTAACAAAAATTTAACGCGAATTAATTCTGTGGAATGTGTGTCAGTTAGGGTG
TGGAAAGTCCCCAGGCTCCCCAGCAGGCAGAAGTATGCA
```

(SEQ ID NO:21)

FIGURE 40 sca-29b:

MAERPFQCRICMRNFS<u>QSGDLTR</u>HIRTHTGEKPFACDICGRKFA<u>TSANLSR</u>HTKIH
TGGGGSQKPFQCRICMRNFS<u>DRSALSR</u>HIRTHTGEKPFACDICGRKFA<u>QSGHLSR</u>
HTKIH (SEQ ID NO:22)

sca-36a:

MAERPFQCRICMRNFS<u>RSQTRKT</u>HIRTHTGEKPFACDICGRKFA<u>QKRNRTK</u>HTKIH
TGSQKPFQCRICMRNFS<u>DRSALSR</u>HIRTHTGEKPFACDICGRKFA<u>QSGNLAR</u>HTKI
H (SEQ ID NO:23)

sca-36b:

MAERPFQCRICMRNFS<u>TSGSLSR</u>HIRTHTGEKPFACDICGRKFA<u>DRSDLSR</u>HTKIH
TGGGGSQKPFQCRICMRNFS<u>DRSALSR</u>HIRTHTGEKPFACDICGRKFA<u>QSGNLAR</u>
HTKIH (SEQ ID NO:24)

sca-36c:

MAERPFQCRICMRNFS<u>TSSSLSR</u>HIRTHTGEKPFACDICGRKFA<u>DRSDLSR</u>HTKIH
TGGGGSQKPFQCRICMRNFS<u>DRSALSR</u>HIRTHTGEKPFACDICGRKFA<u>QSGNLAR</u>
HTKIH (SEQ ID NO:25)

SEQUENCE LISTING

```
<160> NUMBER OF SEQ ID NOS: 200

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: synthetic
      hSMC1L1 oligonucleotide
<220> FEATURE:
<221> NAME/KEY: misc_feature
<222> LOCATION: (5)..(16)
<223> OTHER INFORMATION: Target sequence for the hSMC1-specific ZFP
<220> FEATURE:
<221> NAME/KEY: misc_feature
<222> LOCATION: (23)..(34)
<223> OTHER INFORMATION: Target sequence for the hSMC1-specific ZFP

<400> SEQUENCE: 1
ctgccgccgg cgccgcggcc gtcatggggt tcctgaaact gatt                     44

<210> SEQ ID NO 2
<211> LENGTH: 7
<212> TYPE: PRT
```

```
<213> ORGANISM: Artificial Sequence
<220> FEATURE:
<223> OTHER INFORMATION: Description of Artificial Sequence: synthetic
      hSMC1L1 peptide

<400> SEQUENCE: 2

Met Gly Phe Leu Lys Leu Ile
1               5

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: synthetic x
      chromosome SMC1 region

<400> SEQUENCE: 3
ctgccgccgg cgccgcggcc gtcatggggt tcctgaaact gattgag            47

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: synthetic x
      chromosome SMC1 region

<400> SEQUENCE: 4

Met Gly Phe Leu Lys Leu Ile Glu
1               5

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: artificial
      donor oligonucleotide

<400> SEQUENCE: 5
ctgccgccgg cgccgcggcc gtcataagaa gcttcctgaa actgattgag         50

<210> SEQ ID NO 6
<211> LENGTH: 463
<212> TYPE: DNA
<213> ORGANISM: Artificial Sequence
<220> FEATURE:
<223> OTHER INFORMATION: Description of Artificial Sequence: an
      amplification product derived from a mutated hSMC1 gene

<400> SEQUENCE: 6
tagtcctgca ggtttaaacg aattcgccct tctcagcaag cgtgagctca ggtctccccc    60
gcctccttga acctcaagaa ctgctctgac tccgcccagc aacaactcct ccggggatct   120
ggtccgcagg agcaagtgtt tgttgttgcc atgcaacaag aaaaggggc ggaggcacca   180 cgccagtcgt cagctcgctc ctcgtatacg caacatcagt ccccgcccct ggtcccactc   240
ctgccggaag gcgaagatcc cgttaggcct ggacgtattc tcgcgacatt tgccggtcgc   300
ccggcttgca ctgcggcgtt tcccgcgcgg gctacctcag ttctcgggcg tacggcgcgg   360
cctgtcctac tgctgccggc gccgcggccg tcataagaag cttcctgaaa ctgattgaag   420
ggcgaattcg cggccgctaa attcaattcg ccctatagtg agt                     463

<210> SEQ ID NO 7
```

```
<211> LENGTH: 50
<212> TYPE: DNA
<213> ORGANISM: Artificial Sequence
<220> FEATURE:
<223> OTHER INFORMATION: Description of Artificial Sequence: synthetic
      IL2Rgamma oligonucleotide
<220> FEATURE:
<221> NAME/KEY: misc_feature
<222> LOCATION: (8)..(16)
<223> OTHER INFORMATION: Target sequence for the second pair of
      IL2Rgamma-specific ZFP
<220> FEATURE:
<221> NAME/KEY: misc_feature
<222> LOCATION: (23)..(34)
<223> OTHER INFORMATION: Target sequence for the second pair of
      IL2Rgamma-specific ZFP

<400> SEQUENCE: 7
cttccaacct ttctcctcta ggtacaagaa ctcggataat gataaagtcc            50

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: synthetic
      IL2Rgamma peptide

<400> SEQUENCE: 8

Tyr Lys Asn Ser Asp Asn Asp Lys Val
1               5

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: synthetic
      IL2Rgamma oligonucleotide

<400> SEQUENCE: 9
gttcctcttc cttccaacct ttctcctcta ggtacaagaa ctcggataat gataaagtc     59

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic
      IL2Rgamma peptide

<400> SEQUENCE: 10

Tyr Lys Asn Ser Asp Asn Asp Lys Val
1               5

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: artificial
      donor oligonucleotide

<400> SEQUENCE: 11
gttcctcttc cttccaacct ttctcctcta ggtaaaagaa ttccgacaac gataaagtc     59

<210> SEQ ID NO 12
<211> LENGTH: 624
<212> TYPE: DNA
```

<213> ORGANISM: Artificial Sequence
<220> FEATURE:
<223> OTHER INFORMATION: Description of Artificial Sequence: synthetic mutated IL2Rgamma gene

<400> SEQUENCE: 12

```
tagtcctgca ggtttaaacg aattcgccct ttcctctagg taaaagaatt ccgacaacga      60
taaagtccag aagtgcagcc actatctatt ccctgaagaa atcacttctg gctgtcagtt     120
gcaaaaaaag gagatccacc tctaccaaac atttgttgtt cagctccagg acccacggga    180
acccaggaga caggccacac agatgctaaa actgcagaat ctgggtaatt tggaaagaaa    240
gggtcaagag accagggata ctgtgggaca ttggagtcta cagagtagtg ttcttttatc    300
ataagggtac atgggcagaa agaggaggt aggggatcat gatgggaagg gaggaggtat     360 tagggcact accttcagga tcctgacttg tctaggccag gggaatgacc acatatgcac     420
acatatctcc agtgatcccc tgggctccag agaacctaac acttcacaaa ctgagtgaat    480
cccagctaga actgaactgg aacaacagat tcttgaacca ctgtttggag cacttggtgc    540
agtaccggac taagggcgaa ttcgcggccg ctaaattcaa ttcgccctat agtgagtcgt    600
attacaattc actggccgtc gttt                                            624
```

<210> SEQ ID NO 13
<211> LENGTH: 700
<212> TYPE: DNA
<213> ORGANISM: Artificial Sequence
<220> FEATURE:
<223> OTHER INFORMATION: Description of Artificial Sequence: synthetic beta-globin gene

<400> SEQUENCE: 13

```
tactgatggt atggggccaa gagatatatc ttagagggag ggctgagggt ttgaagtcca      60
actcctaagc cagtgccaga agagccaagg acaggtacgg ctgtcatcac ttagacctca    120
ccctgtggag ccacacccta gggttggcca atctactccc aggagcaggg agggcaggag    180
ccagggctgg gcataaaagt cagggcagag ccatctattg cttacatttg cttctgacac    240
aactgtgttc actagcaacc tcaaacagac accatggtgc atctgactcc tgaggagaag    300
tctgccgtta ctgccctgtg gggcaaggtg aacgtggatg aagttggtgg tgaggccctg    360
ggcaggttgg tatcaaggtt acaagacagg tttaaggaga ccaatagaaa ctgggcatgt    420
ggagacagag aagactcttg ggtttctgat aggcactgac tctctctgcc tattggtcta    480
ttttcccacc cttaggctgc tggtggtcta cccttggacc cagaggttct ttgagtcctt    540
tggggatctg tccactcctg atgctgttat gggcaaccct aaggtgaagg ctcatggcaa    600
gaaagtgctc ggtgccttta gtgatggcct ggctcacctg gacaacctca agggcacctt    660
tgccacactg agtgagctgc actgtgacaa gctgcacgtg                          700
```

<210> SEQ ID NO 14
<211> LENGTH: 408
<212> TYPE: DNA
<213> ORGANISM: Artificial Sequence
<220> FEATURE:
<223> OTHER INFORMATION: Description of Artificial Sequence: synthetic amplification product derived from a mutated beta-globin gene

<400> SEQUENCE: 14

```
tgcttaccaa gctgtgattc caaatattac gtaaatacac ttgcaaagga ggatgttttt      60
agtagcaatt tgtactgatg gtatggggcc aagagatata tcttagaggg agggctgagg    120
```

```
gtttgaagtc caactcctaa gccagtgcca aagagccaa ggacaggtac ggctgtcatc    180
acttagacct caccctgtgg agccacaccc tagggttggc caatctactc ccaggagcag    240
ggagggcagg agccagggct gggcataaaa gtcagggcag agccatctat tgcttacatt    300
tgcttctgac acaactgtgt tcactagcaa cctcaaacag acaccatggt gcatctgact    360
cctgaggaga agtctggcgt tagtgcccga attccgatcg tcaaccac                 408
```

```
<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: synthetic
      IL-2Rgamma oligonucleotide
<220> FEATURE:
<221> NAME/KEY: misc_feature
<222> LOCATION: (1)..(13)
<223> OTHER INFORMATION: target sequences for the 5-10 ZFP/FokI fusion
      protein
<220> FEATURE:
<221> NAME/KEY: misc_feature
<222> LOCATION: (31)..(42)
<223> OTHER INFORMATION: target sequences for the 5-8 ZFP/FokI fusion
      protein

<400> SEQUENCE: 15
cacgtttcgt gttcggagcc gctttaaccc actctgtgga ag                        42
```

```
<210> SEQ ID NO 16
<211> LENGTH: 336
<212> TYPE: PRT
<213> ORGANISM: Artificial Sequence
<220> FEATURE:
<223> OTHER INFORMATION: Description of Artificial Sequence: synthetic
      5-8 ZFP/FokI fusion polypeptide
<220> FEATURE:
<221> NAME/KEY: MISC_FEATURE
<222> LOCATION: (1)..(17)
<223> OTHER INFORMATION: NLS
<220> FEATURE:
<221> NAME/KEY: MISC_FEATURE
<222> LOCATION: (18)..(130)
<223> OTHER INFORMATION: ZFP
<220> FEATURE:
<221> NAME/KEY: MISC_FEATURE
<222> LOCATION: (131)..(140)
<223> OTHER INFORMATION: ZC linker
<220> FEATURE:
<221> NAME/KEY: MISC_FEATURE
<222> LOCATION: (141)..(336)
<223> OTHER INFORMATION: FokI cleavage half-domain
```

<400> SEQUENCE: 16

```
Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Asn Leu Ser Glu His Ile Arg Thr His Thr Gly Glu
        35                  40                  45

Lys Pro Phe Ala Cys Asp Ile Cys Gly Arg Lys Phe Ala Arg Asn Ala
    50                  55                  60

His Arg Ile Asn His Thr Lys Ile His Thr Gly Ser Gln Lys Pro Phe
65                  70                  75                  80

Gln Cys Arg Ile Cys Met Arg Asn Phe Ser Arg Ser Asp Thr Leu Ser
                85                  90                  95

Glu His Ile Arg Thr His Thr Gly Glu Lys Pro Phe Ala Cys Asp Ile
```

```
                100                 105                 110
Cys Gly Arg Lys Phe Ala Ala Arg Ser Thr Arg Thr Thr His Thr Lys
        115                 120                 125

Ile His Leu Arg Gln Lys Asp Ala Ala Arg Gly Ser Gln Leu Val Lys
        130                 135             140

Ser Glu Leu Glu Glu Lys Lys Ser Glu Leu Arg His Lys Leu Lys Tyr
145                 150                 155                 160

Val Pro His Glu Tyr Ile Glu Leu Ile Glu Ile Ala Arg Asn Ser Thr
                165                 170                 175

Gln Asp Arg Ile Leu Glu Met Lys Val Met Glu Phe Phe Met Lys Val
            180                 185                 190

Tyr Gly Tyr Arg Gly Lys His Leu Gly Gly Ser Arg Lys Pro Asp Gly
        195                 200                 205

Ala Ile Tyr Thr Val Gly Ser Pro Ile Asp Tyr Gly Val Ile Val Asp
    210                 215                 220

Thr Lys Ala Tyr Ser Gly Gly Tyr Asn Leu Pro Ile Gly Gln Ala Asp
225                 230                 235                 240

Glu Met Gln Arg Tyr Val Glu Asn Gln Thr Arg Asn Lys His Ile
                245                 250                 255

Asn Pro Asn Glu Trp Trp Lys Val Tyr Pro Ser Ser Val Thr Glu Phe
                260                 265                 270

Lys Phe Leu Phe Val Ser Gly His Phe Lys Gly Asn Tyr Lys Ala Gln
            275                 280                 285

Leu Thr Arg Leu Asn His Ile Thr Asn Cys Asn Gly Ala Val Leu Ser
        290                 295                 300

Val Glu Glu Leu Leu Ile Gly Gly Glu Met Ile Lys Ala Gly Thr Leu
305                 310                 315                 320

Thr Leu Glu Glu Val Arg Arg Lys Phe Asn Asn Gly Glu Ile Asn Phe
                325                 330                 335

<210> SEQ ID NO 17
<211> LENGTH: 339
<212> TYPE: PRT
<213> ORGANISM: Artificial Sequence
<220> FEATURE:
<223> OTHER INFORMATION: Description of Artificial Sequence: synthetic
      5-10 ZFP/FokI fusion polypeptide
<220> FEATURE:
<221> NAME/KEY: MISC_FEATURE
<222> LOCATION: (1)..(17)
<223> OTHER INFORMATION: NLS
<220> FEATURE:
<221> NAME/KEY: MISC_FEATURE
<222> LOCATION: (18)..(133)
<223> OTHER INFORMATION: ZFP
<220> FEATURE:
<221> NAME/KEY: MISC_FEATURE
<222> LOCATION: (134)..(143)
<223> OTHER INFORMATION: ZC linker
<220> FEATURE:
<221> NAME/KEY: MISC_FEATURE
<222> LOCATION: (144)..(339)
<223> OTHER INFORMATION: FokI cleavage half-domain

<400> SEQUENCE: 17

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Ser Leu Ser Arg His Ile Arg Thr His Thr Gly Glu
        35                  40                  45
```

Lys Pro Phe Ala Cys Asp Ile Cys Gly Arg Lys Phe Ala Asp Ser Ser
 50                  55                  60

Asn Arg Lys Thr His Thr Lys Ile His Thr Gly Gly Gly Gly Ser Gln
 65                  70                  75                  80

Lys Pro Phe Gln Cys Arg Ile Cys Met Arg Asn Phe Ser Arg Ser Asp
                 85                  90                  95

Ser Leu Ser Val His Ile Arg Thr His Thr Gly Glu Lys Pro Phe Ala
             100                 105                 110

Cys Asp Ile Cys Gly Arg Lys Phe Ala Asp Arg Ser Asn Arg Ile Thr
         115                 120                 125

His Thr Lys Ile His Leu Arg Gln Lys Asp Ala Ala Arg Gly Ser Gln
     130                 135                 140

Leu Val Lys Ser Glu Leu Glu Glu Lys Ser Glu Leu Arg His Lys
145                 150                 155                 160

Leu Lys Tyr Val Pro His Glu Tyr Ile Glu Leu Ile Glu Ile Ala Arg
                 165                 170                 175

Asn Ser Thr Gln Asp Arg Ile Leu Glu Met Lys Val Met Glu Phe Phe
             180                 185                 190

Met Lys Val Tyr Gly Tyr Arg Gly Lys His Leu Gly Gly Ser Arg Lys
         195                 200                 205

Pro Asp Gly Ala Ile Tyr Thr Val Gly Ser Pro Ile Asp Tyr Gly Val
     210                 215                 220

Ile Val Asp Thr Lys Ala Tyr Ser Gly Gly Tyr Asn Leu Pro Ile Gly
225                 230                 235                 240

Gln Ala Asp Glu Met Gln Arg Tyr Val Glu Glu Asn Gln Thr Arg Asn
                 245                 250                 255

Lys His Ile Asn Pro Asn Glu Trp Trp Lys Val Tyr Pro Ser Ser Val
             260                 265                 270

Thr Glu Phe Lys Phe Leu Phe Val Ser Gly His Phe Lys Gly Asn Tyr
         275                 280                 285

Lys Ala Gln Leu Thr Arg Leu Asn His Ile Thr Asn Cys Asn Gly Ala
     290                 295                 300

Val Leu Ser Val Glu Glu Leu Leu Ile Gly Gly Glu Met Ile Lys Ala
305                 310                 315                 320

Gly Thr Leu Thr Leu Glu Glu Val Arg Arg Lys Phe Asn Asn Gly Glu
                 325                 330                 335

Ile Asn Phe

<210> SEQ ID NO 18
<211> LENGTH: 797
<212> TYPE: DNA
<213> ORGANISM: Artificial Sequence
<220> FEATURE:
<223> OTHER INFORMATION: Description of Artificial Sequence: synthetic
      enhanced Green Fluorescent Protein gene

<400> SEQUENCE: 18
cgaattctgc agtcgacggt accgcgggcc cgggatccac cggtcgccac catggtgagc    60
aagggcgagg agctgttcac cggggtggtg cccatcctgg tcgagctgga cggcgacgta   120
aacggccaca agttcagcgt gtccggcgag ggcgagggcg atgccaccta cggcaagctg   180
accctgaagt tcatctgcac caccggcaag ctgcccgtgc cctggcccac cctcgtgacc   240
accctgacct acggcgtgca gtgcttcagc cgctaccccg accacatgaa gcagcacgac   300
ttcttcaagt ccgccatgcc cgaaggctac gtccaggagc gcaccatctt cttcaaggac   360

```
gacggcaact acaagacccg cgccgaggtg aagttcgagg gcgacaccct ggtgaaccgc    420
atcgagctga agggcatcga cttcaaggag gacggcaaca tcctgggggca caagctggag   480 tacaactaca acagccacaa cgtctatatc atggccgaca gcagaagaa cggcatcaag    540 gtgaacttca agatccgcca caacatcgag gacggcagcg tgcagctcgc cgaccactac   600
cagcagaaca cccccatcgg cgacggcccc gtgctgctgc ccgacaacca ctacctgagc   660
acccagtccg ccctgagcaa agaccccaac gagaagcgcg atcacatggt cctgctggag   720
ttcgtgaccg ccgccgggat cactctcggc atggacgagc tgtacaagta aagcggccgc   780
gactctagat cataatc                                                  797

<210> SEQ ID NO 19
<211> LENGTH: 795
<212> TYPE: DNA
<213> ORGANISM: Artificial Sequence
<220> FEATURE:
<223> OTHER INFORMATION: Description of Artificial Sequence: synthetic
      mutant defective eGFP gene

<400> SEQUENCE: 19
cgaattctgc agtcgacggt accgcgggcc cgggatccac cggtcgccac catggtgagc    60
aagggcgagg agctgttcac cggggtggtg cccatcctgg tcgagctgga cggcgacgta   120
aacggccaca gttcagcgt gtccggcgag ggcgagggcg atgccaccta cggcaagctg    180
accctgaagt tcatctgcac caccggcaag ctgcccgtgc cctggcccac cctcgtgacc   240
accctgacct acggcgtgca gtgcttcagc cgctacccct aacacgaagc agcacgactt   300
cttcaagtcc gccatgcccg aaggctacgt ccaggagcgc accatcttct tcaaggacga   360
cggcaactac aagacccgcg ccgaggtgaa gttcgagggc gacaccctgg tgaaccgcat   420
cgagctgaag ggcatcgact tcaaggagga cggcaacatc ctggggcaca gctggagta    480 caactacaac agccacaacg tctatatcat ggccgacaag cagaagaacg gcatcaaggt   540
gaacttcaag atccgccaca acatcgagga cggcagcgtg cagctcgccg accactacca   600
gcagaacacc cccatcggcg acggccccgt gctgctgccc gacaaccact acctgagcac   660
ccagtccgcc ctgagcaaag accccaacga gaagcgcgat cacatggtcc tgctggagtt   720
cgtgaccgcc gccgggatca ctctcggcat ggacgagctg tacaagtaaa gcggccgcga   780
ctctagatca taatc                                                    795

<210> SEQ ID NO 20
<211> LENGTH: 734
<212> TYPE: DNA
<213> ORGANISM: Artificial Sequence
<220> FEATURE:
<223> OTHER INFORMATION: Description of Artificial Sequence: synthetic
      eGFP insert in pCR(R)4-TOPO-GFPdonor5

<400> SEQUENCE: 20
ggcgaggagc tgttcaccgg ggtggtgccc atcctggtcg agctggacgg cgacgtaaac    60
ggccacaagt tcagcgtgtc cggcgagggc gagggcgatg ccacctacgg caagctgacc   120
ctgaagttca tctgcaccac cggcaagctg cccgtgccct ggcccaccct cgtgaccacc   180
ctgacctacg gcgtgcagtg cttcagccgc taccccgacc acatgaagca gcacgacttc   240
ttcaagtccg ccatgcccga aggctacgtc caggagcgca ccatcttctt caaggacgac   300
ggcaactaca gacccgcgc cgaggtgaag ttcgagggcg acaccctggt gaaccgcatc    360
```

```
gagctgaagg gcatcgactt caaggaggac ggcaacatcc tggggcacaa gctggagtac    420
aactacaaca gccacaacgt ctatatcatg gccgacaagc agaagaacgg catcaaggtg    480
aacttcaaga tccgccacaa catcgaggac ggcagcgtgc agctcgccga ccactaccag    540
cagaacaccc ccatcggcga cggccccgtg ctgctgcccg acaaccacta cctgagcacc    600
cagtccgccc tgagcaaaga ccccaacgag aagcgcgatc acatggtcct gctggagttc    660
gtgaccgccg ccgggatcac tctcggcatg gacgagctgt acaagtaaag cggccgcgac    720
tctagatcat aatc                                                      734

<210> SEQ ID NO 21
<211> LENGTH: 1527
<212> TYPE: DNA
<213> ORGANISM: Artificial Sequence
<220> FEATURE:
<223> OTHER INFORMATION: Description of Artificial Sequence: synthetic
      eGFP insert in pCR(R)4-TOPO

<400> SEQUENCE: 21
ggcgaggagc tgttcaccgg ggtggtgccc atcctggtcg agctggacgg cgacgtaaac     60
ggccacaagt tcagcgtgtc cggcgagggc gagggcgatg ccacctacgg caagctgacc    120
ctgaagttca tctgcaccac cggcaagctg cccgtgccct ggcccaccct cgtgaccacc    180
ctgacctacg gcgtgcagtg cttcagccgc taccccgacc acatgaagca gcacgacttc    240
ttcaagtccg ccatgcccga aggctacgtc caggagcgca ccatcttctt caaggacgac    300
ggcaactaca agacccgcgc cgaggtgaag ttcgagggcg acaccctggt gaaccgcatc    360
gagctgaagg gcatcgactt caaggaggac ggcaacatcc tggggcacaa gctggagtac    420
aactacaaca gccacaacgt ctatatcatg gccgacaagc agaagaacgg catcaaggtg    480
aacttcaaga tccgccacaa catcgaggac ggcagcgtgc agctcgccga ccactaccag    540
cagaacaccc ccatcggcga cggccccgtg ctgctgcccg acaaccacta cctgagcacc    600
cagtccgccc tgagcaaaga ccccaacgag aagcgcgatc acatggtcct gctggagttc    660
gtgaccgccg ccgggatcac tctcggcatg gacgagctgt acaagtaaag cggccgctcg    720
agtctagagg gcccgtttaa acccgctgat cagcctcgac tgtgccttct agttgccagc    780
catctgttgt ttgcccctcc cccgtgcctt ccttgaccct ggaaggtgcc actcccactg    840
tcctttccta ataaaatgag gaaattgcat cgcattgtct gagtaggtgt cattctattc    900
tggggggtgg ggtggggcag gacagcaagg gggaggattg ggaagacaat agcaggcatg    960
ctggggatgc ggtgggctct atggcttctg aggcggaaag aaccagctgg ggctctaggg   1020
ggtatcccca cgcgccctgt agcggcgcat taagcgcggc gggtgtggtg gttacgcgca   1080
gcgtgaccgc tacacttgcc agcgccctag cgcccgctcc tttcgctttc ttcccttcct   1140
ttctcgccac gttcgccggc tttccccgtc aagctctaaa tcggggctc cctttagggt   1200 tccgatttag tgctttacgg cacctcgacc ccaaaaaact tgattagggt gatggttcac   1260
gtagtgggcc atcgccctga tagacggttt ttcgcccttt gacgttggag tccacgttct   1320
ttaatagtgg actcttgttc caaactggaa caacactcaa ccctatctcg gtctattctt   1380
ttgatttata agggattttg ccgatttcgg cctattggtt aaaaaatgag ctgatttaac   1440
aaaaatttaa cgcgaattaa ttctgtggaa tgtgtgtcag ttagggtgtg gaaagtcccc   1500
aggctcccca gcaggcagaa gtatgca                                       1527

<210> SEQ ID NO 22
```

```
<211> LENGTH: 116
<212> TYPE: PRT
<213> ORGANISM: Artificial Sequence
<220> FEATURE:
<223> OTHER INFORMATION: Description of Artificial Sequence: synthetic
      sca-29b polypeptide

<400> SEQUENCE: 22

Met Ala Glu Arg Pro Phe Gln Cys Arg Ile Cys Met Arg Asn Phe Ser
1               5                   10                  15

Gln Ser Gly Asp Leu Thr Arg His Ile Arg Thr His Thr Gly Glu Lys
            20                  25                  30

Pro Phe Ala Cys Asp Ile Cys Gly Arg Lys Phe Ala Thr Ser Ala Asn
        35                  40                  45

Leu Ser Arg His Thr Lys Ile His Thr Gly Gly Gly Ser Gln Lys
    50                  55                  60

Pro Phe Gln Cys Arg Ile Cys Met Arg Asn Phe Ser Asp Arg Ser Ala
65                  70                  75                  80

Leu Ser Arg His Ile Arg Thr His Thr Gly Glu Lys Pro Phe Ala Cys
                85                  90                  95

Asp Ile Cys Gly Arg Lys Phe Ala Gln Ser Gly His Leu Ser Arg His
            100                 105                 110

Thr Lys Ile His
        115

<210> SEQ ID NO 23
<211> LENGTH: 113
<212> TYPE: PRT
<213> ORGANISM: Artificial Sequence
<220> FEATURE:
<223> OTHER INFORMATION: Description of Artificial Sequence: synthetic
      sca-36a polypeptide

<400> SEQUENCE: 23

Met Ala Glu Arg Pro Phe Gln Cys Arg Ile Cys Met Arg Asn Phe Ser
1               5                   10                  15

Arg Ser Gln Thr Arg Lys Thr His Ile Arg Thr His Thr Gly Glu Lys
            20                  25                  30

Pro Phe Ala Cys Asp Ile Cys Gly Arg Lys Phe Ala Gln Lys Arg Asn
        35                  40                  45

Arg Thr Lys His Thr Lys Ile His Thr Gly Ser Gln Lys Pro Phe Gln
    50                  55                  60

Cys Arg Ile Cys Met Arg Asn Phe Ser Asp Arg Ser Ala Leu Ser Arg
65                  70                  75                  80

His Ile Arg Thr His Thr Gly Glu Lys Pro Phe Ala Cys Asp Ile Cys
                85                  90                  95

Gly Arg Lys Phe Ala Gln Ser Gly Asn Leu Ala Arg His Thr Lys Ile
            100                 105                 110

His

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: synthetic
      sca-36b polypeptide

<400> SEQUENCE: 24

Met Ala Glu Arg Pro Phe Gln Cys Arg Ile Cys Met Arg Asn Phe Ser
```

```
                1               5                   10                  15
Thr Gly Ser Leu Ser Arg His Ile Arg Thr His Thr Gly Glu Lys
            20                  25                  30

Pro Phe Ala Cys Asp Ile Cys Gly Arg Lys Phe Ala Asp Arg Ser Asp
            35                  40                  45

Leu Ser Arg His Thr Lys Ile His Thr Gly Gly Gly Ser Gln Lys
            50                  55                  60

Pro Phe Gln Cys Arg Ile Cys Met Arg Asn Phe Ser Asp Arg Ser Ala
65                  70                  75                  80

Leu Ser Arg His Ile Arg Thr His Thr Gly Glu Lys Pro Phe Ala Cys
                85                  90                  95

Asp Ile Cys Gly Arg Lys Phe Ala Gln Ser Gly Asn Leu Ala Arg His
            100                 105                 110

Thr Lys Ile His
            115

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: synthetic
      sca-36c polypeptide

<400> SEQUENCE: 25

Met Ala Glu Arg Pro Phe Gln Cys Arg Ile Cys Met Arg Asn Phe Ser
1               5                   10                  15

Thr Ser Ser Leu Ser Arg His Ile Arg Thr His Thr Gly Glu Lys
            20                  25                  30

Pro Phe Ala Cys Asp Ile Cys Gly Arg Lys Phe Ala Asp Arg Ser Asp
            35                  40                  45

Leu Ser Arg His Thr Lys Ile His Thr Gly Gly Gly Ser Gln Lys
            50                  55                  60

Pro Phe Gln Cys Arg Ile Cys Met Arg Asn Phe Ser Asp Arg Ser Ala
65                  70                  75                  80

Leu Ser Arg His Ile Arg Thr His Thr Gly Glu Lys Pro Phe Ala Cys
                85                  90                  95

Asp Ile Cys Gly Arg Lys Phe Ala Gln Ser Gly Asn Leu Ala Arg His
            100                 105                 110

Thr Lys Ile His
            115

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: synthetic
      fusion nuclease peptide

<400> SEQUENCE: 26

His Gln Arg Thr His Gln Asn Lys Lys Gln Leu Val
1               5                   10

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: synthetic
``` hSMC1L1 Gene target sequence

<400> SEQUENCE: 27
catggggttc ct                                                            12

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F1 peptide

<400> SEQUENCE: 28

Arg Ser His Asp Leu Ile Glu
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F2 peptide

<400> SEQUENCE: 29

Thr Ser Ser Ser Leu Ser Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F3 peptide

<400> SEQUENCE: 30

Arg Ser Asp His Leu Ser Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F4 peptide

<400> SEQUENCE: 31

Thr Asn Ser Asn Arg Ile Thr
1               5

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: synthetic
      hSMC1L1 Gene target sequence

<400> SEQUENCE: 32
gcggcgccgg cg                                                            12

<210> SEQ ID NO 33
<211> LENGTH: 7
<212> TYPE: PRT

```
<213> ORGANISM: Artificial Sequence
<220> FEATURE:
<223> OTHER INFORMATION: Description of Artificial Sequence: synthetic
      hSMC1L1 Gene F1 peptide

<400> SEQUENCE: 33

Arg Ser Asp Asp Leu Ser Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F2 peptide

<400> SEQUENCE: 34

Arg Ser Asp Asp Arg Lys Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F3 peptide

<400> SEQUENCE: 35

Arg Ser Glu Asp Leu Ile Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: synthetic
      hSMC1L1 Gene F4 peptide

<400> SEQUENCE: 36

Arg Ser Asp Thr Leu Ser Arg
1               5

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: synthetic
      hSMC1L1 Gene Initial amp 1 oligonucleotide

<400> SEQUENCE: 37
agcaacaact cctccgggga tc                                              22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: synthetic
      hSMC1L1 Gene Initial amp 2 oligonucleotide

<400> SEQUENCE: 38
ttccagacgc gactctttgg c                                               21
```

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: synthetic
      hSMC1L1 Gene Chromosome-specific primer

<400> SEQUENCE: 39
ctcagcaagc gtgagctcag gtctc                                           25

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: synthetic
      hSMC1L1 Gene Donor-specific primer

<400> SEQUENCE: 40
caatcagttt caggaagctt ctt                                             23

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: synthetic
      hSMC1L1 Gene Ourside 1 oligonucleotide

<400> SEQUENCE: 41
ctcagcaagc gtgagctcag gtctc                                           25

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: synthetic
      hSMC1L1 Gene Ourside 2 oligonucleotide

<400> SEQUENCE: 42
ggggtcaagt aaggctggga agc                                             23

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence: synthetic
      IL2Rgamma Gene target sequence

<400> SEQUENCE: 43
aactcggata at                                                         12

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F1 peptide

<400> SEQUENCE: 44

Asp Arg Ser Thr Leu Ile Glu
1               5

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 45

Ser Ser Ser Asn Leu Ser Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F3 peptide

<400> SEQUENCE: 46

Arg Ser Asp Asp Leu Ser Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F4 peptide

<400> SEQUENCE: 47

Asp Asn Ser Asn Arg Ile Lys
1               5

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: synthetic
      IL2Rgamma Gene target sequence

<400> SEQUENCE: 48
tagaggagaa agg                                                      13

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F1 peptide

<400> SEQUENCE: 49

Arg Ser Asp Asn Leu Ser Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 50
```

-continued

Thr Ser Ser Ser Arg Ile Asn
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F3 peptide

<400> SEQUENCE: 51

Arg Ser Asp His Leu Ser Gln
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F4 peptide

<400> SEQUENCE: 52

Arg Asn Ala Asp Arg Lys Thr
1               5

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: synthetic
      IL2Rgamma Gene target sequence

<400> SEQUENCE: 53
tacaagaact cg                                                          12

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F1 peptide

<400> SEQUENCE: 54

Arg Ser Asp Asp Leu Ser Lys
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 55

Asp Asn Ser Asn Arg Ile Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: synthetic IL2Rgamma Gene F3 peptide

<400> SEQUENCE: 56

Arg Ser Asp Ala Leu Ser Val
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F4 peptide

<400> SEQUENCE: 57

Asp Asn Ala Asn Arg Thr Lys
1               5

<210> SEQ ID NO 58
<211> LENGTH: 9
<212> TYPE: DNA
<213> ORGANISM: Artificial Sequence
<220> FEATURE:
<223> OTHER INFORMATION: Description of Artificial Sequence: synthetic
      IL2Rgamma Gene target sequence

<400> SEQUENCE: 58 ggagaaagg                                                                  9

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F1 peptide

<400> SEQUENCE: 59

Arg Ser Asp His Leu Thr Gln
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 60

Gln Ser Gly Asn Leu Ala Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F3 peptide

<400> SEQUENCE: 61

Arg Ser Asp His Leu Ser Arg
1               5

<210> SEQ ID NO 62
<211> LENGTH: 18

```
<212> TYPE: DNA
<213> ORGANISM: Artificial Sequence
<220> FEATURE:
<223> OTHER INFORMATION: Description of Artificial Sequence: synthetic
      replaced sequence

<400> SEQUENCE: 62
tacaagaact cggataat                                                  18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: synthetic
      replacing sequence

<400> SEQUENCE: 63
taaaagaatt ccgacaac                                                  18

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: synthetic
      IL2Rgamma Gene Initial amp 1 oligonucleotide

<400> SEQUENCE: 64
tgtcgagtac atgaattgca cttgg                                          25

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: synthetic
      IL2Rgamma Gene Initial amp 2 oligonucleotide

<400> SEQUENCE: 65
ttaggttctc tggagcccag gg                                             22

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: synthetic
      IL2Rgamma Gene Chromosome-specific primer

<400> SEQUENCE: 66
ctccaaacag tggttcaaga atctg                                          25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: synthetic
      IL2Rgamma Gene Donor-specific primer

<400> SEQUENCE: 67
tcctctaggt aaagaattcc gacaac                                         26

<210> SEQ ID NO 68
<211> LENGTH: 12
<212> TYPE: DNA
```

```
<213> ORGANISM: Artificial Sequence
<220> FEATURE:
<223> OTHER INFORMATION: Description of Artificial Sequence: synthetic
      beta-globin Gene target sequence

<400> SEQUENCE: 68
gggcagtaac gg                                                          12

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F1 peptide

<400> SEQUENCE: 69

Arg Ser Asp His Leu Ser Glu
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F2 peptide

<400> SEQUENCE: 70

Gln Ser Ala Asn Arg Thr Lys
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F3 peptide

<400> SEQUENCE: 71

Arg Ser Asp Asn Leu Ser Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F4 peptide

<400> SEQUENCE: 72

Arg Ser Gln Asn Arg Thr Arg
1               5

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: synthetic
      beta-globin Gene target sequence

<400> SEQUENCE: 73
aaggtgaacg tg                                                          12
```

```
<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F1 peptide

<400> SEQUENCE: 74

Arg Ser Asp Ser Leu Ser Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F2 peptide

<400> SEQUENCE: 75

Asp Ser Ser Asn Arg Lys Thr
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F3 peptide

<400> SEQUENCE: 76

Arg Ser Asp Ser Leu Ser Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: synthetic
      beta-globin Gene F4 peptide

<400> SEQUENCE: 77

Arg Asn Asp Asn Arg Lys Thr
1               5

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: synthetic
      replaced sequence

<400> SEQUENCE: 78
ccgttactgc cctgtggggc aaggtgaacg tg                                   32

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence: synthetic
      replacing sequence

<400> SEQUENCE: 79
```
gcgttagtgc ccgaattccg atcgtcaacc ac                                         32

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: synthetic
      beta-globin gene Initial amp 1 oligonucleotide

<400> SEQUENCE: 80
tactgatggt atggggccaa gag                                                   23

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: synthetic
      beta-globin gene Initial amp 2 oligonucleotide

<400> SEQUENCE: 81
cacgtgcagc ttgtcacagt gc                                                    22

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: synthetic
      beta-globin gene Chromosome-specific primer

<400> SEQUENCE: 82
tgcttaccaa gctgtgattc ca                                                    22

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: synthetic
      beta-globin gene Donor-specific primer

<400> SEQUENCE: 83
ggttgacgat cggaattc                                                         18

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: synthetic
      target site for the ZFP oligonucleotide

<400> SEQUENCE: 84
aactcggata at                                                               12

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: synthetic
      F1 peptide

<400> SEQUENCE: 85

Asp Arg Ser Thr Leu Ile Glu

```
<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: synthetic
      F2 peptide

<400> SEQUENCE: 86

Ser Ser Ser Asn Leu Ser Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: synthetic
      F3 peptide

<400> SEQUENCE: 87

Arg Ser Asp Asp Leu Ser Lys
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: synthetic
      F4 peptide

<400> SEQUENCE: 88

Asp Asn Ser Asn Arg Ile Lys
1               5

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: synthetic
      10-residue linker
<220> FEATURE:
<221> NAME/KEY: MISC_FEATURE
<222> LOCATION: (6)..(15)
<223> OTHER INFORMATION: ZC linker

<400> SEQUENCE: 89

His Thr Lys Ile His Leu Arg Gln Lys Asp Ala Ala Arg Gly Ser Gln
1               5                   10                  15

Leu Val

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: synthetic
      6-residue linker
<220> FEATURE:
<221> NAME/KEY: MISC_FEATURE
<222> LOCATION: (6)..(11)
<223> OTHER INFORMATION: ZC linker

<400> SEQUENCE: 90
```

His Thr Lys Ile His Leu Arg Gln Lys Gly Ser Gln Leu Val
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: synthetic
      5-residue linker
<220> FEATURE:
<221> NAME/KEY: MISC_FEATURE
<222> LOCATION: (6)..(10)
<223> OTHER INFORMATION: ZC linker

<400> SEQUENCE: 91

His Thr Lys Ile His Leu Arg Gln Gly Ser Gln Leu Val
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: synthetic
      4-residue linker
<220> FEATURE:
<221> NAME/KEY: MISC_FEATURE
<222> LOCATION: (6)..(9)
<223> OTHER INFORMATION: ZC linker

<400> SEQUENCE: 92

His Thr Lys Ile His Leu Arg Gly Ser Gln Leu Val
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: synthetic
      3-residue linker
<220> FEATURE:
<221> NAME/KEY: MISC_FEATURE
<222> LOCATION: (6)..(8)
<223> OTHER INFORMATION: ZC linker

<400> SEQUENCE: 93

His Thr Lys Ile His Leu Gly Ser Gln Leu Val
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: synthetic
      2-residue linker
<220> FEATURE:
<221> NAME/KEY: MISC_FEATURE
<222> LOCATION: (6)..(7)
<223> OTHER INFORMATION: ZC linker

<400> SEQUENCE: 94

His Thr Lys Ile His Gly Ser Gln Leu Val
1               5                   10

<210> SEQ ID NO 95
<211> LENGTH: 38
<212> TYPE: DNA

<213> ORGANISM: Artificial Sequence
<220> FEATURE:
<223> OTHER INFORMATION: Description of Artificial Sequence: synthetic
      4bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (22)..(33)
<223> OTHER INFORMATION: ZFP target site

<400> SEQUENCE: 95
ctagcattat ccgagttaca caactcggat aatgctag                           38

<210> SEQ ID NO 96
<211> LENGTH: 39
<212> TYPE: DNA
<213> ORGANISM: Artificial Sequence
<220> FEATURE:
<223> OTHER INFORMATION: Description of Artificial Sequence: synthetic
      5bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (23)..(34)
<223> OTHER INFORMATION: ZFP target site

<400> SEQUENCE: 96
ctagcattat ccgagttcac acaactcgga taatgctag                          39

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: synthetic
      6bp separation oligonucleotide
<220> FEATURE:
<221> NAME/KEY: misc_feature
<222> LOCATION: (7)..(18)
<223> OTHER INFORMATION: ZFP target site
<220> FEATURE:
<221> NAME/KEY: misc_feature
<222> LOCATION: (25)..(36)
<223> OTHER INFORMATION: ZFP target site

<400> SEQUENCE: 97
ctaggcatta tccgagttca ccacaactcg gataatgact ag                      42

<210> SEQ ID NO 98
<211> LENGTH: 41
<212> TYPE: DNA
<213> ORGANISM: Artificial Sequence
<220> FEATURE:
<223> OTHER INFORMATION: Description of Artificial Sequence: synthetic
      7bp separation oligonucleotide
<220> FEATURE:
<221> NAME/KEY: misc_feature
<222> LOCATION: (6)..(17)
<223> OTHER INFORMATION: ZFP target sequence
<220> FEATURE:
<221> NAME/KEY: misc_feature
<222> LOCATION: (25)..(36)
<223> OTHER INFORMATION: ZFP target sequence

<400> SEQUENCE: 98
ctagcattat ccgagttcac acacaactcg gataatgcta g                       41

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: synthetic
      8bp separation oligonucleotide
<220> FEATURE:
<221> NAME/KEY: misc_feature
<222> LOCATION: (6)..(17)
<223> OTHER INFORMATION: ZPF target site
<220> FEATURE:
<221> NAME/KEY: misc_feature
<222> LOCATION: (26)..(37)
<223> OTHER INFORMATION: ZPF target site

<400> SEQUENCE: 99
ctagcattat ccgagttcac cacacaactc ggataatgct ag                          42

<210> SEQ ID NO 100
<211> LENGTH: 43
<212> TYPE: DNA
<213> ORGANISM: Artificial Sequence
<220> FEATURE:
<223> OTHER INFORMATION: Description of Artificial Sequence: synthetic
      9bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (27)..(38)
<223> OTHER INFORMATION: ZFP target site

<400> SEQUENCE: 100
ctagcattat ccgagttcac acacacaact cggataatgc tag                         43

<210> SEQ ID NO 101
<211> LENGTH: 46
<212> TYPE: DNA
<213> ORGANISM: Artificial Sequence
<220> FEATURE:
<223> OTHER INFORMATION: Description of Artificial Sequence: synthetic
      12bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (30)..(41)
<223> OTHER INFORMATION: ZFP target site

<400> SEQUENCE: 101
ctagcattat ccgagttcac caccaacaca actcggataa tgctag                      46

<210> SEQ ID NO 102
<211> LENGTH: 49
<212> TYPE: DNA
<213> ORGANISM: Artificial Sequence
<220> FEATURE:
<223> OTHER INFORMATION: Description of Artificial Sequence: synthetic
      15bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (33)..(44)

<223> OTHER INFORMATION: ZFP target site

<400> SEQUENCE: 102
ctagcattat ccgagttcac caccaaccac acaactcgga taatgctag                49

<210> SEQ ID NO 103
<211> LENGTH: 50
<212> TYPE: DNA
<213> ORGANISM: Artificial Sequence
<220> FEATURE:
<223> OTHER INFORMATION: Description of Artificial Sequence: synthetic
      16bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (34)..(45)
<223> OTHER INFORMATION: ZFP target site

<400> SEQUENCE: 103
ctagcattat ccgagttcac caccaaccac accaactcgg ataatgctag                50

<210> SEQ ID NO 104
<211> LENGTH: 51
<212> TYPE: DNA
<213> ORGANISM: Artificial Sequence
<220> FEATURE:
<223> OTHER INFORMATION: Description of Artificial Sequence: synthetic
      17bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (35)..(46)
<223> OTHER INFORMATION: ZFP target site

<400> SEQUENCE: 104
ctagcattat ccgagttcaa ccaccaacca caccaactcg gataatgcta g                51

<210> SEQ ID NO 105
<211> LENGTH: 56
<212> TYPE: DNA
<213> ORGANISM: Artificial Sequence
<220> FEATURE:
<223> OTHER INFORMATION: Description of Artificial Sequence: synthetic
      22bp separation oligonucleotide
<220> FEATURE:
<221> NAME/KEY: misc_feature
<222> LOCATION: (6)..(17)
<223> OTHER INFORMATION: ZFP target site
<220> FEATURE:
<221> NAME/KEY: misc_feature
<222> LOCATION: (40)..(51)
<223> OTHER INFORMATION: ZFP target site

<400> SEQUENCE: 105
ctagcattat ccgagttcaa ccaccaacca caccaacaca actcggataa tgctag                56

<210> SEQ ID NO 106
<211> LENGTH: 60
<212> TYPE: DNA
<213> ORGANISM: Artificial Sequence
<220> FEATURE:
<223> OTHER INFORMATION: Description of Artificial Sequence: synthetic
      26bp separation oligonucleotide
<220> FEATURE:
<221> NAME/KEY: misc_feature

```
<222> LOCATION: (6)..(17)
<223> OTHER INFORMATION: ZFP target site
<220> FEATURE:
<221> NAME/KEY: misc_feature
<222> LOCATION: (44)..(55)
<223> OTHER INFORMATION: ZFP target site

<400> SEQUENCE: 106
ctagcattat ccgagttcaa ccaccaacca caccaacacc accaactcgg ataatgctag    60

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 107

Leu Arg Gly Ser
1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 108

Leu Gly Gly Ser
1

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 109

Thr Gly Gly Ser
1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 110

Gly Gly Gly Ser
1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 111

Leu Pro Gly Ser
```

<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 112

Leu Arg Lys Ser
1

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: synthetic
      linker

<400> SEQUENCE: 113

Leu Arg Trp Ser
1

<210> SEQ ID NO 114
<211> LENGTH: 12
<212> TYPE: DNA
<213> ORGANISM: Artificial Sequence
<220> FEATURE:
<223> OTHER INFORMATION: Description of Artificial Sequence: synthetic
      IL2Rgamma Gene fusion 5-8 target sequence

<400> SEQUENCE: 114
actctgtgga ag                                                           12

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene fusion 5-8 F1 peptide

<400> SEQUENCE: 115

Arg Ser Asp Asn Leu Ser Glu
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: synthetic I
      L2Rgamma Gene fusion 5-8 F2 peptide

<400> SEQUENCE: 116

Arg Asn Ala His Arg Ile Asn
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene fusion 5-8 F3 peptide

<400> SEQUENCE: 117

Arg Ser Asp Thr Leu Ser Glu
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene Fusion 5-8 F4 peptide

<400> SEQUENCE: 118

Ala Arg Ser Thr Arg Thr Thr
1               5

<210> SEQ ID NO 119
<211> LENGTH: 13
<212> TYPE: DNA
<213> ORGANISM: Artificial Sequence
<220> FEATURE:
<223> OTHER INFORMATION: Description of Artificial Sequence: synthetic
      IL2Rgamma Gene fusion 5-10 target sequence

<400> SEQUENCE: 119
aacacgaaac gtg                                                        13

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene fusion 5-10 F1 peptide

<400> SEQUENCE: 120

Arg Ser Asp Ser Leu Ser Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene Fusion 5-10 F2 peptide

<400> SEQUENCE: 121

Asp Ser Ser Asn Arg Lys Thr
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene Fusion 5-10 F3 peptide

<400> SEQUENCE: 122

Arg Ser Asp Ser Leu Ser Val
1               5

<210> SEQ ID NO 123
<211> LENGTH: 7
<212> TYPE: PRT

<213> ORGANISM: Artificial Sequence
<220> FEATURE:
<223> OTHER INFORMATION: Description of Artificial Sequence: synthetic
    IL2Rgamma Gene Fusion 5-10 F4 peptide

<400> SEQUENCE: 123

Asp Arg Ser Asn Arg Ile Thr
1               5

<210> SEQ ID NO 124
<211> LENGTH: 8
<212> TYPE: DNA
<213> ORGANISM: Artificial Sequence
<220> FEATURE:
<223> OTHER INFORMATION: Description of Artificial Sequence: synthetic
    replaced sequence

<400> SEQUENCE: 124 gaccacat                                                              8

<210> SEQ ID NO 125
<211> LENGTH: 6
<212> TYPE: DNA
<213> ORGANISM: Artificial Sequence
<220> FEATURE:
<223> OTHER INFORMATION: Description of Artificial Sequence: synthetic
    replacing sequence

<400> SEQUENCE: 125 taacac                                                                6

<210> SEQ ID NO 126
<211> LENGTH: 17
<212> TYPE: DNA
<213> ORGANISM: Artificial Sequence
<220> FEATURE:
<223> OTHER INFORMATION: Description of Artificial Sequence: synthetic
    GFP-Bam oligonucleotide

<400> SEQUENCE: 126
cgaattctgc agtcgac                                                   17

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: synthetic
    GFP-Xba oligonucleotide

<400> SEQUENCE: 127
gattatgatc tagagtcg                                                  18

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: synthetic
    stop sense2 oligonucleotide

<400> SEQUENCE: 128
agccgctacc cctaacacga agcag                                          25

<210> SEQ ID NO 129
<211> LENGTH: 25
<212> TYPE: DNA

```
<213> ORGANISM: Artificial Sequence
<220> FEATURE:
<223> OTHER INFORMATION: Description of Artificial Sequence: synthetic
      stop anti2 oligonucleotide

<400> SEQUENCE: 129
ctgcttcgtg ttaggggtag cggct                                            25

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: synthetic
      287A F1 peptide

<400> SEQUENCE: 130

Arg Ser Asp Asp Leu Thr Arg
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: synthetic
      287A F2 peptide

<400> SEQUENCE: 131

Gln Ser Gly Ala Leu Ala Arg
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: synthetic
      287A F3 peptide

<400> SEQUENCE: 132

Arg Ser Asp His Leu Ser Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: synthetic
      296S F1 peptide

<400> SEQUENCE: 133

Gln Ser Gly Ser Leu Thr Arg
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: synthetic
      296S F2 peptide

<400> SEQUENCE: 134

Gln Ser Gly Asp Leu Thr Arg
1               5
```

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: synthetic
      296S F3 peptide

<400> SEQUENCE: 135

Gln Ser Gly Asn Leu Ala Arg
1               5

<210> SEQ ID NO 136
<211> LENGTH: 10
<212> TYPE: DNA
<213> ORGANISM: Artificial Sequence
<220> FEATURE:
<223> OTHER INFORMATION: Description of Artificial Sequence: synthetic
      287A target sequence

<400> SEQUENCE: 136
ggggtagcgg                                                          10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: synthetic
      287A F1 peptide

<400> SEQUENCE: 137

Arg Ser Asp Asp Leu Thr Arg
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: synthetic
      287A F2 peptide

<400> SEQUENCE: 138

Gln Ser Gly Ala Leu Ala Arg
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: synthetic
      287A F3 peptide

<400> SEQUENCE: 139

Arg Ser Asp His Leu Ser Arg
1               5

<210> SEQ ID NO 140
<211> LENGTH: 9
<212> TYPE: DNA
<213> ORGANISM: Artificial Sequence
<220> FEATURE:
<223> OTHER INFORMATION: Description of Artificial Sequence: synthetic
      296S target sequence

<400> SEQUENCE: 140

-continued

```
gaagcagca                                                                9
```

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: synthetic
      296S F1 peptide <400> SEQUENCE: 141

Gln Ser Gly Ser Leu Thr Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: synthetic
      296S F2 peptide <400> SEQUENCE: 142

Gln Ser Gly Asp Leu Thr Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: synthetic
      296S F3 peptide <400> SEQUENCE: 143

Gln Ser Gly Asn Leu Ala Arg
1               5

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: synthetic
      eGFP primer 1 (5T)

<400> SEQUENCE: 144

```
ctgctgcccg acaacca                                                      17
```

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: synthetic
      eGFP primer 2 (3T)

<400> SEQUENCE: 145

```
ccatgtgatc gcgcttctc                                                    19
```

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: synthetic
      eGFP probe

<400> SEQUENCE: 146
cccagtccgc cctgagcaaa ga          22

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: synthetic
      GAPDH primer 1

<400> SEQUENCE: 147
ccatgttcgt catgggtgtg a          21

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: synthetic
      GAPDH primer 2

<400> SEQUENCE: 148
catggactgt ggtcatgagt          20

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: synthetic
      GAPDH probe

<400> SEQUENCE: 149
tcctgcacca ccaactgctt agca          24

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: synthetic
      GFPnostart oligonucleotide

<400> SEQUENCE: 150
ggcgaggagc tgttcac          17

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: synthetic
      GFP-Xba oligonucleotide

<400> SEQUENCE: 151
gattatgatc tagagtcg          18

<210> SEQ ID NO 152
<211> LENGTH: 12
<212> TYPE: DNA
<213> ORGANISM: Artificial Sequence
<220> FEATURE:
<223> OTHER INFORMATION: Description of Artificial Sequence: synthetic
      IL2Rgamma Gene Target sequence -continued

<400> SEQUENCE: 152
actctgtgga ag                                                          12

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F1 peptide

<400> SEQUENCE: 153

Arg Ser Asp Asn Leu Ser Val
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 154

Arg Asn Ala His Arg Ile Asn
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F3 peptide

<400> SEQUENCE: 155

Arg Ser Asp Thr Leu Ser Glu
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F4 peptide

<400> SEQUENCE: 156

Ala Arg Ser Thr Arg Thr Asn
1               5

<210> SEQ ID NO 157
<211> LENGTH: 12
<212> TYPE: DNA
<213> ORGANISM: Artificial Sequence
<220> FEATURE:
<223> OTHER INFORMATION: Description of Artificial Sequence: synthetic
      IL2Rgamma Gene Target sequence

<400> SEQUENCE: 157
aaagcggctc cg                                                          12

<210> SEQ ID NO 158
<211> LENGTH: 7
<212> TYPE: PRT
<213> ORGANISM: Artificial Sequence
<220> FEATURE:

```
<223> OTHER INFORMATION: Description of Artificial Sequence: synthetic
      IL2Rgamma Gene F1 peptide

<400> SEQUENCE: 158

Arg Ser Asp Thr Leu Ser Glu
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F2 peptide

<400> SEQUENCE: 159

Ala Arg Ser Thr Arg Thr Thr
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F3 peptide

<400> SEQUENCE: 160

Arg Ser Asp Ser Leu Ser Lys
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: synthetic
      IL2Rgamma Gene F4 peptide

<400> SEQUENCE: 161

Gln Arg Ser Asn Leu Lys Val
1               5

<210> SEQ ID NO 162
<211> LENGTH: 117
<212> TYPE: PRT
<213> ORGANISM: Artificial Sequence
<220> FEATURE:
<223> OTHER INFORMATION: Description of Artificial Sequence: synthetic
      nuclease polypeptide

<400> SEQUENCE: 162

Met Ala Glu Arg Pro Phe Gln Cys Arg Ile Cys Met Arg Asn Phe Ser
1               5                   10                  15

Arg Ser Asp Asn Leu Ser Val His Ile Arg Thr His Thr Gly Glu Lys
            20                  25                  30

Pro Phe Ala Cys Asp Ile Cys Gly Arg Lys Phe Ala Arg Asn Ala His
        35                  40                  45

Arg Ile Asn His Thr Lys Ile His Thr Gly Ser Gln Lys Pro Phe Gln
    50                  55                  60

Cys Arg Ile Cys Met Arg Asn Phe Ser Arg Ser Asp Thr Leu Ser Glu
65                  70                  75                  80

His Ile Arg Thr His Thr Gly Glu Lys Pro Phe Ala Cys Asp Ile Cys
                85                  90                  95
```

-continued

```
Gly Arg Lys Phe Ala Ala Arg Ser Thr Arg Thr Asn His Thr Lys Ile
            100                 105                 110

His Leu Arg Gly Ser
        115

<210> SEQ ID NO 163
<211> LENGTH: 117
<212> TYPE: PRT
<213> ORGANISM: Artificial Sequence
<220> FEATURE:
<223> OTHER INFORMATION: Description of Artificial Sequence: synthetic
      nuclease polypeptide

<400> SEQUENCE: 163

Met Ala Glu Arg Pro Phe Gln Cys Arg Ile Cys Met Arg Asn Phe Ser
1               5                   10                  15

Arg Ser Asp Thr Leu Ser Glu His Ile Arg Thr His Thr Gly Glu Lys
            20                  25                  30

Pro Phe Ala Cys Asp Ile Cys Gly Arg Lys Phe Ala Ala Arg Ser Thr
        35                  40                  45

Arg Thr Thr His Thr Lys Ile His Thr Gly Ser Gln Lys Pro Phe Gln
    50                  55                  60

Cys Arg Ile Cys Met Arg Asn Phe Ser Arg Ser Asp Ser Leu Ser Lys
65                  70                  75                  80

His Ile Arg Thr His Thr Gly Glu Lys Pro Phe Ala Cys Asp Ile Cys
                85                  90                  95

Gly Arg Lys Phe Ala Gln Arg Ser Asn Leu Lys Val His Thr Lys Ile
            100                 105                 110

His Leu Arg Gly Ser
        115

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: synthetic
      IL-2Rgamma insert peptide

<400> SEQUENCE: 164

Phe Arg Val Arg Ser Arg Phe Asn Pro Leu Cys Gly Ser
1               5                   10

<210> SEQ ID NO 165
<211> LENGTH: 39
<212> TYPE: DNA
<213> ORGANISM: Artificial Sequence
<220> FEATURE:
<223> OTHER INFORMATION: Description of Artificial Sequence: synthetic
      IL-2Rgamma insert sequence

<400> SEQUENCE: 165
tttcgtgttc ggagccggtt taacccgctc tgtggaagt                          39

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: synthetic
      Ex5_1.5detF1 oligonucleotide

<400> SEQUENCE: 166
```

```
gattcaacca gacagataga agg                                           23
```

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: synthetic
      Ex5_1.5detR1 oligonucleotide

<400> SEQUENCE: 167

```
ttactgtctc atcctttact cc                                            22
```

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: synthetic
      Exon 5 forward primer

<400> SEQUENCE: 168

```
gctaaggcca agaaagtagg gctaaag                                       27
```

<210> SEQ ID NO 169
<211> LENGTH: 25
<212> TYPE: DNA
<213> ORGANISM: Artificial Sequence
<220> FEATURE:
<223> OTHER INFORMATION: Description of Artificial Sequence: synthetic
      Exon 5 reverse primer

<400> SEQUENCE: 169

```
ttccttccat caccaaaccc tcttg                                         25
```

<210> SEQ ID NO 170
<211> LENGTH: 27
<212> TYPE: DNA
<213> ORGANISM: Artificial Sequence
<220> FEATURE:
<223> OTHER INFORMATION: Description of Artificial Sequence: synthetic
      ex5_1.5detF3 oligonucleotide

<400> SEQUENCE: 170

```
gctaaggcca agaaagtagg gctaaag                                       27
```

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: synthetic
      ex5_1.5detR3 oligonucleotide

<400> SEQUENCE: 171

```
ttccttccat caccaaaccc tcttg                                         25
```

<210> SEQ ID NO 172
<211> LENGTH: 42
<212> TYPE: DNA
<213> ORGANISM: Artificial Sequence
<220> FEATURE:
<223> OTHER INFORMATION: Description of Artificial Sequence: synthetic
      Donor1 oligonucleotide

<400> SEQUENCE: 172

```
cttcagccgc tatccagacc acatgaaaca acacgacttc tt                      42
```

<210> SEQ ID NO 173
<211> LENGTH: 42
<212> TYPE: DNA
<213> ORGANISM: Artificial Sequence
<220> FEATURE:
<223> OTHER INFORMATION: Description of Artificial Sequence: synthetic
      Donor2 oligonucleotide

<400> SEQUENCE: 173
cttcagccgg tatccagacc acatgaaaca acatgacttc tt                          42

<210> SEQ ID NO 174
<211> LENGTH: 42
<212> TYPE: DNA
<213> ORGANISM: Artificial Sequence
<220> FEATURE:
<223> OTHER INFORMATION: Description of Artificial Sequence: synthetic
      Donor3 oligonucleotide

<400> SEQUENCE: 174
cttcagccgc tacccagacc acatgaaaca gcacgacttc tt                          42

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: synthetic
      Donor 5 oligonucleotide

<400> SEQUENCE: 175
cttcagccgc taccccgacc acatgaagca gcacgacttc tt                          42

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: synthetic
      GFP mut oligonucleotide

<400> SEQUENCE: 176
cttcagccgc tacccctaac acgaagcagc acgacttctt                             40

<210> SEQ ID NO 177
<211> LENGTH: 42
<212> TYPE: DNA
<213> ORGANISM: Artificial Sequence
<220> FEATURE:
<223> OTHER INFORMATION: Description of Artificial Sequence: synthetic
      GFP oligonucleotide

<400> SEQUENCE: 177
cttcagccgc taccccgacc acatgaagca gcacgacttc tt                          42

<210> SEQ ID NO 178
<211> LENGTH: 12
<212> TYPE: DNA
<213> ORGANISM: Artificial Sequence
<220> FEATURE:
<223> OTHER INFORMATION: Description of Artificial Sequence: synthetic
      sca-36a oligonucleotide

<400> SEQUENCE: 178
gaagtctgcc gt                                                           12

<210> SEQ ID NO 179
<211> LENGTH: 13
<212> TYPE: DNA
<213> ORGANISM: Artificial Sequence
<220> FEATURE:
<223> OTHER INFORMATION: Description of Artificial Sequence: synthetic
      sca-36b oligonucleotide

<400> SEQUENCE: 179
gaagtctgcc gtt                                                          13

<210> SEQ ID NO 180
<211> LENGTH: 13
<212> TYPE: DNA
<213> ORGANISM: Artificial Sequence
<220> FEATURE:
<223> OTHER INFORMATION: Description of Artificial Sequence: synthetic
      sca-36c oligonucleotide

<400> SEQUENCE: 180
gaagtctgcc gtt                                                          13

<210> SEQ ID NO 181
<211> LENGTH: 52
<212> TYPE: DNA
<213> ORGANISM: Artificial Sequence
<220> FEATURE:
<223> OTHER INFORMATION: Description of Artificial Sequence: synthetic
      beta-globin oligonucleotide

<400> SEQUENCE: 181
caaacagaca ccatggtgca tctgactcct gtggagaagt ctgccgttac tg               52

<210> SEQ ID NO 182
<211> LENGTH: 13
<212> TYPE: DNA
<213> ORGANISM: Artificial Sequence
<220> FEATURE:
<223> OTHER INFORMATION: Description of Artificial Sequence: synthetic
      sca-r29b oligonucleotide

<400> SEQUENCE: 182
acgtagactg agg                                                          13

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: synthetic
      non-canonical inter-finger linker

<400> SEQUENCE: 183

Thr Gly Gly Gly Gly Ser Gln Lys Pro
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: synthetic
      sca-r29b F1 peptide

<400> SEQUENCE: 184

Gln Ser Gly Asp Leu Thr Arg
1               5

```
<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: synthetic
      sca-r29b F2 peptide

<400> SEQUENCE: 185

Thr Ser Ala Asn Leu Ser Arg
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: synthetic
      sca-r29b F3 peptide

<400> SEQUENCE: 186

Asp Arg Ser Ala Leu Ser Arg
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: synthetic
      sca-r29b F4 peptide

<400> SEQUENCE: 187

Gln Ser Gly His Leu Ser Arg
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36a F1 peptide

<400> SEQUENCE: 188

Arg Ser Gln Thr Arg Lys Thr
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36a F2 peptide

<400> SEQUENCE: 189

Gln Lys Arg Asn Arg Thr Lys
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36a F3 peptide
```

<400> SEQUENCE: 190

Asp Arg Ser Ala Leu Ser Arg
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36a F4 peptide

<400> SEQUENCE: 191

Gln Ser Gly Asn Leu Ala Arg
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36b F1 peptide

<400> SEQUENCE: 192

Thr Ser Gly Ser Leu Ser Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36b F2 peptide

<400> SEQUENCE: 193

Asp Arg Ser Asp Leu Ser Arg
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36b F3 peptide

<400> SEQUENCE: 194

Asp Arg Ser Ala Leu Ser Arg
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36b F4 peptide

<400> SEQUENCE: 195

Gln Ser Gly Asn Leu Ala Arg
1               5

<210> SEQ ID NO 196
<211> LENGTH: 7

```
<212> TYPE: PRT
<213> ORGANISM: Artificial Sequence
<220> FEATURE:
<223> OTHER INFORMATION: Description of Artificial Sequence: synthetic
      sca-36c F1 peptide

<400> SEQUENCE: 196

Thr Ser Ser Ser Leu Ser Arg
1               5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36c F2 peptide

<400> SEQUENCE: 197

Asp Arg Ser Asp Leu Ser Arg
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36c F3 peptide

<400> SEQUENCE: 198

Asp Arg Ser Ala Leu Ser Arg
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: synthetic
      sca-36c F4 peptide

<400> SEQUENCE: 199

Gln Ser Gly Asn Leu Ala Arg
1               5

<210> SEQ ID NO 200
<211> LENGTH: 55
<212> TYPE: DNA
<213> ORGANISM: Artificial Sequence
<220> FEATURE:
<223> OTHER INFORMATION: Description of Artificial Sequence: synthetic
      beta-globin gene sequence targeted by the ZFNs

<400> SEQUENCE: 200
ctagacacca tggtgcatct gactcctgtg gagaagtctg ccgttactgc cctag          55
```

METHODS AND COMPOSITIONS FOR TARGETED CLEAVAGE AND RECOMBINATION

CROSS-REFERENCE TO RELATED APPLICATIONS

This application is a continuation of U.S. patent application Ser. No. 13/837,027, filed Mar. 15, 2013, which is a continuation of U.S. patent application Ser. No. 12/804,234, filed Jul. 16, 2010, now U.S. Pat. No. 8,524,500, which is a continuation of U.S. patent application Ser. No. 10/912,932 filed Aug. 6, 2004, now U.S. Pat. No. 7,888,121, which claims the benefit of the following U.S. provisional patent applications: 60/493,931 filed Aug. 8, 2003; 60/518,253 filed Nov. 7, 2003; 60/530,541 filed Dec. 18, 2003; 60/542,780 filed Feb. 5, 2004; 60/556,831 filed Mar. 26, 2004 and 60/575,919 filed Jun. 1, 2004; the disclosures of which are incorporated by reference in their entireties for all purposes.

SEQUENCE LISTING

The instant application contains a Sequence Listing which has been submitted in ASCII format via EFS-Web and is hereby incorporated by reference in its entirety. Said ASCII copy, created on Aug. 25, 2014, is named 8325003604_SL.txt and is 70,199 bytes in size.

STATEMENT OF RIGHTS TO INVENTIONS MADE UNDER FEDERALLY SPONSORED RESEARCH

Not applicable.

TECHNICAL FIELD

The present disclosure is in the field of genome engineering and homologous recombination.

BACKGROUND

A major area of interest in genome biology, especially in light of the determination of the complete nucleotide sequences of a number of genomes, is the targeted alteration of genome sequences. To provide but one example, sickle cell anemia is caused by mutation of a single nucleotide pair in the human β-globin gene. Thus, the ability to convert the endogenous genomic copy of this mutant nucleotide pair to the wild-type sequence in a stable fashion and produce normal β-globin would provide a cure for sickle cell anemia.

Attempts have been made to alter genomic sequences in cultured cells by taking advantage of the natural phenomenon of homologous recombination. See, for example, Capecchi (1989) *Science* 244:1288-1292; U.S. Pat. Nos. 6,528,313 and 6,528,314. If a polynucleotide has sufficient homology to the genomic region containing the sequence to be altered, it is possible for part or all of the sequence of the polynucleotide to replace the genomic sequence by homologous recombination. However, the frequency of homologous recombination under these circumstances is extremely low. Moreover, the frequency of insertion of the exogenous polynucleotide at genomic locations that lack sequence homology exceeds the frequency of homologous recombination by several orders of magnitude.

The introduction of a double-stranded break into genomic DNA, in the region of the genome bearing homology to an exogenous polynucleotide, has been shown to stimulate homologous recombination at this site by several thousand-fold in cultured cells. Rouet et al. (1994) *Mol. Cell. Biol.* 14:8096-8106; Choulika et al. (1995) *Mol. Cell. Biol.* 15:1968-1973; Donoho et al. (1998) *Mol. Cell. Biol.* 18:4070-4078. See also Johnson et al. (2001) *Biochem. Soc. Trans.* 29:196-201; and Yanez et al. (1998) *Gene Therapy* 5:149-159. In these methods, DNA cleavage in the desired genomic region was accomplished by inserting a recognition site for a meganuclease (i.e., an endonuclease whose recognition sequence is so large that it does not occur, or occurs only rarely, in the genome of interest) into the desired genomic region.

However, meganuclease cleavage-stimulated homologous recombination relies on either the fortuitous presence of, or the directed insertion of, a suitable meganuclease recognition site in the vicinity of the genomic region to be altered. Since meganuclease recognition sites are rare (or nonexistent) in a typical mammalian genome, and insertion of a suitable meganuclease recognition site is plagued with the same difficulties as associated with other genomic alterations, these methods are not broadly applicable.

Thus, there remains a need for compositions and methods for targeted alteration of sequences in any genome.

SUMMARY

The present disclosure provides compositions and methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof. Compositions include fusion polypeptides comprising an engineered zinc finger binding domain (e.g., a zinc finger binding domain having a novel specificity) and a cleavage domain, and fusion polypeptides comprising an engineered zinc finger binding domain and a cleavage half-domain. Cleavage domains and cleavage half domains can be obtained, for example, from various restriction endonucleases and/or homing endonucleases.

Cellular chromatin can be present in any type of cell including, but not limited to, prokaryotic and eukaryotic cells, fungal cells, plant cells, animal cells, mammalian cells, primate cells and human cells.

In one aspect, a method for cleavage of cellular chromatin in a region of interest (e.g., a method for targeted cleavage of genomic sequences) is provided, the method comprising: (a) selecting a first sequence in the region of interest; (b) engineering a first zinc finger binding domain to bind to the first sequence; and (c) expressing a first fusion protein in the cell, the first fusion protein comprising the first engineered zinc finger binding domain and a cleavage domain; wherein the first fusion protein binds to the first sequence and the cellular chromatin is cleaved in the region of interest. The site of cleavage can be coincident with the sequence to which the fusion protein binds, or it can be adjacent (e.g., separated from the near edge of the binding site by 1, 2, 3, 4, 5, 6, 7, 8, 9, 10, 11, 12, 13, 14, 15 or more nucleotides). A fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

In certain embodiments, the cleavage domain may comprise two cleavage half-domains that are covalently linked in the same polypeptide. The two cleavage half-domains can be derived from the same endonuclease or from different endonucleases.

In additional embodiments, targeted cleavage of cellular chromatin in a region of interest is achieved by expressing two fusion proteins in a cell, each fusion protein comprising a zinc finger binding domain and a cleavage half-domain. One or both of the zinc finger binding domains of the fusion proteins can be engineered to bind to a target sequence in the vicinity of the intended cleavage site. If expression of the fusion proteins is by polynucleotide delivery, each of the two fusion proteins can be encoded by a separate polynucleotide, or a single polynucleotide can encode both fusion proteins.

Accordingly, a method for cleaving cellular chromatin in a region of interest can comprise (a) selecting a first sequence in the region of interest; (b) engineering a first zinc finger binding domain to bind to the first sequence; (c) expressing a first fusion protein in the cell, the first fusion protein comprising the first zinc finger binding domain and a first cleavage half-domain; and (d) expressing a second fusion protein in the cell, the second fusion protein comprising a second zinc finger binding domain and a second cleavage half-domain, wherein the first fusion protein binds to the first sequence, and the second fusion protein binds to a second sequence located between 2 and 50 nucleotides from the first sequence, thereby positioning the cleavage half-domains such that the cellular chromatin is cleaved in the region of interest.

In certain embodiments, binding of the first and second fusion proteins positions the cleavage half-domains such that a functional cleavage domain is reconstituted.

In certain embodiments, the second zinc finger binding domain is engineered to bind to the second sequence. In further embodiments, the first and second cleavage half-domains are derived from the same endonuclease, which can be, for example, a restriction endonuclease (e.g., a Type IIS restriction endonuclease such as Fok I) or a homing endonuclease.

In other embodiments, any of the methods described herein may comprise (a) selecting first and second sequences in a region of interest, wherein the first and second sequences are between 2 and 50 nucleotides apart; (b) engineering a first zinc finger binding domain to bind to the first sequence; (c) engineering a second zinc finger binding domain to bind to the second sequence; (d) expressing a first fusion protein in the cell, the first fusion protein comprising the first engineered zinc finger binding domain and a first cleavage half-domain; (e) expressing a second fusion protein in the cell, the second fusion protein comprising the second engineered zinc finger binding domain and a second cleavage half-domain; wherein the first fusion protein binds to the first sequence and the second fusion protein binds to the second sequence, thereby positioning the first and second cleavage half-domains such that the cellular chromatin is cleaved in the region of interest.

In certain embodiments, the first and second cleavage half-domains are derived from the same endonuclease, for example, a Type IIS restriction endonuclease, for example, Fok I. In additional embodiments, cellular chromatin is cleaved at one or more sites between the first and second sequences to which the fusion proteins bind.

In further embodiments, a method for cleavage of cellular chromatin in a region of interest comprises (a) selecting the region of interest; (b) engineering a first zinc finger binding domain to bind to a first sequence in the region of interest; (c) providing a second zinc finger binding domain which binds to a second sequence in the region of interest, wherein the second sequence is located between 2 and 50 nucleotides from the first sequence; (d) expressing a first fusion protein in the cell, the first fusion protein comprising the first zinc finger binding domain and a first cleavage half-domain; and (e) expressing a second fusion protein in the cell, the second fusion protein comprising the second zinc finger binding domain and a second cleavage half domain; wherein the first fusion protein binds to the first sequence, and the second fusion protein binds to the second sequence, thereby positioning the cleavage half-domains such that the cellular chromatin is cleaved in the region of interest.

In any of the methods described herein, the first and second cleavage half-domains may be derived from the same endonuclease or from different endonucleases. In additional embodiments, the second zinc finger binding domain is engineered to bind to the second sequence.

If one or more polynucleotides encoding the fusion proteins are introduced into the cell, an exemplary method for targeted cleavage of cellular chromatin in a region of interest comprises (a) selecting the region of interest; (b) engineering a first zinc finger binding domain to bind to a first sequence in the region of interest; (c) providing a second zinc finger binding domain which binds to a second sequence in the region of interest, wherein the second sequence is located between 2 and 50 nucleotides from the first sequence; and (d) contacting a cell with (i) a first polynucleotide encoding a first fusion protein, the fusion protein comprising the first zinc finger binding domain and a first cleavage half-domain, and (ii) a second polynucleotide encoding a second fusion protein, the fusion protein comprising the second zinc finger binding domain and a second cleavage half domain; wherein the first and second fusion proteins are expressed, the first fusion protein binds to the first sequence and the second fusion protein binds to the second sequence, thereby positioning the cleavage half-domains such that the cellular chromatin is cleaved in the region of interest. In a variation of this method, a cell is contacted with a single polynucleotide which encodes both fusion proteins.

For any of the aforementioned methods, the cellular chromatin can be in a chromosome, episome or organellar genome. In addition, in any of the methods described herein, at least one zinc finger binding domain is engineered, for example by design or selection methods.

Similarly, for any of the aforementioned methods, the cleavage half domain can be derived from, for example, a homing endonuclease or a restriction endonuclease, for example, a Type IIS restriction endonuclease. An exemplary Type IIS restriction endonuclease is Fok I.

For any of the methods of targeted cleavage, targeted mutagenesis and/or targeted recombination disclosed herein utilizing fusion proteins comprising a cleavage half-domain, the near edges of the binding sites of the fusion proteins can be separated by 5 or 6 base pairs. In these embodiments, the binding domain and the cleavage domain of the fusion proteins can be separated by a linker of 4 amino acid residues.

In certain embodiments, it is possible to obtain increased cleavage specificity by utilizing fusion proteins in which one or both cleavage half-domains contains an alteration in the amino acid sequence of the dimerization interface.

Targeted mutagenesis of a region of interest in cellular chromatin can occur when a targeted cleavage event, as describe above, is followed by non-homologous end joining (NHEJ). Accordingly, methods for alteration of a first nucleotide sequence in a region of interest in cellular chromatin are provided, wherein the methods comprise the steps of (a) engineering a first zinc finger binding domain to bind to a second nucleotide sequence in the region of interest, wherein the second sequence comprises at least 9 nucleotides; (b) providing a second zinc finger binding domain to bind to a third nucleotide sequence, wherein the third sequence comprises at least 9 nucleotides and is located between 2 and 50 nucleotides from the second sequence; (c) expressing a first fusion protein in the cell, the first fusion protein comprising the first zinc finger binding domain and a first cleavage half-domain; and (d) expressing a second fusion protein in the cell, the second fusion protein comprising the second zinc finger binding domain and a second cleavage half domain; wherein the first fusion protein binds to the second sequence, and the second fusion protein binds to the third sequence, thereby positioning the cleavage half-domains such that the cellular chromatin is cleaved in the region of interest and the cleavage site is subjected to non-homologous end joining.

Targeted mutations resulting from the aforementioned method include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

Methods for targeted recombination (for, e.g., alteration or replacement of a sequence in a chromosome or a region of interest in cellular chromatin) are also provided. For example, a mutant genomic sequence can be replaced by a wild-type sequence, e.g., for treatment of genetic disease or inherited disorders. In addition, a wild-type genomic sequence can be replaced by a mutant sequence, e.g., to prevent function of an oncogene product or a product of a gene involved in an inappropriate inflammatory response. Furthermore, one allele of a gene can be replaced by a different allele.

In such methods, one or more targeted nucleases create a double-stranded break in cellular chromatin at a predetermined site, and a donor polynucleotide, having homology to the nucleotide sequence of the cellular chromatin in the region of the break, is introduced into the cell. Cellular DNA repair processes are activated by the presence of the double-stranded break and the donor polynucleotide is used as a template for repair of the break, resulting in the introduction of all or part of the nucleotide sequence of the donor into the cellular chromatin. Thus a first sequence in cellular chromatin can be altered and, in certain embodiments, can be converted into a sequence present in a donor polynucleotide.

In this context, the use of the terms "replace" or "replacement" can be understood to represent replacement of one nucleotide sequence by another, (i.e., replacement of a sequence in the informational sense), and does not necessarily require physical or chemical replacement of one polynucleotide by another.

Accordingly, in one aspect, a method for replacement of a region of interest in cellular chromatin (e.g., a genomic sequence) with a first nucleotide sequence is provided, the method comprising: (a) engineering a zinc finger binding domain to bind to a second sequence in the region of interest; (b) expressing a fusion protein in a cell, the fusion protein comprising the zinc finger binding domain and a cleavage domain; and (c) contacting the cell with a polynucleotide comprising the first nucleotide sequence; wherein the fusion protein binds to the second sequence such that the cellular chromatin is cleaved in the region of interest and a nucleotide sequence in the region of interest is replaced with the first nucleotide sequence. Generally, cellular chromatin is cleaved in the region of interest at or adjacent to the second sequence. In further embodiments, the cleavage domain comprises two cleavage half-domains, which can be derived from the same or from different nucleases.

In addition, a method for replacement of a region of interest in cellular chromatin (e.g., a genomic sequence) with a first nucleotide sequence is provided, the method comprising: (a) engineering a first zinc finger binding domain to bind to a second sequence in the region of interest; (b) providing a second zinc finger binding domain to bind to a third sequence in the region of interest; (c) expressing a first fusion protein in a cell, the first fusion protein comprising the first zinc finger binding domain and a first cleavage half-domain; (d) expressing a second fusion protein in the cell, the second fusion protein comprising the second zinc finger binding domain and a second cleavage half-domain; and (e) contacting the cell with a polynucleotide comprising the first nucleotide sequence; wherein the first fusion protein binds to the second sequence and the second fusion protein binds to the third sequence, thereby positioning the cleavage half-domains such that the cellular chromatin is cleaved in the region of interest and a nucleotide sequence in the region of interest is replaced with the first nucleotide sequence. Generally, cellular chromatin is cleaved in the region of interest at a site between the second and third sequences.

Additional methods for replacement of a region of interest in cellular chromatin (e.g., a genomic sequence) with a first nucleotide sequence comprise: (a) selecting a second sequence, wherein the second sequence is in the region of interest and has a length of at least 9 nucleotides; (b) engineering a first zinc finger binding domain to bind to the second sequence; (c) selecting a third sequence, wherein the third sequence has a length of at least 9 nucleotides and is located between 2 and 50 nucleotides from the second sequence; (d) providing a second zinc finger binding domain to bind to the third sequence; (e) expressing a first fusion protein in a cell, the first fusion protein comprising the first zinc finger binding domain and a first cleavage half-domain; (f) expressing a second fusion protein in the cell, the second fusion protein comprising the second zinc finger binding domain and a second cleavage half-domain; and (g) contacting the cell with a polynucleotide comprising the first nucleotide sequence; wherein the first fusion protein binds to the second sequence and the second fusion protein binds to the third sequence, thereby positioning the cleavage half-domains such that the cellular chromatin is cleaved in the region of interest and a nucleotide sequence in the region of interest is replaced with the first nucleotide sequence. Generally, cellular chromatin is cleaved in the region of interest at a site between the second and third sequences.

In another aspect, methods for targeted recombination are provided in which, a first nucleotide sequence, located in a region of interest in cellular chromatin, is replaced with a second nucleotide sequence. The methods comprise (a) engineering a first zinc finger binding domain to bind to a third sequence in the region of interest; (b) providing a second zinc finger binding domain to bind to a fourth sequence; (c) expressing a first fusion protein in a cell, the fusion protein comprising the first zinc finger binding domain and a first cleavage half-domain; (d) expressing a second fusion protein in the cell, the second fusion protein comprising the second zinc finger binding domain and a second cleavage half-domain; and (e) contacting a cell with a polynucleotide comprising the second nucleotide sequence; wherein the first fusion protein binds to the fourth sequence and the second fusion protein binds to the fourth sequence, thereby positioning the cleavage half-domains such that the cellular chromatin is cleaved in the region of interest and the first nucleotide sequence is replaced with the second nucleotide sequence.

In additional embodiments, a method for alteration of a first nucleotide sequence in a region of interest in cellular chromatin is provided, the method comprising the steps of (a) engineering a first zinc finger binding domain to bind to a second nucleotide sequence in the region of interest, wherein the second sequence comprises at least 9 nucleotides; (b) providing a second zinc finger binding domain to bind to a third nucleotide sequence, wherein the third sequence comprises at least 9 nucleotides and is located between 2 and 50 nucleotides from the second sequence; (c) expressing a first fusion protein in the cell, the first fusion protein comprising the first zinc finger binding domain and a first cleavage half-domain; (d) expressing a second fusion protein in the cell, the second fusion protein comprising the second zinc finger binding domain and a second cleavage half domain; and (e) contacting the cell with a polynucleotide comprising a fourth nucleotide sequence, wherein the fourth nucleotide sequence is homologous but non-identical with the first nucleotide sequence; wherein the first fusion protein binds to the second sequence, and the second fusion protein binds to the third sequence, thereby positioning the cleavage half-domains such that the cellular chromatin is cleaved in the region of interest and the first nucleotide sequence is altered. In certain embodiments, the first nucleotide sequence is converted to the fourth nucleotide sequence. In additional embodiments, the second and third nucleotide sequences (i.e., the binding sites for the fusion proteins) are present in the polynucleotide comprising the fourth nucleotide sequence (i.e., the donor polynucleotide) and the polynucleotide comprising the fourth nucleotide sequence is cleaved.

In the aforementioned methods for targeted recombination, the binding sites for the fusion proteins (i.e., the third and fourth sequences) can comprise any number of nucleotides. Preferably, they are at least nine nucleotides in length, but they can also be larger (e.g., 10, 11, 12, 13, 14, 15, 16, 17, 18 and up to 100 nucleotides, including any integral value between 9 and 100 nucleotides); moreover the third and fourth sequences need not be the same length. The distance between the binding sites (i.e., the length of nucleotide sequence between the third and fourth sequences) can be any integral number of nucleotide pairs between 2 and 50, (e.g., 5 or 6 base pairs) as measured from the near end of one binding site to the near end of the other binding site.

In the aforementioned methods for targeted recombination, cellular chromatin can be cleaved at a site located between the binding sites of the two fusion proteins. In certain embodiments, the binding sites are on opposite DNA strands. Moreover, expression of the fusion proteins in the cell can be accomplished either by introduction of the proteins into the cell or by introduction of one or more polynucleotides into the cell, which are optionally transcribed (if the polynucleotide is DNA), and the transcript(s) translated, to produce the fusion proteins. For example, two polynucleotides, each comprising sequences encoding one of the two fusion proteins, can be introduced into a cell. Alternatively, a single polynucleotide comprising sequences encoding both fusion proteins can be introduced into the cell.

Thus, in one embodiment, a method for replacement of a region of interest in cellular chromatin (e.g., a genomic sequence) with a first nucleotide sequence comprises: (a) engineering a first zinc finger binding domain to bind to a second sequence in the region of interest; (b) providing a second zinc finger binding domain to bind to a third sequence; and (c) contacting a cell with:

(i) a first polynucleotide comprising the first nucleotide sequence;

(ii) a second polynucleotide encoding a first fusion protein, the first fusion protein comprising the first zinc finger binding domain and a first cleavage half-domain; and (iii) a third polynucleotide encoding a second fusion protein, the second fusion protein comprising the second zinc finger binding domain and a second cleavage half-domain;

wherein the first and second fusion proteins are expressed, the first fusion protein binds to the second sequence and the second fusion protein binds to the third sequence, thereby positioning the cleavage half-domains such that the cellular chromatin is cleaved in the region of interest; and the region of interest is replaced with the first nucleotide sequence.

In the preferred embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present. Double-strand breaks in cellular chromatin can also stimulate cellular mechanisms of non-homologous end joining In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

In methods for targeted recombination and/or replacement and/or alteration of a sequence of interest in cellular chromatin, the first and second cleavage half-domains can be derived from the same endonuclease or from different endonucleases. Endonucleases include, but are not limited to, homing endonucleases and restriction endonucleases. Exemplary restriction endonucleases are Type IIS restriction endonucleases; an exemplary Type IIS restriction endonuclease is Fok I.

The region of interest can be in a chromosome, episome or organellar genome. The region of interest can comprise a mutation, which can replaced by a wild type sequence (or by a different mutant sequence), or the region of interest can contain a wild-type sequence that is replaced by a mutant sequence or a different allele. Mutations include, but are not limited to, point mutations (transitions, transversions), insertions of one or more nucleotide pairs, deletions of one or more nucleotide pairs, rearrangements, inversions and translocations. Mutations can change the coding sequence, introduce premature stop codon(s) and/or modify the frequency of a repetitive sequence motif (e.g., trinucleotide repeat) in a gene. For applications in which targeted recombination is used to replace a mutant sequence, cellular chromatin is generally cleaved at a site located within 100 nucleotides on either side of the mutation, although cleavage sites located up to 6-10 kb from the site of a mutation can also be used.

In any of the methods described herein, the second zinc finger binding domain can be engineered, for example designed and/or selected.

Further, the donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated Virus (AAV). Donor sequences can range in length from 10 to 1,000 nucleotides (or any integral value of nucleotides therebetween) or longer.

Similarly, polynucleotides encoding fusions between a zinc finger binding domain and a cleavage domain or half-domain can be DNA or RNA, can be linear or circular, and can be single-stranded or double-stranded. They can be delivered to the cell as naked nucleic acid, as a complex with one or more delivery agents (e.g., liposomes, poloxamers) or contained in a viral delivery vehicle, such as, for example, an adenovirus or an adeno-associated virus (AAV). A polynucleotide can encode one or more fusion proteins.

In the methods for targeted recombination, as with the methods for targeted cleavage, a cleavage domain or half-domain can derived from any nuclease, e.g., a homing endonuclease or a restriction endonuclease, in particular, a Type IIS restriction endonuclease. Cleavage half-domains can derived from the same or from different endonucleases. An exemplary source, from which a cleavage half-domain can be derived, is the Type IIS restriction endonuclease Fok I.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end joining.

BRIEF DESCRIPTION OF THE DRAWINGS

FIG. 1 shows the nucleotide sequence, in double-stranded form, of a portion of the human hSMC1L1 gene encoding the amino-terminal portion of the protein (SEQ ID NO:1) and the encoded amino acid sequence (SEQ ID NO:2). Target sequences for the hSMC1-specific ZFPs are underlined (one on each DNA strand).

FIG. 3A shows a schematic of a portion of the human X chromosome which includes the hSMC1 gene. FIG. 3B shows a schematic of a portion of the hSMC1 gene including the upstream region (left of +1), the first exon (between +1 and the right end of the arrow labeled "SMC1 coding sequence") and a portion of the first intron. Locations of sequences homologous to the initial amplification primers and to the chromosome-specific primer (see Table 3) are also provided. FIG. 3C shows the nucleotide sequence of the human X chromosome in the region of the SMC1 initiation codon (SEQ ID NO: 3), the encoded amino acid sequence (SEQ ID NO: 4), and the target sites for the SMC1-specific zinc finger proteins. FIG. 3D shows the sequence of the corresponding region of the donor molecule (SEQ ID NO: 5), with differences between donor and chromosomal sequences underlined. Sequences contained in the donor-specific amplification primer (Table 3) are indicated by double underlining.

FIG. 6 shows the nucleotide sequence of an amplification product derived from a mutated hSMC1 gene (SEQ ID NO:6) generated by targeted homologous recombination. Sequences derived from the vector into which the amplification product was cloned are single-underlined, chromosomal sequences not present in the donor molecule are indicated by dashed underlining (nucleotides 32-97), sequences common to the donor and the chromosome are not underlined (nucleotides 98-394 and 402-417), and sequences unique to the donor are double-underlined (nucleotides 395-401). Lower-case letters represent sequences that differ between the chromosome and the donor.

FIG. 7 shows the nucleotide sequence of a portion of the human IL2Rγ gene comprising the 3' end of the second intron and the 5' end of third exon (SEQ ID NO:7) and the amino acid sequence encoded by the displayed portion of the third exon (SEQ ID NO:8). Target sequences for the second pair of IL2Rγ-specific ZFPs are underlined. See Example 2 for details.

FIG. 9A shows a schematic of a portion of the human X chromosome which includes the IL2Rγ gene. FIG. 9B shows a schematic of a portion of the IL2Rγ gene including a portion of the second intron, the third exon and a portion of the third intron. Locations of sequences homologous to the initial amplification primers and to the chromosome-specific primer (see Table 5) are also provided. FIG. 9C shows the nucleotide sequence of the human X chromosome in the region of the third exon of the IL2Rγ gene (SEQ ID NO: 9), the encoded amino acid sequence (SEQ ID NO: 10), and the target sites for the first pair of IL2Rγ-specific zinc finger proteins. FIG. 9D shows the sequence of the corresponding region of the donor molecule (SEQ ID NO: 11), with differences between donor and chromosomal sequences underlined. Sequences contained in the donor-specific amplification primer (Table 5) are indicated by double overlining.

FIG. 12 shows the nucleotide sequence of an amplification product derived from a mutated IL2Rγ gene (SEQ ID NO:12) generated by targeted homologous recombination. Sequences derived from the vector into which the amplification product was cloned are single-underlined, chromosomal sequences not present in the donor molecule are indicated by dashed underlining (nucleotides 460-552), sequences common to the donor and the chromosome are not underlined (nucleotides 32-42 and 59-459), and a stretch of sequence containing nucleotides which distinguish donor sequences from chromosomal sequences is double-underlined (nucleotides 44-58). Lower-case letters represent nucleotides whose sequence differs between the chromosome and the donor.

FIG. 13 shows the nucleotide sequence of a portion of the human beta-globin gene encoding segments of the core promoter, the first two exons and the first intron (SEQ ID NO:13). A missense mutation changing an A (in boldface and underlined) at position 5212541 on Chromosome 11 (BLAT, UCSC Genome Bioinformatics site) to a T results in sickle cell anemia. A first zinc finger/FokI fusion protein was designed such that the primary contacts were with the underlined 12-nucleotide sequence AAGGTGAACGTG (nucleotides 305-316 of SEQ ID NO:13), and a second zinc finger/FokI fusion protein was designed such that the primary contacts were with the complement of the underlined 12-nucleotide sequence CCGTTACTGCCC (nucleotides 325-336 of SEQ ID NO:13).

FIG. 18 shows the nucleotide sequence of an amplification product derived from a mutated beta-globin gene (SEQ ID NO:14) generated by targeted homologous recombination. Chromosomal sequences not present in the donor molecule are indicated by dashed underlining (nucleotides 1-72), sequences common to the donor and the chromosome are not underlined (nucleotides 73-376), and a stretch of sequence containing nucleotides which distinguish donor sequences from chromosomal sequences is double-underlined (nucleotides 377-408). Lower-case letters represent nucleotides whose sequence differs between the chromosome and the donor.

FIG. 19 shows the nucleotide sequence of a portion of the fifth exon of the Interleukin-2 receptor gamma chain (IL-2Rγ) gene (SEQ ID NO:15). Also shown (underlined) are the target sequences for the 5-8 and 5-10 ZFP/FokI fusion proteins. See Example 5 for details.

FIG. 20 shows the amino acid sequence of the 5-8 ZFP/FokI fusion targeted to exon 5 of the human IL-2Rγ gene (SEQ ID NO:16). Amino acid residues 1-17 contain a nuclear localization sequence (NLS, underlined); residues 18-130 contain the ZFP portion, with the recognition regions of the component zinc fingers shown in boldface; the ZFP-FokI linker (ZC linker, underlined) extends from residues 131 to 140 and the FokI cleavage half-domain begins at residue 141 and extends to the end of the protein at residue 336. The residue that was altered to generate the Q486E mutation is shown underlined and in boldface.

FIG. 21 shows the amino acid sequence of the 5-10 ZFP/FokI fusion targeted to exon 5 of the human IL-2Rγ gene (SEQ ID NO:17). Amino acid residues 1-17 contain a nuclear localization sequence (NLS, underlined); residues 18-133 contain the ZFP portion, with the recognition regions of the component zinc fingers shown in boldface; the ZFP-FokI linker (ZC linker, underlined) extends from residues 134 to 143 and the FokI cleavage half-domain begins at residue 144 and extends to the end of the protein at residue 339. The residue that was altered to generate the E490K mutation is shown underlined and in boldface.

FIG. 22 shows the nucleotide sequence of the enhanced Green Fluorescent Protein gene (SEQ ID NO:18) derived from the *Aequorea victoria* GFP gene (Tsien (1998) *Ann. Rev. Biochem.* 67:509-544). The ATG initiation codon, as well as the region which was mutagenized, are underlined.

FIG. 23 shows the nucleotide sequence of a mutant defective eGFP gene (SEQ ID NO:19). Binding sites for ZFP-nucleases are underlined and the region between the binding sites corresponds to the region that was modified.

FIG. 24 shows the structures of plasmids encoding Zinc Finger Nucleases targeted to the eGFP gene.

FIG. 29 shows the nucleotide sequence of the eGFP insert in pCR(R)4-TOPO-GFPdonor5 (SEQ ID NO:20). The insert contains sequences encoding a portion of a non-modified enhanced Green Fluorescent Protein, lacking an initiation codon. See Example 10 for details.

FIG. 32 shows the nucleotide sequence of a 1,527 nucleotide eGFP insert in pCR(R)4-TOPO (SEQ ID NO:21). The sequence encodes a non-modified enhanced Green Fluorescent Protein lacking an initiation codon. See Example 13 for details.

The right panel shows results of an experiment in which CD34[+] cells were transfected with donor DNA containing a BsrBI site and plasmids encoding zinc finger-FokI fusion endonucleases. The relevant genomic region was then amplified and labeled, and the labeled amplification product was digested with BsrBI. "GFP" indicates control cells that were transfected with a GFP-encoding plasmid; "Donor only" indicates control cells that were transfected only with donor DNA, and "ZFP+Donor" indicates cells that were transfected with donor DNA and with plasmids encoding the zinc finger/FokI nucleases. "wt" identifies a band that is diagnostic for chromosomal DNA containing the native IL-2Rγ sequence; "rflp" identifies a band that is diagnostic for chromosomal DNA containing the altered IL-2Rγ sequence present in the donor DNA molecule. The rightmost lane contains DNA size markers. See Example 16 for additional details.

Figure 39:
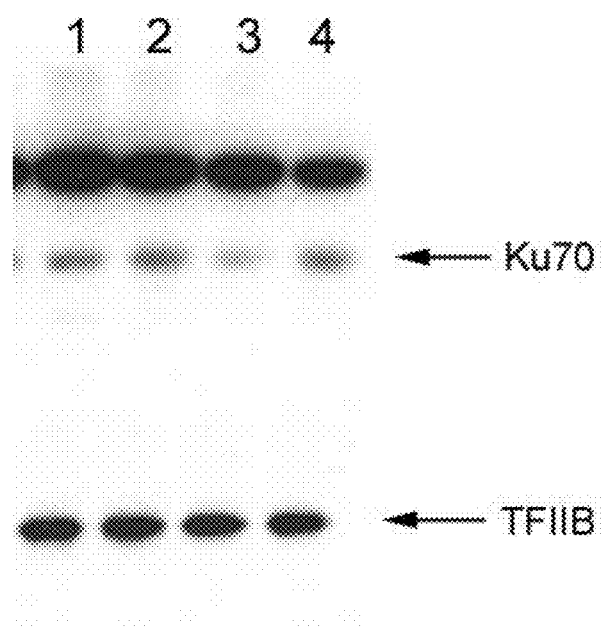

FIG. 39 shows an image of an immunoblot used to test for Ku70 protein levels in cells transfected with Ku70-targeted siRNA. The T7 cell line (Example 9, FIG. 27) was transfected with two concentrations each of siRNA from two different siRNA pools (see Example 18). Lane 1: 70 ng of siRNA pool D; Lane 2: 140 ng of siRNA pool D; Lane 3: 70 ng of siRNA pool E; Lane 4: 140 ng of siRNA pool E. "Ku70" indicates the band representing the Ku70 protein; "TFIIB" indicates a band representing the TFIIB transcription factor, used as a control.

FIG. 40 shows the amino acid sequences of four zinc finger domains targeted to the human β-globin gene: sca-29b (SEQ ID NO:22); sca-36a (SEQ ID NO:23); sca-36b (SEQ ID NO:24) and sca-36c (SEQ ID NO:25). The target site for the sca-29b domain is on one DNA strand, and the target sites for the sca-36a, sca-36b and sca-36c domains are on the opposite strand. See Example 20.

Figure 41:
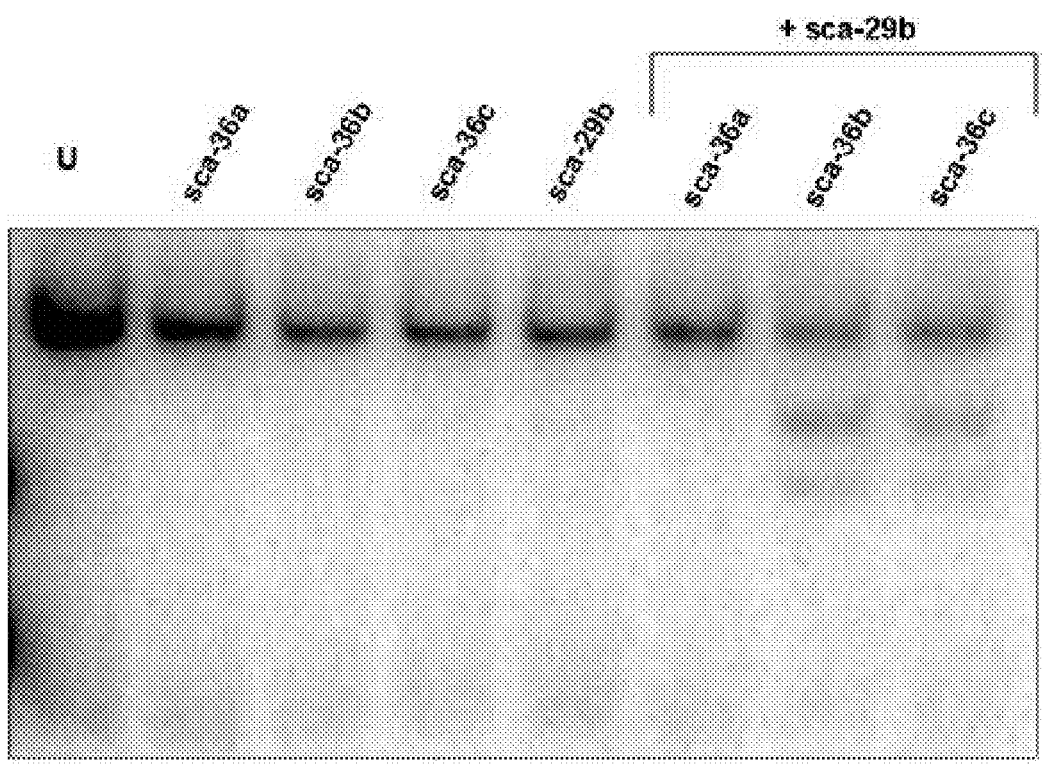

FIG. 41 shows results of an in vitro assay, in which different combinations of zinc finger/FokI fusion nucleases (ZFNs) were tested for sequence-specific DNA cleavage. The lane labeled "U" shows a sample of the DNA template. The next four lanes show results of incubation of the DNA template with each of four β-globin-targeted ZFNs (see Example 20 for characterization of these ZFNs). The rightmost three lanes show results of incubation of template DNA with the sca-29b ZFN and one of the sca-36a, sca-36b or sca-36c ZFNs (all of which are targeted to the strand opposite that to which sca-29b is targeted).

Figure 42:
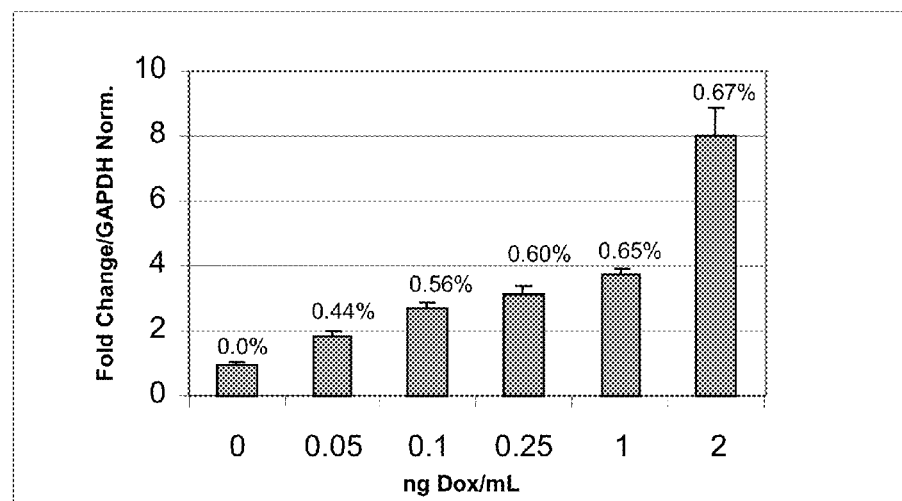

FIG. 42 shows levels of eGFP mRNA in T18 cells (bars) as a function of doxycycline concentration (provided on the abscissa). The number above each bar represents the percentage correction of the eGFP mutation, in cells transfected with donor DNA and plasmids encoding eGFP-targeted zinc finger nucleases, as a function of doxycycline concentration.

DETAILED DESCRIPTION

Disclosed herein are compositions and methods useful for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence. Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, translocations, rearrangements, and/or point mutations. A genomic sequence can also comprise one of a number of different alleles.

Compositions useful for targeted cleavage and recombination include fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any genomic sequence. Thus, by identifying a target genomic region of interest at which cleavage or recombination is desired, one can, according to the methods disclosed herein, construct one or more fusion proteins comprising a cleavage domain (or cleavage half-domain) and a zinc finger domain engineered to recognize a target sequence in said genomic region. The presence of such a fusion protein (or proteins) in a cell will result in binding of the fusion protein(s) to its (their) binding site(s) and cleavage within or near said genomic region. Moreover, if an exogenous polynucleotide homologous to the genomic region is also present in such a cell, homologous recombination occurs at a high rate between the genomic region and the exogenous polynucleotide.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found online. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

Target Sites

The disclosed methods and compositions include fusion proteins comprising a cleavage domain (or a cleavage half-domain) and a zinc finger domain, in which the zinc finger domain, by binding to a sequence in cellular chromatin (e.g., a target site or a binding site), directs the activity of the cleavage domain (or cleavage half-domain) to the vicinity of the sequence and, hence, induces cleavage in the vicinity of the target sequence. As set forth elsewhere in this disclosure, a zinc finger domain can be engineered to bind to virtually any desired sequence. Accordingly, after identifying a region of interest containing a sequence at which cleavage or recombination is desired, one or more zinc finger binding domains can be engineered to bind to one or more sequences in the region of interest. Expression of a fusion protein comprising a zinc finger binding domain and a cleavage domain (or of two fusion proteins, each comprising a zinc finger binding domain and a cleavage half-domain), in a cell, effects cleavage in the region of interest.

Selection of a sequence in cellular chromatin for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

Zinc Finger Binding Domains

A zinc finger binding domain comprises one or more zinc fingers. Miller et al. (1985) *EMBO J.* 4:1609-1614; Rhodes (1993) *Scientific American* Febuary:56-65; U.S. Pat. No. 6,453,242. Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) *Proc. Natl. Acad. Sci. USA* 98:1432-1436; Moore et al. (2001b) *Proc. Natl. Acad. Sci. USA* 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Cleavage Domains

The cleavage domain portion of the fusion proteins disclosed herein can be obtained from any endo- or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain (e.g., fusion proteins comprising a zinc finger binding domain and a cleavage half-domain) can be derived from any nuclease or portion thereof, as set forth above, that requires dimerization for cleavage activity. In general, two fusion proteins are required for cleavage if the fusion proteins comprise cleavage half-domains. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

In general, if two fusion proteins are used, each comprising a cleavage half-domain, the primary contact strand for the zinc finger portion of each fusion protein will be on a different DNA strands and in opposite orientation. That is, for a pair of ZFP/cleavage half-domain fusions, the target sequences are on opposite strands and the two proteins bind in opposite orientations.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-Fok I fusions are provided elsewhere in this disclosure.

Exemplary Type IIS restriction enzymes are listed in Table 1. Additional restriction enzymes also contain separable binding and cleavage domains, and these are contemplated by the present disclosure. See, for example, Roberts et al. (2003) *Nucleic Acids Res.* 31:418-420.

TABLE 1

| Some Type IIS Restriction Enzymes | | |
|---|---|---|
| Aar I | BsrB I | SspD5 I |
| Ace III | BsrD I | Sth132 I |
| Aci I | BstF5 I | Sts I |
| Alo I | Btr I | TspDT I |
| Bae I | Bts I | TspGW I |
| Bbr7 I | Cdi I | Tth111 II |
| Bbv I | CjeP I | UbaP I |
| Bbv II | Drd II | Bsa I |
| BbvC I | Eci I | BsmB I |
| Bcc I | Eco31 I | |
| Bce83 I | Eco57 I | |
| BceA I | Eco57M I | |
| Bcef I | Esp3 I | |
| Bcg I | Fau I | |
| BciV I | Fin I | |
| Bfi I | Fok I | |
| Bin I | Gdi II | |
| Bmg I | Gsu I | |
| Bpu10 I | Hga I | |
| BsaX I | Hin4 II | |
| Bsb I | Hph I | |
| BscA I | Ksp632 I | |
| BscG I | Mbo II | |
| BseR I | Mly I | |
| BseY I | Mme I | |
| Bsi I | Mnl I | |
| Bsm I | Pfl1108 I | |
| BsmA I | Ple I | |
| BsmF I | Ppi I | |
| Bsp24 I | Psr I | |
| BspG I | RleA I | |
| BspM I | Sap I | |
| BspNC I | SfaN I | |
| Bsr I | Sim I | |

Zinc Finger Domain-Cleavage Domain Fusions

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In general, the components of the fusion proteins (e.g., ZFP-Fok I fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus.

In the disclosed fusion proteins, the amino acid sequence between the zinc finger binding domain (which is delimited by the N-terminal most of the two conserved cysteine residues and the C-terminal-most of the two conserved histidine residues) and the cleavage domain (or half-domain) is denoted the "ZC linker." The ZC linker is to be distinguished from the inter-finger linkers discussed above. For instance, in a ZFP-Fok I fusion protein (in which the components are arranged: N terminus-zinc finger binding domain-Fok I cleavage half domain-C terminus), the ZC linker is located between the second histidine residue of the C-terminal-most zinc finger and the N-terminal-most amino acid residue of the cleavage half-domain (which is generally glutamine (Q) in the sequence QLV). The ZC linker can be any amino acid sequence. To obtain optimal cleavage, the length of the linker and the distance between the target sites (binding sites) are interrelated. See, for example, Smith et al. (2000) *Nucleic Acids Res.* 28:3361-3369; Bibikova et al. (2001) *Mol. Cell. Biol.* 21:289-297, noting that their notation for linker length differs from that given here. For example, for ZFP-Fok I fusions having a ZC linker length of four amino acids (as defined herein), optimal cleavage occurs when the binding sites for the fusion proteins are located 6 or 16 nucleotides apart (as measured from the near edge of each binding site).

Methods for Targeted Cleavage

The disclosed methods and compositions can be used to cleave DNA at a region of interest in cellular chromatin (e.g., at a desired or predetermined site in a genome, for example, in a gene, either mutant or wild-type). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near which cleavage is desired. The fusion protein, or a polynucleotide encoding same, is introduced into a cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (See, for example, Smith et al. (2000) *Nucleic Acids Res.* 28:3361-3369; Bibikova et al. (2001) *Mol. Cell. Biol.* 21:289-297) and the length of the ZC linker in each fusion protein.

For ZFP-FokI fusion nucleases, the length of the linker between the ZFP and the FokI cleavage half-domain (i.e., the ZC linker) can influence cleavage efficiency. In one experimental system utilizing a ZFP-FokI fusion with a ZC linker of 4 amino acid residues, optimal cleavage was obtained when the near edges of the binding sites for two ZFP-FokI nucleases were separated by 6 base pairs. This particular fusion nuclease comprised the following amino acid sequence between the zinc finger portion and the nuclease half-domain:

<u>H</u>QRT<u>H</u>QNKK<u>QLV</u> (SEQ ID NO:26)

in which the two conserved histidines in the C-terminal portion of the zinc finger and the first three residues in the FokI cleavage half-domain are underlined. Accordingly, the linker sequence in this construct is QNKK. Bibikova et al. (2001) *Mol. Cell. Biol.* 21:289-297. The present inventors have constructed a number of ZFP-FokI fusion nucleases having a variety of ZC linker lengths and sequences, and analyzed the cleavage efficiencies of these nucleases on a series of substrates having different distances between the ZFP binding sites. See Example 4.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian genome, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins are bound, its cleavage half-domain forms a dimer with the dominant negative mutant half-domain, and undesirable, non-specific cleavage does not occur.

Three catalytic amino acid residues in the Fok I cleavage half-domain have been identified: Asp 450, Asp 467 and Lys 469. Bitinaite et al. (1998) *Proc. Natl. Acad. Sci. USA* 95: 10,570-10,575. Thus, one or more mutations at one of these residues can be used to generate a dominant negative mutation. Further, many of the catalytic amino acid residues of other Type IIS endonucleases are known and/or can be determined, for example, by alignment with Fok I sequences and/or by generation and testing of mutants for catalytic activity.

Dimerization Domain Mutations in the Cleavage Half-Domain

Methods for targeted cleavage which involve the use of fusions between a ZFP and a cleavage half-domain (such as, e.g., a ZFP/FokI fusion) require the use of two such fusion molecules, each generally directed to a distinct target sequence. Target sequences for the two fusion proteins can be chosen so that targeted cleavage is directed to a unique site in a genome, as discussed above. A potential source of reduced cleavage specificity could result from homodimerization of one of the two ZFP/cleavage half-domain fusions. This might occur, for example, due to the presence, in a genome, of inverted repeats of the target sequences for one of the two ZFP/cleavage half-domain fusions, located so as to allow two copies of the same fusion protein to bind with an orientation and spacing that allows formation of a functional dimer.

One approach for reducing the probability of this type of aberrant cleavage at sequences other than the intended target site involves generating variants of the cleavage half-domain that minimize or prevent homodimerization. Preferably, one or more amino acids in the region of the half-domain involved in its dimerization are altered. In the crystal structure of the FokI protein dimer, the structure of the cleavage half-domains is reported to be similar to the arrangement of the cleavage half-domains during cleavage of DNA by FokI. Wah et al. (1998) *Proc. Natl. Acad. Sci. USA* 95:10564-10569. This structure indicates that amino acid residues at positions 483 and 487 play a key role in the dimerization of the FokI cleavage half-domains. The structure also indicates that amino acid residues at positions 446, 447, 479, 483, 484, 486, 487, 490, 491, 496, 498, 499, 500, 531, 534, 537, and 538 are all close enough to the dimerization interface to influence dimerization. Accordingly, amino acid sequence alterations at one or more of the aforementioned positions will likely alter the dimerization properties of the cleavage half-domain. Such changes can be introduced, for example, by constructing a library containing (or encoding) different amino acid residues at these positions and selecting variants with the desired properties, or by rationally designing individual mutants. In addition to preventing homodimerization, it is also possible that some of these mutations may increase the cleavage efficiency above that obtained with two wild-type cleavage half-domains.

Accordingly, alteration of a FokI cleavage half-domain at any amino acid residue which affects dimerization can be used to prevent one of a pair of ZFP/FokI fusions from undergoing homodimerization which can lead to cleavage at undesired sequences. Thus, for targeted cleavage using a pair of ZFP/FokI fusions, one or both of the fusion proteins can comprise one or more amino acid alterations that inhibit self-dimerization, but allow heterodimerization of the two fusion proteins to occur such that cleavage occurs at the desired target site. In certain embodiments, alterations are present in both fusion proteins, and the alterations have additive effects; i.e., homodimerization of either fusion, leading to aberrant cleavage, is minimized or abolished, while heterodimerization of the two fusion proteins is facilitated compared to that obtained with wild-type cleavage half-domains. See Example 5.

Methods for Targeted Alteration of Genomic Sequences and Targeted Recombination

Also described herein are methods of replacing a genomic sequence (e.g., a region of interest in cellular chromatin) with a homologous non-identical sequence (i.e., targeted recombination). Previous attempts to replace particular sequences have involved contacting a cell with a polynucleotide comprising sequences bearing homology to a chromosomal region (i.e., a donor DNA), followed by selection of cells in which the donor DNA molecule had undergone homologous recombination into the genome. The success rate of these methods is low, due to poor efficiency of homologous recombination and a high frequency of non-specific insertion of the donor DNA into regions of the genome other than the target site.

The present disclosure provides methods of targeted sequence alteration characterized by a greater efficiency of targeted recombination and a lower frequency of non-specific insertion events. The methods involve making and using engineered zinc finger binding domains fused to cleavage domains (or cleavage half-domains) to make one or more targeted double-stranded breaks in cellular DNA. Because double-stranded breaks in cellular DNA stimulate homologous recombination several thousand-fold in the vicinity of the cleavage site, such targeted cleavage allows for the alteration or replacement (via homologous recombination) of sequences at virtually any site in the genome.

In addition to the fusion molecules described herein, targeted replacement of a selected genomic sequence also requires the introduction of the replacement (or donor) sequence. The donor sequence can be introduced into the cell prior to, concurrently with, or subsequent to, expression of the fusion protein(s). The donor polynucleotide contains sufficient homology to a genomic sequence to support homologous recombination between it and the genomic sequence to which it bears homology. Approximately 25, 50 100 or 200 nucleotides or more of sequence homology between a donor and a genomic sequence (or any integral value between 10 and 200 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology is present to support homologous recombination. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of the donor sequence, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV).

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homologous recombination. Applicants' methods advantageously combine the powerful targeting capabilities of engineered ZFPs with a cleavage domain (or cleavage half-domain) to specifically target a double-stranded break to the region of the genome at which recombination is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC3), genes whose products interact with the aforementioned gene products (e.g., BRCA1, BRCA2) and/or genes in the NBS1 complex. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Yanez et al. (1998) *Gene Therapy* 5:149-159; Hoeijmakers (2001) *Nature* 411:366-374; Johnson et al. (2001) *Biochem. Soc. Trans.* 29:196-201; Tauchi et al. (2002) *Oncogene* 21:8967-8980. Methods for activation and repression of gene expression using fusions between a zinc finger binding domain and a functional domain are disclosed in co-owned U.S. Pat. No. 6,534,261. Additional repression methods include the use of antisense oligonucleotides and/or small interfering RNA (siRNA or RNAi) targeted to the sequence of the gene to be repressed.

As an alternative to or, in addition to, activating expression of gene products involved in homologous recombination, fusions of these protein (or functional fragments thereof) with a zinc finger binding domain targeted to the region of interest, can be used to recruit these proteins (recombination proteins) to the region of interest, thereby increasing their local concentration and further stimulating homologous recombination processes. Alternatively, a polypeptide involved in homologous recombination as described above (or a functional fragment thereof) can be part of a triple fusion protein comprising a zinc finger binding domain, a cleavage domain (or cleavage half-domain) and the recombination protein (or functional fragment thereof). Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases.

The p53 protein has been reported to play a central role in repressing homologous recombination (HR). See, for example, Valerie et al., (2003) *Oncogene* 22:5792-5812; Janz, et al. (2002) *Oncogene* 21:5929-5933. For example, the rate of HR in p53-deficient human tumor lines is 10,000-fold greater than in primary human fibroblasts, and there is a 100-fold increase in HR in tumor cells with a non-functional p53 compared to those with functional p53. Mekeel et al. (1997) *Oncogene* 14:1847-1857. In addition, overexpression of p53 dominant negative mutants leads to a 20-fold increase in spontaneous recombination. Bertrand et al. (1997) *Oncogene* 14:1117-1122. Analysis of different p53 mutations has revealed that the roles of p53 in transcriptional transactivation and G1 cell cycle checkpoint control are separable from its involvement in HR. Saintigny et al. (1999) *Oncogene* 18:3553-3563; Boehden et al. (2003) *Oncogene* 22:4111-4117. Accordingly, downregulation of p53 activity can serve to increase the efficiency of targeted homologous recombination using the methods and compositions disclosed herein. Any method for downregulation of p53 activity can be used, including but not limited to cotransfection and overexpression of a p53 dominant negative mutant or targeted repression of p53 gene expression according to methods disclosed, e.g., in co-owned U.S. Pat. No. 6,534,261.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Methods to Screen for Cellular Factors that Facilitate Homologous Recombination

Since homologous recombination is a multi-step process requiring the modification of DNA ends and the recruitment of several cellular factors into a protein complex, the addition of one or more exogenous factors, along with donor DNA and vectors encoding zinc finger-cleavage domain fusions, can be used to facilitate targeted homologous recombination. An exemplary method for identifying such a factor or factors employs analyses of gene expression using microarrays (e.g., Affymetrix Gene Chip® arrays) to compare the mRNA expression patterns of different cells. For example, cells that exhibit a higher capacity to stimulate double strand break-driven homologous recombination in the presence of donor DNA and zinc finger-cleavage domain fusions, either unaided or under conditions known to increase the level of gene correction, can be analyzed for their gene expression patterns compared to cells that lack such capacity. Genes that are upregulated or downregulated in a manner that directly correlates with increased levels of homologous recombination are thereby identified and can be cloned into any one of a number of expression vectors. These expression constructs can be co-transfected along with zinc finger-cleavage domain fusions and donor constructs to yield improved methods for achieving high-efficiency homologous recombination. Alternatively, expression of such genes can be appropriately regulated using engineered zinc finger proteins which modulate expression (either activation or repression) of one or more these genes. See, e.g., co-owned U.S. Pat. No. 6,534,261 for methods for the synthesis of engineered zinc finger proteins for regulation of gene expression.

Figure 27:
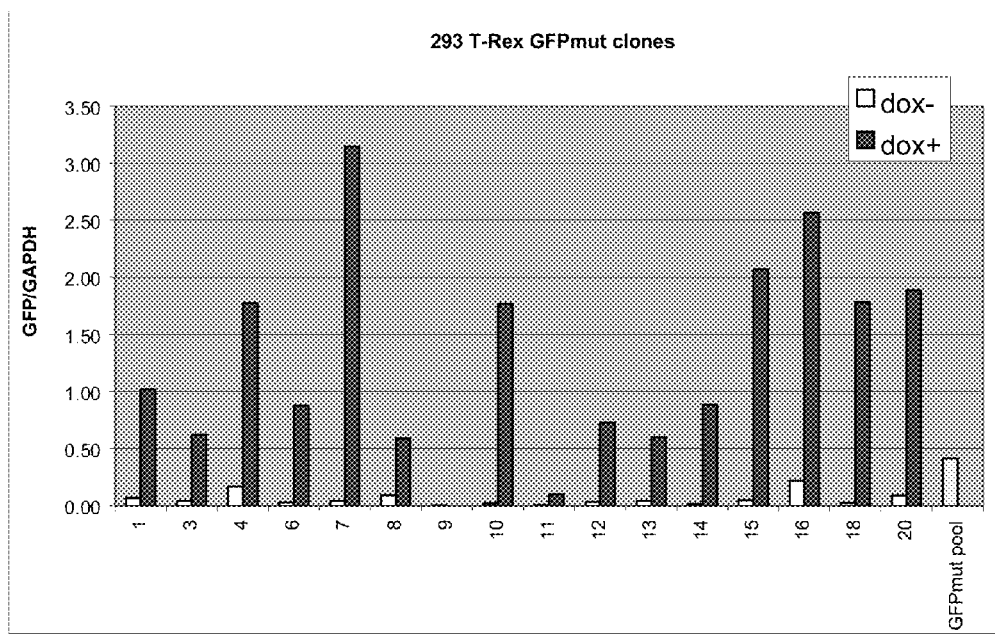
FIG. 27 shows levels of eGFPmut mRNA, normalized to GAPDH mRNA, in various cell lines obtained from transfection of human HEK293 cells. Light bars show levels in untreated cells; dark bars show levels in cell that had been treated with 2 ng/ml doxycycline. See Example 9 for details.

As an example, it was observed that the different clones obtained in the experiments described in Example 9 and FIG. 27 exhibited a wide-range of homologous recombination frequencies, when transfected with donor DNA and plasmids encoding zinc finger-cleavage domain fusions. Gene expression in clones showing a high frequency of targeted recombination can thus be compared to that in clones exhibiting a low frequency, and expression patterns unique to the former clones can be identified.

As an additional example, studies using cell cycle inhibitors (e.g., nocodazole or vinblastine, see e.g., Examples 11, 14 and 15) showed that cells arrested in the G2 phase of the cell cycle carried out homologous recombination at higher rates, indicating that cellular factors responsible for homologous recombination may be preferentially expressed or active in G2. One way to identify these factors is to compare the mRNA expression patterns between the stably transfected HEK 293 cell clones that carry out gene correction at high and low levels (e.g., clone T18 vs. clone T7). Similar comparisons are made between these cell lines in response to compounds that arrest the cells in G2 phase. Candidate genes that are differentially expressed in cells that carry out homologous recombination at a higher rate, either unaided or in response to compounds that arrest the cells in G2, are identified, cloned, and re-introduced into cells to determine whether their expression is sufficient to re-capitulate the improved rates. Alternatively, expression of said candidate genes is activated using engineered zinc finger transcription factors as described, for example, in co-owned U.S. Pat. No. 6,534,261.

Expression Vectors

A nucleic acid encoding one or more ZFPs or ZFP fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a ZFP can also be cloned into an expression vector, for administration to a plant cell, animal cell, preferably a mammalian cell or a human cell, fungal cell, bacterial cell, or protozoal cell.

To obtain expression of a cloned gene or nucleic acid, sequences encoding a ZFP or ZFP fusion protein are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; $3^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli*, *Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a ZFP-encoding nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). The MNDU3 promoter can also be used, and is preferentially active in $CD34^+$ hematopoietic stem cells.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the ZFP, e.g., expression in plants, animals, bacteria, fungus, protozoa, etc. (see expression vectors described below). Standard bacterial expression vectors include plasmids such as pBR322-based plasmids, pSKF, pET23D, and commercially available fusion expression systems such as GST and LacZ. An exemplary fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acids Encoding Fusion Proteins and Delivery to Cells

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue.

Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SW), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

DNA constructs may be introduced into the genome of a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227: 1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture, pp.* 124-176, Macmillian Publishing Company, New York, 1983; and Binding, *Regeneration of Plants, Plant Protoplasts, pp.* 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, *Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or Cl genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Delivery Vehicles

An important factor in the administration of polypeptide compounds, such as ZFP fusion proteins, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Chem.* 270:1 4255-14258 (1995)).

Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) *Molecular Therapy* 7(5):S461, Abstract #1191.

Toxin molecules also have the ability to transport polypeptides across cell membranes. Often, such molecules (called "binary toxins") are composed of at least two parts: a translocation/binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Such peptide sequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858:161-168 (1986); Williams et al., *PNAS* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are known to those of skill in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes of lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337-16342 (1990) and Leonetti et al., *PNAS* 87:2448-2451 (1990).

Dosages

For therapeutic applications, the dose administered to a patient, or to a cell which will be introduced into a patient, in the context of the present disclosure, should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy and $K_d$ of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

The maximum therapeutically effective dosage of ZFP for approximately 99% binding to target sites is calculated to be in the range of less than about $1.5 \times 10^5$ to $1.5 \times 10^6$ copies of the specific ZFP molecule per cell. The number of ZFPs per cell for this level of binding is calculated as follows, using the volume of a HeLa cell nucleus (approximately 1000 µm³ or $10^{-12}$ L; *Cell Biology*, (Altman & Katz, eds. (1976)). As the HeLa nucleus is relatively large, this dosage number is recalculated as needed using the volume of the target cell nucleus. This calculation also does not take into account competition for ZFP binding by other sites. This calculation also assumes that essentially all of the ZFP is localized to the nucleus. A value of $100 \times K_d$ is used to calculate approximately 99% binding of to the target site, and a value of $10 \times K_d$ is used to calculate approximately 90% binding of to the target site. For this example, $K_d=25$ nM ZFP+target site ↔ complex i.e., DNA+protein ↔ DNA:protein complex $K_d$=[DNA][protein]

[DNA:protein complex]

When 50% of ZFP is bound, $K_d$=[protein]

So when [protein]=25 nM and the nucleus volume is $10^{-12}$ L

[protein]=($25 \times 10^{-9}$ moles/L) ($10^{-12}$ L/nucleus) ($6 \times 10^{23}$ molecules/mole)

=15,000 molecules/nucleus for 50% binding

When 99% target is bound; $100 \times K_d$=[protein]

$100 \times K_d$=[protein]=2.5 µM ($2.5 \times 10^{-6}$ moles/L) ($10^{-12}$ L/nucleus) ($6 \times 10^{23}$ molecules/mole)=about 1,500,000 molecules per nucleus for 99% binding of target site.

The appropriate dose of an expression vector encoding a ZFP can also be calculated by taking into account the average rate of ZFP expression from the promoter and the average rate of ZFP degradation in the cell. In certain embodiments, a weak promoter such as a wild-type or mutant HSV TK promoter is used, as described above. The dose of ZFP in micrograms is calculated by taking into account the molecular weight of the particular ZFP being employed.

In determining the effective amount of the ZFP to be administered in the treatment or prophylaxis of disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

Pharmaceutical Compositions and Administration

ZFPs and expression vectors encoding ZFPs can be administered directly to the patient for targeted cleavage and/or recombination, and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by ZFP gene therapy include pathogenic bacteria, e.g., chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria; infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences,* $17^{th}$ ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Applications

The disclosed methods and compositions for targeted cleavage can be used to induce mutations in a genomic sequence, e.g., by cleaving at two sites and deleting sequences in between, by cleavage at a single site followed by non-homologous end joining, and/or by cleaving at a site so as to remove one or two or a few nucleotides. Targeted cleavage can also be used to create gene knock-outs (e.g., for functional genomics or target validation) and to facilitate targeted insertion of a sequence into a genome (i.e., gene knock-in); e.g., for purposes of cell engineering or protein overexpression. Insertion can be by means of replacements of chromosomal sequences through homologous recombination or by targeted integration, in which a new sequence (i.e., a sequence not present in the region of interest), flanked by sequences homologous to the region of interest in the chromosome, is inserted at a predetermined target site.

The same methods can also be used to replace a wild-type sequence with a mutant sequence, or to convert one allele to a different allele.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

In similar fashion, the genome of an infecting bacterium can be mutagenized by targeted DNA cleavage followed by non-homologous end joining, to block or ameliorate bacterial infections.

The disclosed methods for targeted recombination can be used to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064. Treated stem cells can be returned to a patient for treatment of various diseases including, but not limited to, SCID and sickle-cell anemia.

In many of these cases, a region of interest comprises a mutation, and the donor polynucleotide comprises the corresponding wild-type sequence. Similarly, a wild-type genomic sequence can be replaced by a mutant sequence, if such is desirable. For example, overexpression of an oncogene can be reversed either by mutating the gene or by replacing its control sequences with sequences that support a lower, non-pathologic level of expression. As another example, the wild-type allele of the ApoAI gene can be replaced by the ApoAI Milano allele, to treat atherosclerosis. Indeed, any pathology dependent upon a particular genomic sequence, in any fashion, can be corrected or alleviated using the methods and compositions disclosed herein.

Targeted cleavage and targeted recombination can also be used to alter non-coding sequences (e.g., regulatory sequences such as promoters, enhancers, initiators, terminators, splice sites) to alter the levels of expression of a gene product. Such methods can be used, for example, for therapeutic purposes, functional genomics and/or target validation studies.

The compositions and methods described herein also allow for novel approaches and systems to address immune reactions of a host to allogeneic grafts. In particular, a major problem faced when allogeneic stem cells (or any type of allogeneic cell) are grafted into a host recipient is the high risk of rejection by the host's immune system, primarily mediated through recognition of the Major Histocompatibility Complex (MHC) on the surface of the engrafted cells. The MHC comprises the HLA class I protein(s) that function as heterodimers that are comprised of a common 13 subunit and variable α subunits. It has been demonstrated that tissue grafts derived from stem cells that are devoid of HLA escape the host's immune response. See, e.g., Coffman et al. *J Immunol* 151, 425-35. (1993); Markmann et al. *Transplantation* 54, 1085-9. (1992); Koller et al. *Science* 248, 1227-30. (1990). Using the compositions and methods described herein, genes encoding HLA proteins involved in graft rejection can be cleaved, mutagenized or altered by recombination, in either their coding or regulatory sequences, so that their expression is blocked or they express a non-functional product. For example, by inactivating the gene encoding the common β subunit gene (β2 microglobulin) using ZFP fusion proteins as described herein, HLA class I can be removed from the cells to rapidly and reliably generate HLA class I null stem cells from any donor, thereby reducing the need for closely matched donor/recipient MHC haplotypes during stem cell grafting.

Inactivation of any gene (e.g., the β2 microglobulin gene) can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, or by targeted recombination of an irrelevant sequence (i.e., a "stuffer" sequence) into the gene or its regulatory region, so as to disrupt the gene or regulatory region.

Targeted modification of chromatin structure, as disclosed in co-owned WO 01/83793, can be used to facilitate the binding of fusion proteins to cellular chromatin.

In additional embodiments, one or more fusions between a zinc finger binding domain and a recombinase (or functional fragment thereof) can be used, in addition to or instead of the zinc finger-cleavage domain fusions disclosed herein, to facilitate targeted recombination. See, for example, co-owned U.S. Pat. No. 6,534,261 and Akopian et al. (2003) *Proc. Natl. Acad. Sci. USA* 100:8688-8691.

In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

EXAMPLES

Example 1: Editing of a Chromosomal hSMC1L1 Gene by Targeted Recombination

The hSMC1L1 gene is the human orthologue of the budding yeast gene structural maintenance of chromosomes 1. A region of this gene encoding an amino-terminal portion of the protein which includes the Walker ATPase domain was mutagenized by targeted cleavage and recombination. Cleavage was targeted to the region of the methionine initiation codon (nucleotides 24-26, FIG. 1), by designing chimeric nucleases, comprising a zinc finger DNA-binding domain and a FokI cleavage half-domain, which bind in the vicinity of the codon. Thus, two zinc finger binding domains were designed, one of which recognizes nucleotides 23-34 (primary contacts along the top strand as shown in FIG. 1), and the other of which recognizes nucleotides 5-16 (primary contacts along the bottom strand). Zinc finger proteins were designed as described in co-owned U.S. Pat. Nos. 6,453,242 and 6,534,261. See Table 2 for the amino acid sequences of the recognition regions of the zinc finger proteins.

Figure 2:
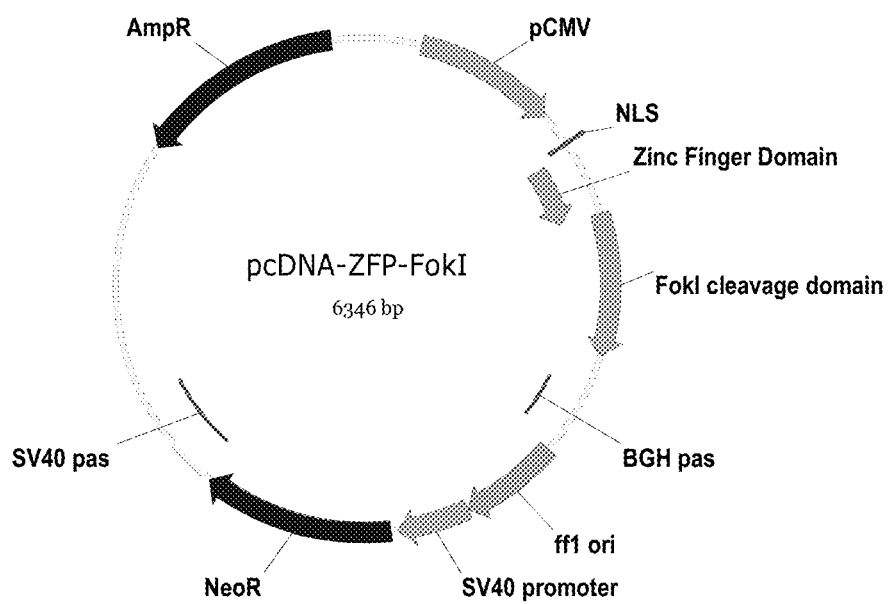
FIG. 2 shows a schematic diagram of a plasmid encoding a ZFP-FokI fusion for targeted cleavage of the hSMC1 gene.

Sequences encoding each of these two ZFP binding domains were fused to sequences encoding a FokI cleavage half-domain (amino acids 384-579 of the native FokI sequence; Kita et al. (1989) *J. Biol. Chem.* 264:5751-5756), such that the encoded protein contained FokI sequences at the carboxy terminus and ZFP sequences at the amino terminus. Each of these fusion sequences was then cloned in a modified mammalian expression vector pcDNA3 (FIG. 2).

TABLE 2

Zinc Finger Designs for the hSMC1L1 Gene

| Target sequence | F1 | F2 | F3 | F4 |
|---|---|---|---|---|
| CATGGGGTTCCT (SEQ ID NO: 27) | RSHDLIE (SEQ ID NO: 28) | TSSSLSR (SEQ ID NO: 29) | RSDHLST (SEQ ID NO: 30) | TNSNRIT (SEQ ID NO: 31) |
| GCGGCGCCGGCG (SEQ ID NO: 32) | RSDDLSR (SEQ ID NO: 33) | RSDDRKT (SEQ ID NO: 34) | RSEDLIR (SEQ ID NO: 35) | RSDTLSR (SEQ ID NO: 36) |

Note:
The zinc finger amino acid sequences shown above (in one-letter code) represent residues −1 through +6, with respect to the start of the alpha-helical portion of each zinc finger. Finger F1 is closest to the amino terminus of the protein, and Finger F4 is closest to the carboxy terminus.

Figure 3:
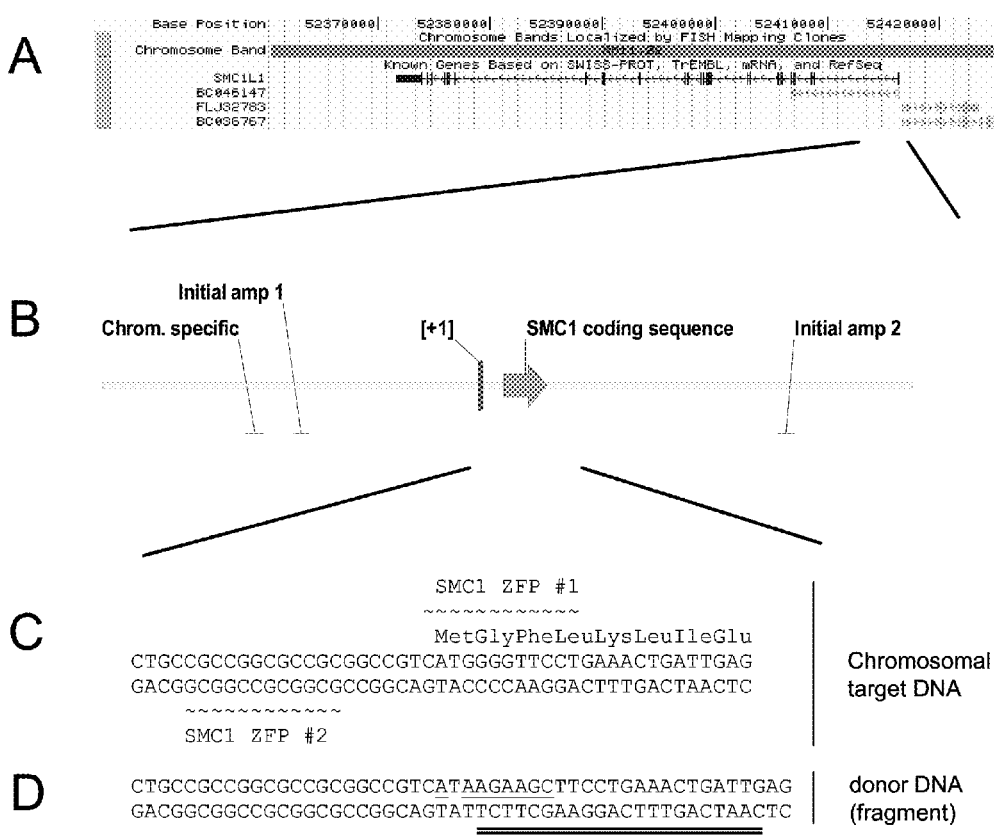
FIG. 3 A-D show a schematic diagram of the hSMC1 gene.
Figure 4:
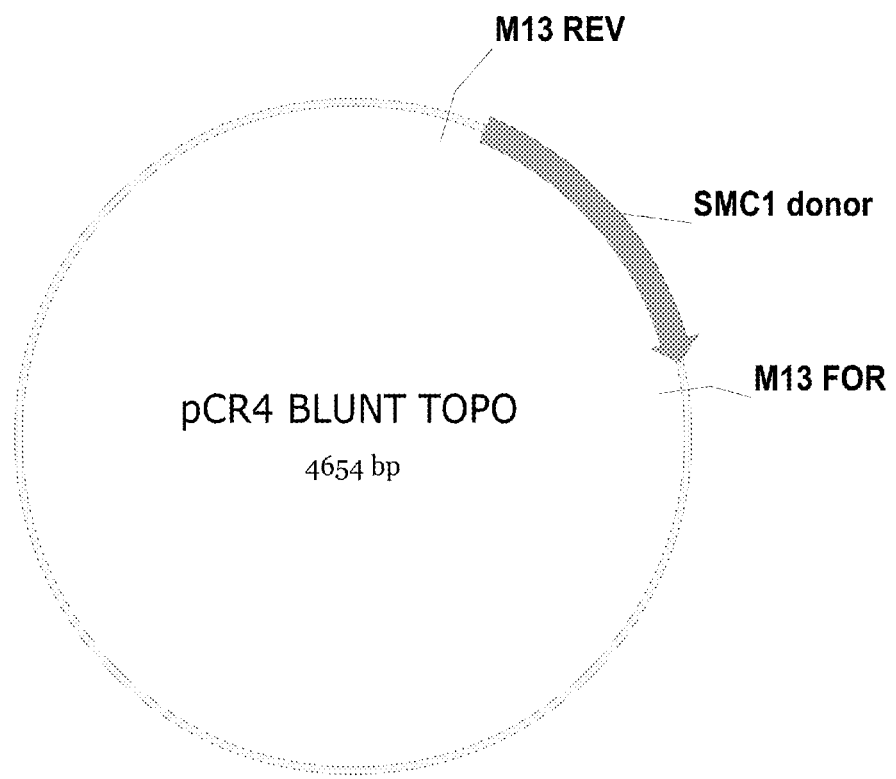
FIG. 4 shows a schematic diagram of the hSMC1 donor construct.

A donor DNA molecule was obtained as follows. First, a 700 base pair fragment of human genomic DNA representing nucleotides 52415936-52416635 of the "−" strand of the X chromosome (UCSC human genome release July, 2003), which includes the first exon of the human hSMC1L1 gene, was amplified, using genomic DNA from HEK293 cells as template. Sequences of primers used for amplification are shown in Table 3 ("Initial amp 1" and "Initial amp 2"). The PCR product was then altered, using standard overlap extension PCR methodology (see, e.g., Ho, et al. (1989) *Gene* 77:51-59), resulting in replacement of the sequence ATGGGG (nucleotides 24-29 in FIG. 1) to ATAAGAAGC. This change resulted in conversion of the ATG codon (methionine) to an ATA codon (isoleucine) and replacement of GGG (nucleotides 27-29 in FIG. 1) by the sequence AGAAGC, allowing discrimination between donor-derived sequences and endogenous chromosomal sequences following recombination. A schematic diagram of the hSMC1 gene, including sequences of the chromosomal DNA in the region of the initiation codon, and sequences in the donor DNA that differ from the chromosomal sequence, is given in FIG. 3. The resulting 700 base pair donor fragment was cloned into pCR4BluntTopo, which does not contain any sequences homologous to the human genome. See FIG. 4.

For targeted mutation of the chromosomal hSMC1L1 gene, the two plasmids encoding ZFP-FokI fusions and the donor plasmid were introduced into 1×10$^6$ HEK293 cells by transfection using Lipofectamine 2000® (Invitrogen). Controls included cells transfected only with the two plasmids encoding the ZFP-FokI fusions, cells transfected only with the donor plasmid and cells transfected with a control plasmid (pEGFP-N1, Clontech). Cells were cultured in 5% $CO_2$ at 37° C. At 48 hours after transfection, genomic DNA was isolated from the cells, and 200 ng was used as template for PCR amplification, using one primer complementary to a region of the gene outside of its region of homology with the donor sequences (nucleotides 52416677-52416701 on the "−" STRAND of the X chromosome; UCSC July 2003), and a second primer complementary to a region of the donor molecule into which distinguishing mutations were introduced. Using these two primers, an amplification product of 400 base pairs will be obtained from genomic DNA if a targeted recombination event has occurred. The sequences of these primers are given in Table 3 (labeled "chromosome-specific" and "donor-specific," respectively). Conditions for amplification were: 94° C., 2 min, followed by 40 cycles of 94° C., 30 sec, 60° C., 1 min, 72° C., 1 min; and a final step of 72° C., 7 min.

Figure 5:
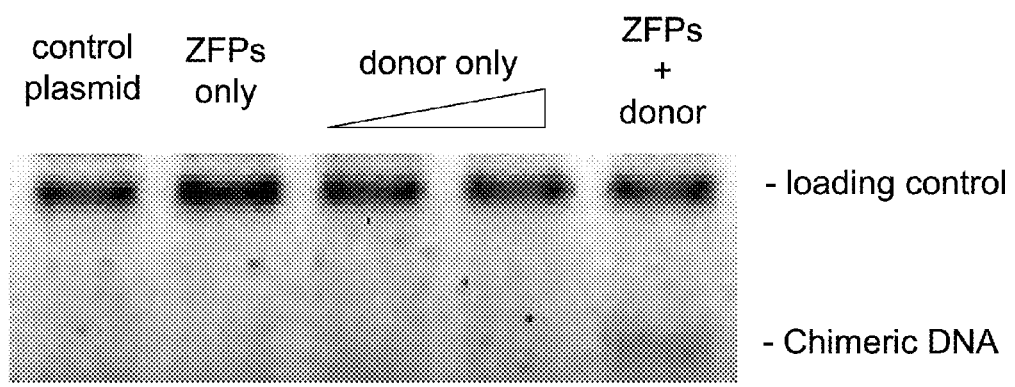
FIG. 5 shows PCR analysis of DNA from transfected HEK293 cells. From left, the lanes show results from cells transfected with a plasmid encoding GFP (control plasmid), cells transfected with two plasmids, each of which encodes one of the two hSMC1-specific ZFP-FokI fusion proteins (ZFPs only), cells transfected with two concentrations of the hSMC1 donor plasmid (donor only), and cells transfected with the two ZFP-encoding plasmids and the donor plasmid (ZFPs+donor). See Example 1 for details.

The results of this analysis (FIG. 5) indicate that a 400 base pair amplification product (labeled "Chimeric DNA" in the Figure) was obtained only with DNA extracted from cells which had been transfected with the donor plasmid and both ZFP-FokI plasmids.

TABLE 3

Amplification Primers for the hSMC1L1 Gene

| | |
|---|---|
| Initial amp 1 | AGCAACAACTCCTCCGGGGATC (SEQ ID NO: 37) |
| Initial amp 2 | TTCCAGACGCGACTCTTTGGC (SEQ ID NO: 38) |
| Chromosome-specific | CTCAGCAAGCGTGAGCTCAGGTCTC (SEQ ID NO: 39) |
| Donor-specific | CAATCAGTTTCAGGAAGCTTCTT (SEQ ID NO: 40) |
| Outside 1 | CTCAGCAAGCGTGAGCTCAGGTCTC (SEQ ID NO: 41) |
| Outside 2 | GGGGTCAAGTAAGGCTGGGAAGC (SEQ ID NO: 42) |

To confirm this result, two additional experiments were conducted. First, the amplification product was cloned into pCR4Blunt-Topo (Invitrogen) and its nucleotide sequence was determined. As shown in FIG. 6 (SEQ ID NO: 6), the amplified sequence obtained from chromosomal DNA of cells transfected with the two ZFP-FokI-encoding plasmids and the donor plasmid contains the AAGAAGC sequence that is unique to the donor (nucleotides 395-401 of the sequence presented in FIG. 6) covalently linked to chromosomal sequences not present in the donor molecule (nucleotides 32-97 of FIG. 6), indicating that donor sequences have been recombined into the chromosome. In particular, the G→A mutation converting the initiation codon to an isoleucine codon is observed at position 395 in the sequence.

In a second experiment, chromosomal DNA from cells transfected only with donor plasmid, cells transfected with both ZFP-FokI fusion plasmids, cells transfected with the donor plasmid and both ZFP-FokI fusion plasmids or cells transfected with the EGFP control plasmid was used as template for amplification, using primers complementary to sequences outside of the 700-nucleotide region of homology between donor and chromosomal sequences (identified as "Outside 1" and "Outside 2" in Table 3). The resulting amplification product was purified and used as template for a second amplification reaction using the donor-specific and chromosome-specific primers described above (Table 3). This amplification yielded a 400 nucleotide product only from cells transfected with the donor construct and both ZFP-FokI fusion constructs, a result consistent with the replacement of genomic sequences by targeted recombination in these cells.

Example 2: Editing of a Chromosomal IL2Rγ Gene by Targeted Recombination

The IL-2Rγ gene encodes a protein, known as the "common cytokine receptor gamma chain," that functions as a subunit of several interleukin receptors (including IL-2R, IL-4R, IL-7R, IL-9R, IL-15R and IL-21R). Mutations in this gene, including those surrounding the 5' end of the third exon (e.g. the tyrosine 91 codon), can cause X-linked severe combined immunodeficiency (SCID). See, for example, Puck et al. (1997) Blood 89:1968-1977. A mutation in the tyrosine 91 codon (nucleotides 23-25 of SEQ ID NO: 7; FIG. 7), was introduced into the IL2Rγ gene by targeted cleavage and recombination. Cleavage was targeted to this region by designing two pairs of zinc finger proteins. The first pair (first two rows of Table 4) comprises a zinc finger protein designed to bind to nucleotides 29-40 (primary contacts along the top strand as shown in FIG. 7) and a zinc finger protein designed to bind to nucleotides 8-20 (primary contacts along the bottom strand). The second pair (third and fourth rows of Table 4) comprises two zinc finger proteins, the first of which recognizes nucleotides 23-34 (primary contacts along the top strand as shown in FIG. 7) and the second of which recognizes nucleotides 8-16 (primary contacts along the bottom strand). Zinc finger proteins were designed as described in co-owned U.S. Pat. Nos. 6,453,242 and 6,534,261. See Table 4 for the amino acid sequences of the recognition regions of the zinc finger proteins.

Figure 8:
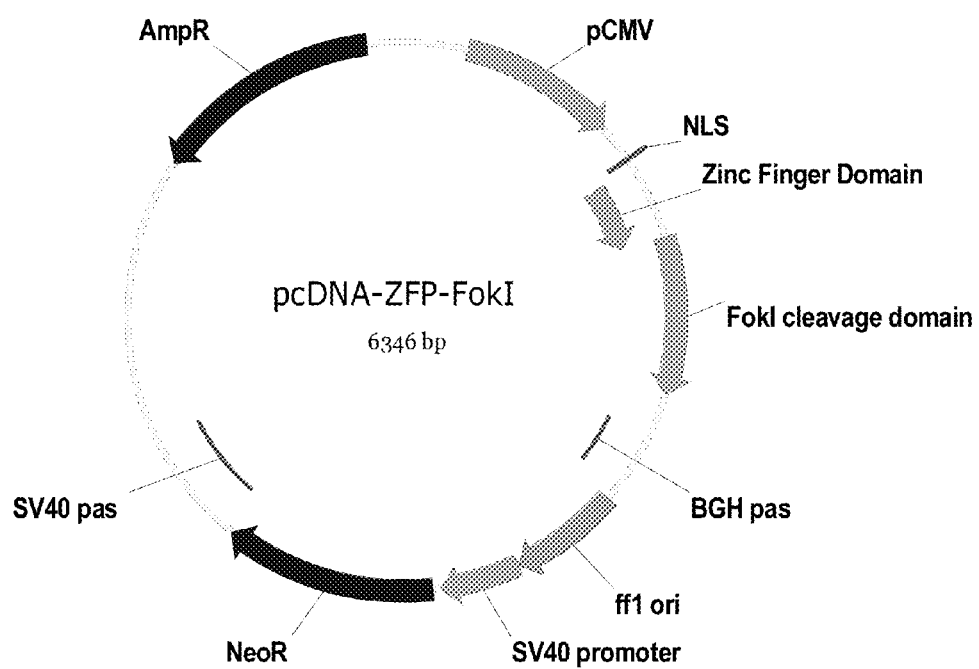
FIG. 8 shows a schematic diagram of a plasmid encoding a ZFP-FokI fusion for targeted cleavage of IL2Rγ gene.

Sequences encoding the ZFP binding domains were fused to sequences encoding a FokI cleavage half-domain (amino acids 384-579 of the native FokI sequence, Kita et al., supra), such that the encoded protein contained FokI sequences at the carboxy terminus and ZFP sequences at the amino terminus. Each of these fusion sequences was then cloned in a modified mammalian expression vector pcDNA3. See FIG. 8 for a schematic diagram of the constructs.

TABLE 4

Zinc Finger Designs for the IL2Rγ Gene

| Target sequence | F1 | F2 | F3 | F4 |
|---|---|---|---|---|
| AACTCGGATAAT (SEQ ID NO: 43) | DRSTLIE (SEQ ID NO: 44) | SSSNLSR (SEQ ID NO: 45) | RSDDLSK (SEQ ID NO: 46) | DNSNRIK (SEQ ID NO: 47) |
| TAGAGGaGAAAGG (SEQ ID NO: 48) | RSDNLSN (SEQ ID NO: 49) | TSSSRIN (SEQ ID NO: 50) | RSDHLSQ (SEQ ID NO: 51) | RNADRKT (SEQ ID NO: 52) |

TABLE 4-continued

Zinc Finger Designs for the IL2Rγ Gene

| Target sequence | F1 | F2 | F3 | F4 |
|---|---|---|---|---|
| TACAAGAACTCG (SEQ ID NO: 53) | RSDDLSK (SEQ ID NO: 54) | DNSNRIK (SEQ ID NO: 55) | RSDALSV (SEQ ID NO: 56) | DNANRTK (SEQ ID NO: 57) |
| GGAGAAAGG (SEQ ID NO: 58) | RSDHLTQ (SEQ ID NO: 59) | QSGNLAR (SEQ ID NO: 60) | RSDHLSR (SEQ ID NO: 61) | |

Note:
The zinc finger amino acid sequences shown above (in one-letter code) represent residues −1 through +6, with respect to the start of the alpha-helical portion of each zinc finger. Finger F1 is closest to the amino terminus of the protein.

Figure 9:
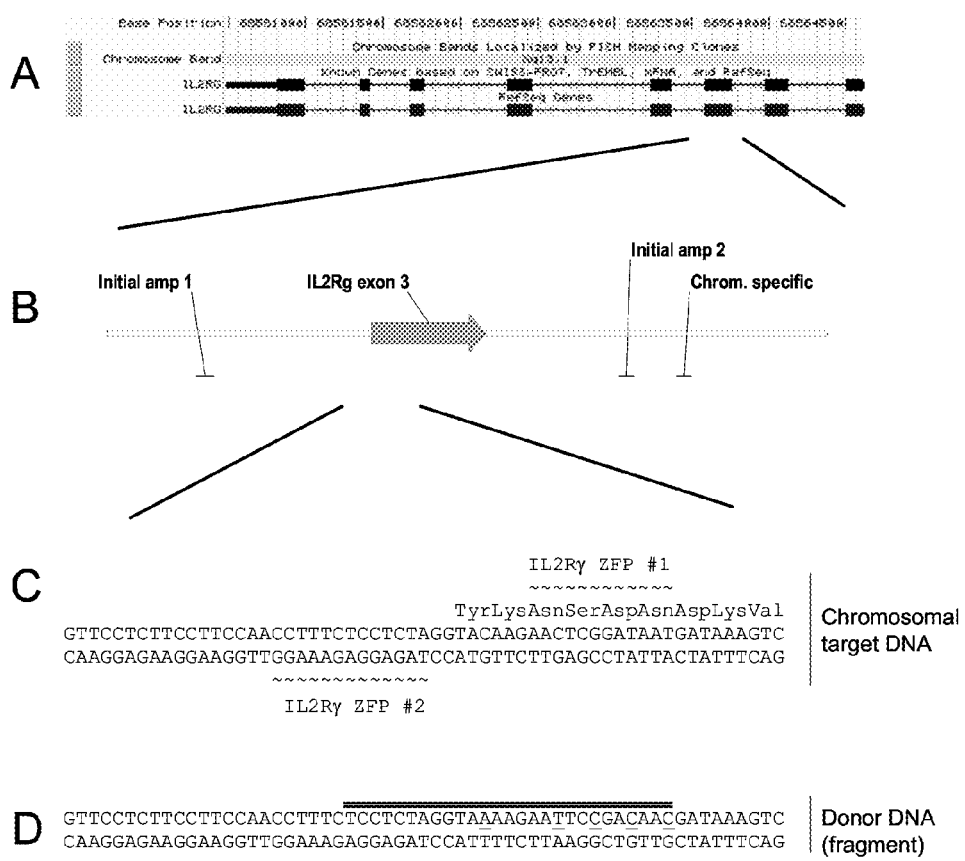
FIG. 9 A-D show a schematic diagram of the IL2Rγ gene.
Figure 10:
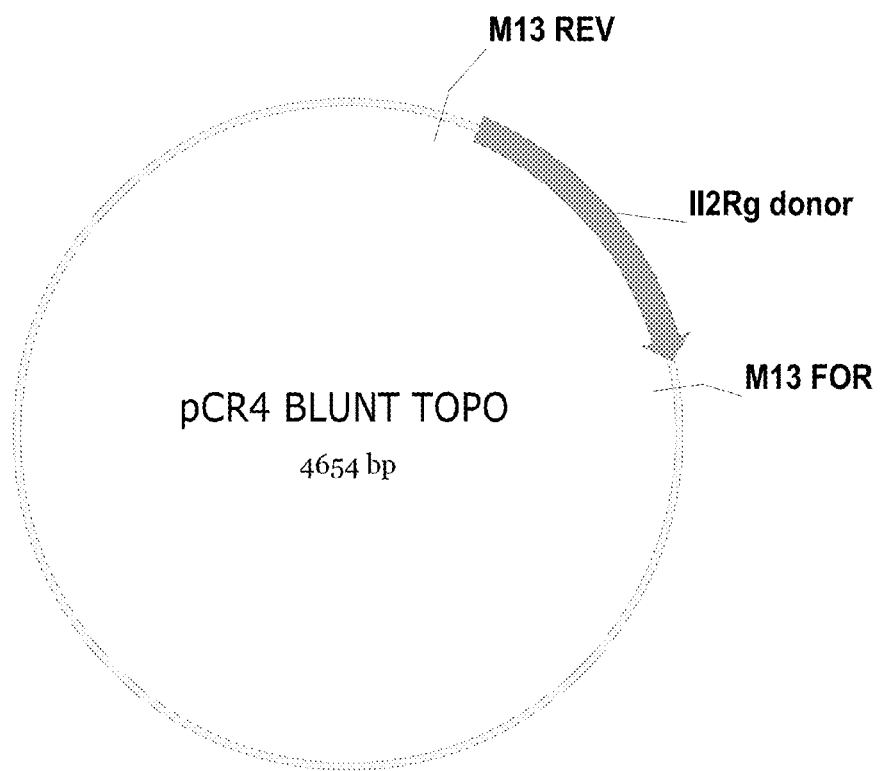
FIG. 10 shows a schematic diagram of the IL2Rγ donor construct.

A donor DNA molecule was obtained as follows. First, a 700 base pair fragment of human DNA corresponding to positions 69196910-69197609 on the "−" strand of the X chromosome (UCSC, July 2003), which includes exon 3 of the of the IL2Rγ gene, was amplified, using genomic DNA from K562 cells as template. See FIG. 9. Sequences of primers used for amplification are shown in Table 5 (labeled initial amp 1 and initial amp 2). The PCR product was then altered via standard overlap extension PCR methodology (Ho, et al., supra) to replace the sequence TACAAGAACTCGGATAAT (SEQ ID NO: 62) with the sequence TAAAAGAATTCCGACAAC (SEQ ID NO: 63). This replacement results in the introduction of a point mutation at nucleotide 25 (FIG. 7), converting the tyrosine 91 codon TAC to a TAA termination codon and enables discrimination between donor-derived and endogenous chromosomal sequences following recombination, because of differences in the sequences downstream of codon 91. The resulting 700 base pair fragment was cloned into pCR4BluntTopo which does not contain any sequences homologous to the human genome. See FIG. 10.

For targeted mutation of the chromosomal IL2Rγ gene, the donor plasmid, along with two plasmids each encoding one of a pair of ZFP-FokI fusions, were introduced into 2×10$^6$ K652 cells using mixed lipofection electroporation (Amaxa). Each of the ZFP/FokI pairs (see Table 4) was tested in separate experiments. Controls included cells transfected only with two plasmids encoding ZFP-FokI fusions, and cells transfected only with the donor plasmid. Cells were cultured in 5% $CO_2$ at 37° C. At 48 hours after transfection, genomic DNA was isolated from the cells, and 200 ng was used as template for PCR amplification, using one primer complementary to a region of the gene outside of its region of homology with the donor sequences (nucleotides 69196839-69196863 on the "+" strand of the X chromosome; UCSC, July 2003), and a second primer complementary to a region of the donor molecule into which distinguishing mutations were introduced (see above) and whose sequence therefore diverges from that of chromosomal DNA. See Table 5 for primer sequences, labeled "chromosome-specific" and "donor-specific," respectively. Using these two primers, an amplification product of 500 bp is obtained from genomic DNA in which a targeted recombination event has occurred. Conditions for amplification were: 94° C., 2 min, followed by 35 cycles of 94° C., 30 sec, 62° C., 1 min, 72° C., 45 sec; and a final step of 72° C., 7 min.

Figure 11:
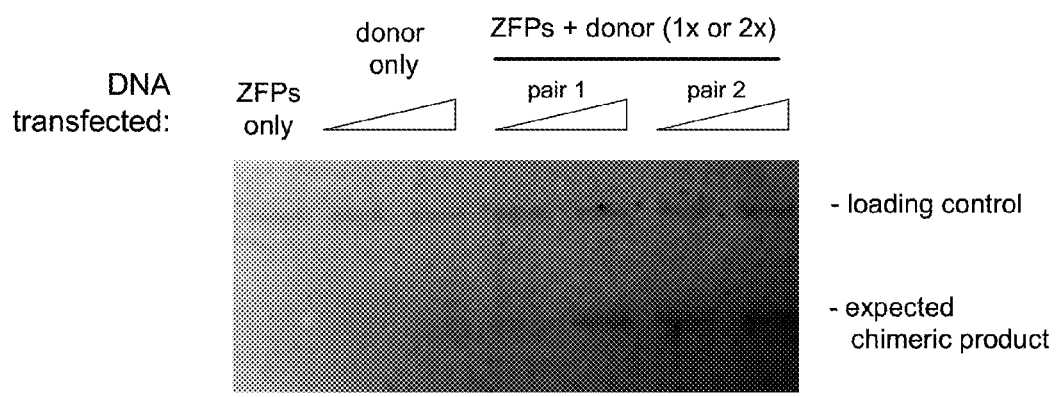
FIG. 11 shows PCR analysis of DNA from transfected K652 cells. From left, the lanes show results from cells transfected with two plasmids, each of which encodes one of a pair of IL2Rγ-specific ZFP-FokI fusion proteins (ZFPs only, lane 1), cells transfected with two concentrations of the IL2Rγ donor plasmid (donor only, lanes 2 and 3), and cells transfected with the two ZFP-encoding plasmids and the donor plasmid (ZFPs+donor, lanes 4-7). Each of the two pairs of IL2Rγ-specific ZFP-FokI fusions were used (identified as "pair 1" and "pair 2") and use of both pairs resulted in production of the diagnostic amplification product (labeled "expected chimeric product" in the Figure). See Example 2 for details.

The results of this analysis (FIG. 11) indicate that an amplification product of the expected size (500 base pairs) is obtained with DNA extracted from cells which had been transfected with the donor plasmid and either of the pairs of ZFP-FokI-encoding plasmids. DNA from cells transfected with plasmids encoding a pair of ZFPs only (no donor plasmid) did not result in generation of the 500 bp product, nor did DNA from cells transfected only with the donor plasmid.

TABLE 5

Amplification Primers for the IL2Rγ Gene

| | |
|---|---|
| Initial amp 1 | TGTCGAGTACATGAATTGCACTTGG (SEQ ID NO: 64) |
| Initial amp 2 | TTAGGTTCTCTGGAGCCCAGGG (SEQ ID NO: 65) |
| Chromosome-specific | CTCCAAACAGTGGTTCAAGAATCTG (SEQ ID NO: 66) |
| Donor-specific | TCCTCTAGGTAAAGAATTCCGACAAC (SEQ ID NO: 67) |

To confirm this result, the amplification product obtained from the experiment using the second pair of ZFP/FokI fusions was cloned into pCR4Blunt-Topo (Invitrogen) and its nucleotide sequence was determined. As shown in FIG. 12 (SEQ ID NO: 12), the sequence consists of a fusion between chromosomal sequences and sequences from the donor plasmid. In particular, the G to A mutation converting tyrosine 91 to a stop codon is observed at position 43 in the sequence. Positions 43-58 contain nucleotides unique to the donor; nucleotides 32-42 and 59-459 are sequences common to the donor and the chromosome, and nucleotides 460-552 are unique to the chromosome. The presence of donor-unique sequences covalently linked to sequences present in the chromosome but not in the donor indicates that DNA from the donor plasmid was introduced into the chromosome by homologous recombination.

Example 3: Editing of a Chromosomal β-Globin Gene by Targeted Recombination

Figure 14:
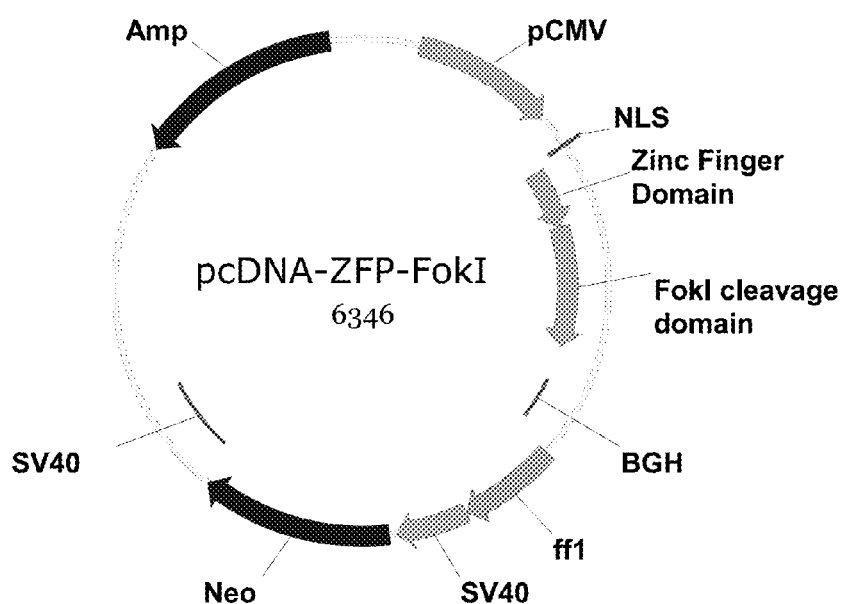
FIG. 14 is a schematic diagram of a plasmid encoding ZFP-FokI fusion for targeted cleavage of the human beta globin gene.

The human beta globin gene is one of two gene products responsible for the structure and function of hemoglobin in adult human erythrocytes. Mutations in the beta-globin gene can result in sickle cell anemia. Two zinc finger proteins were designed to bind within this sequence, near the location of a nucleotide which, when mutated, causes sickle cell anemia. FIG. 13 shows the nucleotide sequence of a portion of the human beta-globin gene, and the target sites for the two zinc finger proteins are underlined in the sequence presented in FIG. 13. Amino acid sequences of the recognition regions of the two zinc finger proteins are shown in Table 6. Sequences encoding each of these two ZFP binding domains were fused to sequences encoding a FokI cleavage half-domain, as described above, to create engineered ZFP-nucleases that targeted the endogenous beta globin gene. Each of these fusion sequences was then cloned in the mammalian expression vector pcDNA3.1 (FIG. 14).

For targeted mutation of the chromosomal beta globin gene, the two plasmids encoding ZFP-FokI fusions and the donor plasmid (pCR4-TOPO-HBBdonor) were introduced into $1\times10^6$ K562 cells by transfection using Nucleofector™ Solution (Amaxa Biosystems). Controls included cells transfected only with 100 ng (low) or 200 ng (high) of the two plasmids encoding the ZFP-FokI fusions, cells transfected only with 200 ng (low) or 600 ng (high) of the donor plasmid, cells transfected with a GFP-encoding plasmid, and mock transfected cells. Cells were cultured in RPMI Medium 1640 (Invitrogen), supplemented with 10% fetal bovine serum (FBS) (Hyclone) and 2 mM L-glutamine. Cells were maintained at 37° C. in an atmosphere of 5%

TABLE 6

Zinc Finger Designs for the beta-globin Gene

| Target sequence | F1 | F2 | F3 | F4 |
|---|---|---|---|---|
| GGGCAGTAACGG (SEQ ID NO: 68) | RSDHLSE (SEQ ID NO: 69) | QSANRTK (SEQ ID NO: 70) | RSDNLSA (SEQ ID NO: 71) | RSQNRTR (SEQ ID NO: 72) |
| AAGGTGAACGTG (SEQ ID NO: 73) | RSDSLSR (SEQ ID NO: 74) | DS SNRKT (SEQ ID NO: 75) | RSDSLSA (SEQ ID NO: 76) | RNDNRKT (SEQ ID NO: 77) |

Note:
The zinc finger amino acid sequences shown above (in one-letter code) represent residues −1 through +6, with respect to the start of the alpha-helical portion of each zinc finger. Finger F1 is closest to the amino terminus of the protein, and Finger F4 is closest to the carboxy terminus.

Figure 15:
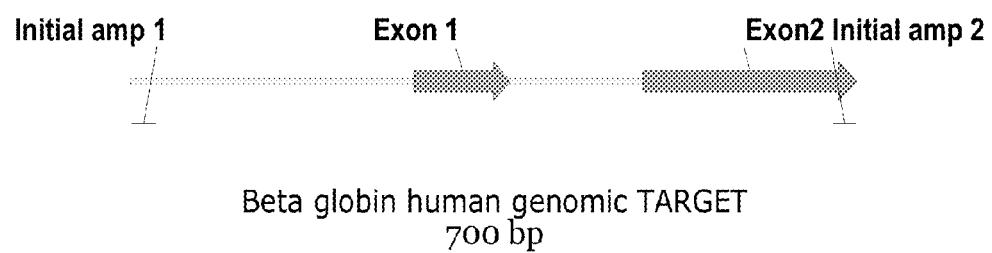
FIG. 15 is a schematic diagram of the cloned human beta globin gene showing the upstream region, first and second exons, first intron and primer binding sites.
Figure 16:
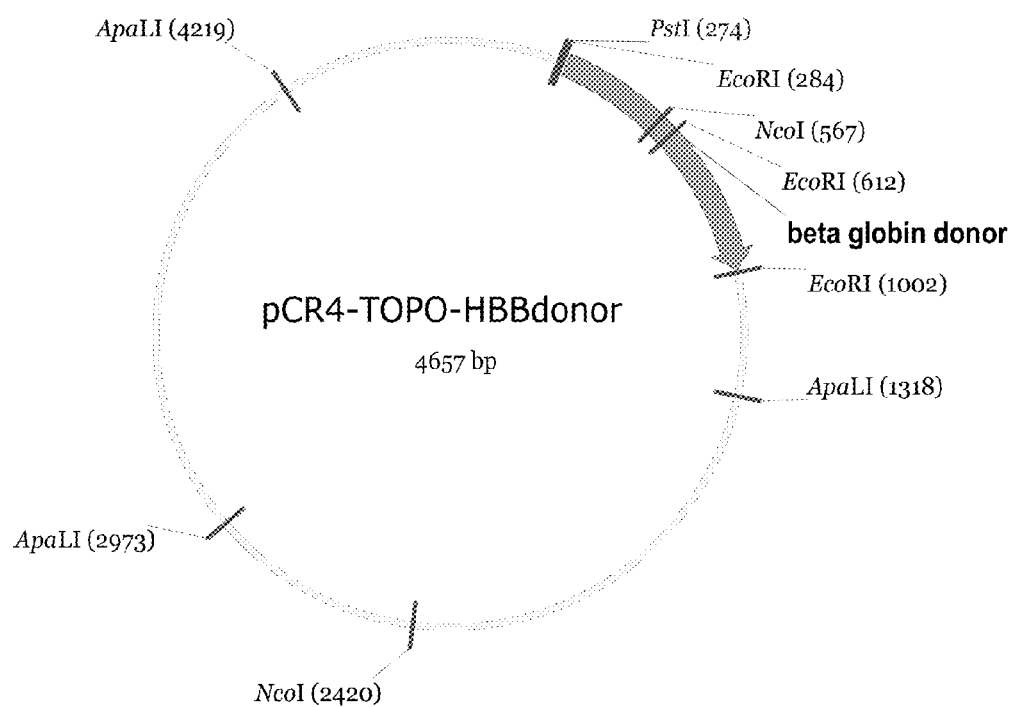
FIG. 16 is a schematic diagram of the beta globin donor construct, pCR4-TOPO-HBBdonor.

A donor DNA molecule was obtained as follows. First, a 700 base pair fragment of human genomic DNA corresponding to nucleotides 5212134-5212833 on the "−" strand of Chromosome 11 (BLAT, UCSC Human Genome site) was amplified by PCR, using genomic DNA from K562 cells as template. Sequences of primers used for amplification are shown in Table 7 (labeled initial amp 1 and initial amp 2). The resulting amplified fragment contains sequences corresponding to the promoter, the first two exons and the first intron of the human beta globin gene. See FIG. 15 for a schematic illustrating the locations of exons 1 and 2, the first intron, and the primer binding sites in the beta globin sequence. The cloned product was then further modified by PCR to introduce a set of sequence changes between nucleotides 305-336 (as shown in FIG. 13), which replaced the sequence CCGTTACTGCCCTGTGGGGCAAGGT-GAACGTG (SEQ ID NO: 78) with gCGTTAgTGC-CCGAATTCCGAtcGTcAACcac (SEQ ID NO: 79) (changes in bold). Certain of these changes (shown in lowercase) were specifically engineered to prevent the ZFP/FokI fusion proteins from binding to and cleaving the donor sequence, once integrated into the chromosome. In addition, all of the sequence changes enable discrimination between donor and endogenous chromosomal sequences following recombination. The resulting 700 base pair fragment was cloned into pCR4-TOPO, which does not contain any sequences homologous to the human genome (FIG. 16).

$CO_2$. At 72 hours after transfection, genomic DNA was isolated from the cells, and 200 ng was used as template for PCR amplification, using one primer complementary to a region of the gene outside of its region of homology with the donor sequences (nucleotides 5212883-5212905 on the "−" strand of chromosome 11), and a second primer complementary to a region of the donor molecule into which distinguishing mutations were introduced into the donor sequence (see supra). The sequences of these primers are given in Table 7 (labeled "chromosome-specific" and "donor-specific," respectively). Using these two primers, an amplification product of 415 base pairs will be obtained from genomic DNA if a targeted recombination event has occurred. As a control for DNA loading, PCR reactions were also carried out using the Initial amp 1 and Initial amp 2 primers to ensure that similar levels of genomic DNA were added to each PCR reaction. Conditions for amplification were: 95° C., 2 min, followed by 40 cycles of 95° C., 30 sec, 60° C., 45 sec, 68° C., 2 min; and a final step of 68° C., 10 min.

Figure 17:
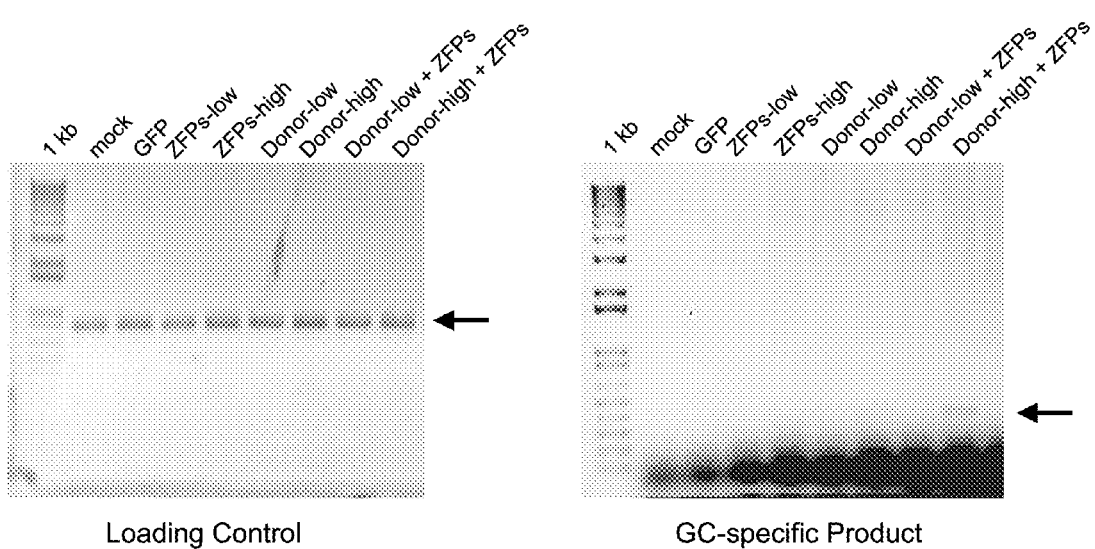
FIG. 17 shows PCR analysis of DNA from cells transfected with two pairs of β-globin-specific ZFP nucleases and a beta globin donor plasmid. The panel on the left is a loading control in which the initial amp 1 and initial amp 2 primers (Table 7) were used for amplification. In the experiment shown in the right panel, the "chromosome-specific" and "donor-specific" primers (Table 7) were used for amplification. The leftmost lane in each panel contains molecular weight markers and the next lane shows amplification products obtained from mock-transfected cells. Remaining lanes, from left to right, show amplification product from cells transfected with: a GFP-encoding plasmid, 100 ng of each ZFP/FokI-encoding plasmid, 200 ng of each ZFP/FokI-encoding plasmid, 200 ng donor plasmid, 600 ng donor plasmid, 200 ng donor plasmid+100 ng of each ZFP/FokI-encoding plasmid, and 600 ng donor plasmid+200 ng of each ZFP/FokI-encoding plasmid.

The results of this analysis (FIG. 17) indicate that a 415 base pair amplification product was obtained only with DNA extracted from cells which had been transfected with the "high" concentration of donor plasmid and both ZFP-FokI plasmids, consistent with targeted recombination of donor sequences into the chromosomal beta-globin locus.

TABLE 7

Amplification Primers for the human beta globin gene

| | |
|---|---|
| Initial amp 1 | TACTGATGGTATGGGGCCAAGAG (SEQ ID NO: 80) |
| Initial amp 2 | CACGTGCAGCTTGTCACAGTGC (SEQ ID NO: 81) |
| Chromosome-specific | TGCTTACCAAGCTGTGATTCCA (SEQ ID NO: 82) |
| Donor-specific | GGTTGACGATCGGAATTC (SEQ ID NO: 83) |

To confirm this result, the amplification product was cloned into pCR4-TOPO (Invitrogen) and its nucleotide sequence was determined. As shown in FIG. 18 (SEQ ID NO: 14), the sequence consists of a fusion between chromosomal sequences not present on the donor plasmid and sequences unique to the donor plasmid. For example, two C→G mutations which disrupt ZFP-binding are observed at positions 377 and 383 in the sequence. Nucleotides 377-408 represent sequence obtained from the donor plasmid containing the sequence changes described above; nucleotides 73-376 are sequences common to the donor and the chromosome, and nucleotides 1-72 are unique to the chromosome. The covalent linkage of donor-specific and chromosome-specific sequences in the genome confirms the successful recombination of the donor sequence at the correct locus within the genome of K562 cells.

Example 4: ZFP-FokI Linker (ZC Linker) Optimization

In order to test the effect of ZC linker length on cleavage efficiency, a four-finger ZFP binding domain was fused to a FokI cleavage half-domain, using ZC linkers of various lengths. The target site for the ZFP is 5'-AACTCGGATAAT-3' (SEQ ID NO:84) and the amino acid sequences of the recognition regions (positions −1 through +6 with respect to the start of the alpha-helix) of each of the zinc fingers were as follows (wherein F1 is the N-most, and F4 is the C-most zinc finger):

```
F1:
                              (SEQ ID NO: 85)
DRSTLIE

F2:
                              (SEQ ID NO: 86)
SSSNLSR

F3:
                              (SEQ ID NO: 87)
RSDDLSK

F4:
                              (SEQ ID NO: 88)
DNSNRIK
```

ZFP-FokI fusions, in which the aforementioned ZFP binding domain and a FokI cleavage half-domain were separated by 2, 3, 4, 5, 6, or 10 amino acid residues, were constructed. Each of these proteins was tested for cleavage of substrates having an inverted repeat of the ZFP target site, with repeats separated by 4, 5, 6, 7, 8, 9, 12, 15, 16, 17, 22, or 26 basepairs.

The amino acid sequences of the fusion constructs, in the region of the ZFP-FokI junction (with the ZC linker sequence underlined), are as follows:

```
10-residue linker
                              (SEQ ID NO: 89)
HTKIHLRQKDAARGSQLV 6-residue linker
                              (SEQ ID NO: 90)
HTKIHLRQKGSQLV 5-residue linker
                              (SEQ ID NO: 91)
HTKIHLRQGSQLV 4-residue linker
                              (SEQ ID NO: 92)
HTKIHLRGSQLV 3-residue linker
                              (SEQ ID NO: 93)
HTKIHLGSQLV 2-residue linker
                              (SEQ ID NO: 94)
HTKIHGSQLV
```

The sequences of the various cleavage substrates, with the ZFP target sites underlined, are as follows:

```
4bp separation
                              (SEQ ID NO: 95)
CTAGCATTATCCGAGTTACACAACTCGGATAATGCTAG
GATCGTAATAGGCTCAATGTGTTGAGCCTATTACGATC 5bp separation
                              (SEQ ID NO: 96)
CTAGCATTATCCGAGTTCACACAACTCGGATAATGCTAG
GATCGTAATAGGCTCAAGTGTGTTGAGCCTATTACGATC 6bp separation
                              (SEQ ID NO: 97)
CTAGGCATTATCCGAGTTCACCACAACTCGGATAATGACTAG
GATCCGTAATAGGCTCAAGTGGTGTTGAGCCTATTACTGATC 7bp separation
                              (SEQ ID NO: 98)
CTAGCATTATCCGAGTTCACACACAACTCGGATAATGCTAG
GATCGTAATAGGCTCAAGTGTGTGTTGAGCCTATTACGATC 8bp separation
                              (SEQ ID NO: 99)
CTAGCATTATCCGAGTTCACCACACAACTCGGATAATGCTAG
GATCGTAATAGGCTCAAGTGGTGTGTTGAGCCTATTACGATC 9bp separation
                              (SEQ ID NO: 100)
CTAGCATTATCCGAGTTCACACACACAACTCGGATAATGCTAG
GATCGTAATAGGCTCAAGTGTGTGTGTTGAGCCTATTACGATC 12bp separation
                              (SEQ ID NO: 101)
CTAGCATTATCCGAGTTCACCACCAACACAACTCGGATAATGCTAG
GATCGTAATAGGCTCAAGTGGTGGTTGTGTTGAGCCTATTACGATC 15bp separation
                              (SEQ ID NO: 102)
CTAGCATTATCCGAGTTCACCACCAACCACACAACTCGGATAATGC
TAGGATCGTAATAGGCTCAAGTGGTGGTTGGTGTGTTGAGCCTATT
ACGATC 16bp separation
                              (SEQ ID NO: 103)
CTAGCATTATCCGAGTTCACCACCAACCACACCAACTCGGATAATG
CTAGGATCGTAATAGGCTCAAGTGGTGGTTGGTGTGGTTGAGCCTA
TTACGATC 17bp separation
                              (SEQ ID NO: 104)
CTAGCATTATCCGAGTTCAACCACCAACCACACCAACTCGGATAATG
CTAGGATCGTAATAGGCTCAAGTTGGTGGTTGGTGTGGTTGAGCCTA
TTACGATC 22bp separation
                              (SEQ ID NO: 105)
CTAGCATTATCCGAGTTCAACCACCAACCACACCAACACAACTCGGAT
AATGCTAGGATCGTAATAGGCTCAAGTTGGTGGTTGGTGTGGTTGTGT
TGAGCCTATTACGATC 26bp separation
                              (SEQ ID NO: 106)
CTAGCATTATCCGAGTTCAACCACCAACCACACCAACACACCAACTC
GGATAATGCTAGGATCGTAATAGGCTCAAGTTGGTGGTTGGTGTGGTT
GTGGTGGTTGAGCCTATTACGATC
```

Plasmids encoding the different ZFP-FokI fusion proteins (see above) were constructed by standard molecular biological techniques, and an in vitro coupled transcription/translation system was used to express the encoded proteins. For each construct, 200 ng linearized plasmid DNA was incubated in 20 µL TnT mix and incubated at 30° C. for 1 hour and 45 minutes. TnT mix contains 100 µl TnT lysate (Promega, Madison, Wis.) with 4 µl T7 RNA polymerase (Promega)+2 µl Methionine (1 mM)+2.5 µl $ZnCl_2$ (20 mM).

For analysis of DNA cleavage by the different ZFP-FokI fusions, 1 ul of the coupled transcription/translation reaction mixture was combined with approximately 1 ng DNA substrate (end-labeled with $^{32}P$ using T4 polynucleotide kinase), and the mixture was diluted to a final volume of 19 µl with FokI Cleavage Buffer. FokI Cleavage buffer contains 20 mM Tris-HCl pH 8.5, 75 mM NaCl, 10 µM $ZnCl_2$, 1 mM DTT, 5% glycerol, 500 µg/ml BSA. The mixture was incubated for 1 hour at 37° C. 6.5 µl of FokI buffer, also containing 8 mM $MgCl_2$, was then added and incubation was continued for one hour at 37° C. Protein was extracted by adding 10 µl phenol-chloroform solution to each reaction, mixing, and centrifuging to separate the phases. Ten microliters of the aqueous phase from each reaction was analyzed by electrophoresis on a 10% polyacrylamide gel.

The gel was subjected to autoradiography, and the cleavage efficiency for each ZFP-FokI fusion/substrate pair was calculated by quantifying the radioactivity in bands corresponding to uncleaved and cleaved substrate, summing to obtain total radioactivity, and determining the percentage of the total radioactivity present in the bands representing cleavage products.

The results of this experiment are shown in Table 8. This data allows the selection of a ZC linker that provides optimum cleavage efficiency for a given target site separation. This data also allows the selection of linker lengths that allow cleavage at a selected pair of target sites, but discriminate against cleavage at the same or similar ZFP target sites that have a separation that is different from that at the intended cleavage site.

TABLE 8

DNA cleavage efficiency for various ZC linker lengths and various binding site separations*

| | 2-residue | 3-residue | 4-residue | 5-residue | 6-residue | 10-residue |
|---|---|---|---|---|---|---|
| 4 bp | 74% | 81% | 74% | 12% | 6% | 4% |
| 5 bp | 61% | 89% | 92% | 80% | 53% | 40% |
| 6 bp | 78% | 89% | 95% | 91% | 93% | 76% |
| 7 bp | 15% | 55% | 80% | 80% | 70% | 80% |
| 8 bp | 0% | 0% | 8% | 11% | 22% | 63% |
| 9 bp | 2% | 6% | 23% | 9% | 13% | 51% |
| 12 bp | 8% | 12% | 22% | 40% | 69% | 84% |
| 15 bp | 73% | 78% | 97% | 92% | 95% | 88% |
| 16 bp | 59% | 89% | 100% | 97% | 90% | 86% |
| 17 bp | 5% | 22% | 77% | 71% | 85% | 82% |
| 22 bp | 1% | 3% | 5% | 8% | 18% | 58% |
| 26 bp | 1% | 2% | 35% | 36% | 84% | 78% |

*The columns represent different ZFP-FokI fusion constructs with the indicated number of residues separating the ZFP and the FokI cleavage half-domain. The rows represent different DNA substrates with the indicated number of basepairs separating the inverted repeats of the ZFP target site.

For ZFP-FokI fusions with four residue linkers, the amino acid sequence of the linker was also varied. In separate constructs, the original LRGS linker sequence (SEQ ID NO:107) was changed to LGGS (SEQ ID NO:108), TGGS (SEQ ID NO:109), GGGS (SEQ ID NO:110), LPGS (SEQ ID NO:111), LRKS (SEQ ID NO:112), and LRWS (SEQ ID NO:113); and the resulting fusions were tested on substrates having a six-basepair separation between binding sites. Fusions containing the LGGS (SEQ ID NO:108) linker sequence were observed to cleave more efficiently than those containing the original LRGS sequence (SEQ ID NO:107). Fusions containing the LRKS (SEQ ID NO:112) and LRWS (SEQ ID NO:113) sequences cleaved with less efficiency than the LRGS sequence (SEQ ID NO:107), while the cleavage efficiencies of the remaining fusions were similar to that of the fusion comprising the original LRGS sequence (SEQ ID NO:107).

Example 5: Increased Cleavage Specificity Resulting from Alteration of the FokI Cleavage Half-Domain in the Dimerization Interface A pair of ZFP/FokI fusion proteins (denoted 5-8 and 5-10) were designed to bind to target sites in the fifth exon of the IL-2Rγ gene, to promote cleavage in the region between the target sites. The relevant region of the gene, including the target sequences of the two fusion proteins, is shown in FIG. 19. The amino acid sequence of the 5-8 protein is shown in FIG. 20, and the amino acid sequence of the 5-10 protein is shown in FIG. 21. Both proteins contain a 10 amino acid ZC linker. With respect to the zinc finger portion of these proteins, the DNA target sequences, as well as amino acid sequences of the recognition regions in the zinc fingers, are given in Table 9.

TABLE 9

Zinc Finger Designs for the IL2Rγ Gene

| Fusion | Target sequence | F1 | F2 | F3 | F4 |
|---|---|---|---|---|---|
| 5-8 | ACTCTGTGGAAG (SEQ ID NO: 114) | RSDNLSE (SEQ ID NO: 115) | RNAHRIN (SEQ ID NO: 116) | RSDTLSE (SEQ ID NO: 117) | ARSTRTT (SEQ ID NO: 118) |
| 5-10 | AACACGaAACGTG (SEQ ID NO: 119) | RSDSLSR (SEQ ID NO: 120) | DSSNRKT (SEQ ID NO: 121) | RSDSLSV (SEQ ID NO: 122) | DRSNRIT (SEQ ID NO: 123) |

Note:

The zinc finger amino acid sequences shown above (in one-letter code) represent residues -1 through +6, with respect to the start of the alpha-helical portion of each zinc finger. Finger F1 is closest to the amino terminus of the protein.

The ability of this pair of fusion proteins to catalyze specific cleavage of DNA between their target sequences (see FIG. 19) was tested in vitro using a labeled DNA template containing the target sequence and assaying for the presence of diagnostic digestion products. Specific cleavage was obtained when both proteins were used (Table 10, first row). However, the 5-10 fusion protein (comprising a wild-type FokI cleavage half-domain) was also capable of aberrant cleavage at a non-target site in the absence of the 5-8 protein (Table 10, second row), possibly due to self-dimerization.

Accordingly, 5-10 was modified in its FokI cleavage half-domain by converting amino acid residue 490 from glutamic acid (E) to lysine (K). (Numbering of amino acid residues in the FokI protein is according to Wah et al., supra.) This modification was designed to prevent homodimerization by altering an amino acid residue in the dimerization interface. The 5-10 (E490K) mutant, unlike the parental 5-10 protein, was unable to cleave at aberrant sites in the absence of the 5-8 fusion protein (Table 10, Row 3). However, the 5-10 (E490K) mutant, together with the 5-8 protein, catalyzed specific cleavage of the substrate (Table 10, Row 4). Thus, alteration of a residue in the cleavage half-domain of 5-10, that is involved in dimerization, prevented aberrant cleavage by this fusion protein due to self-dimerization. An E490R mutant also exhibits lower levels of homodimerization than the parent protein.

In addition, the 5-8 protein was modified in its dimerization interface by replacing the glutamine (Q) residue at position 486 with glutamic acid (E). This 5-8 (Q486E) mutant was tested for its ability to catalyze targeted cleavage in the presence of either the wild-type 5-10 protein or the 5-10 (E490K) mutant. DNA cleavage was not observed when the labeled substrate was incubated in the presence of both 5-8 (Q486E) and wild-type 5-10 (Table 10, Row 5). However, cleavage was obtained when the 5-8 (Q486E) and 5-10 (E490K) mutants were used in combination (Table 10, Row 6).

These results indicate that DNA cleavage by a ZFP/FokI fusion protein pair, at regions other than that defined by the target sequences of the two fusion proteins, can be minimized or abolished by altering the amino acid sequence of the cleavage half-domain in one or both of the fusion proteins.

TABLE 10

DNA cleavage by ZFP/FokI fusion protein pairs containing wild-type and mutant cleavage half-domains

| | ZFP 5-8 binding domain | ZFP 5-10 binding domain | DNA cleavage |
|---|---|---|---|
| 1 | Wild-type FokI | Wild-type FokI | Specific |
| 2 | Not present | Wild-type FokI | Non-specific |
| 3 | Not present | FokI E490K | None |
| 4 | Wild-type FokI | FokI E490K | Specific |
| 5 | FokI Q486E | Wild-type FokI | None |
| 6 | FokI Q486E | FokI E490K | Specific |

Note:
Each row of the table presents results of a separate experiment in which ZFP/FokI fusion proteins were tested for cleavage of a labeled DNA substrate. One of the fusion proteins contained the 5-8 DNA binding domain, and the other fusion protein contained the 5-10 DNA binding domain (See Table 9 and FIG. 19). The cleavage half-domain portion of the fusion proteins was as indicated in the Table. Thus, the entries in the ZFP 5-8 column indicate the type of FokI cleavage domain fused to ZFP 5-8; and the entries in the ZFP 5-10 column indicates the type of FokI cleavage domain fused to ZFP 5-10. For the FokI cleavage half-domain mutants, the number refers to the amino acid residue in the FokI protein; the letter preceding the number refers to the amino acid present in the wild-type protein and the letter following the number denotes the amino acid to which the wild-type residue was changed in generating the modified protein.
'Not present' indicates that the entire ZFP/FokI fusion protein was omitted from that particular experiment.
The DNA substrate used in this experiment was an approximately 400 bp PCR product containing the target sites for both ZFP 5-8 and ZFP 5-10. See FIG. 19 for the sequences and relative orientation of the two target sites.

Example 6: Generation of a Defective Enhanced Green Fluorescent Protein (eGFP) Gene The enhanced Green Fluorescent Protein (eGFP) is a modified form of the Green Fluorescent Protein (GFP; see, e.g., Tsien (1998) *Ann. Rev. Biochem.* 67:509-544) containing changes at amino acid 64 (phe to leu) and 65 (ser to thr). Heim et al. (1995) *Nature* 373:663-664; Cormack et al. (1996) *Gene* 173:33-38. An eGFP-based reporter system was constructed by generating a defective form of the eGFP gene, which contained a stop codon and a 2-bp frameshift mutation. The sequence of the eGFP gene is shown in FIG. 22. The mutations were inserted by overlapping PCR mutagenesis, using the Platinum® Taq DNA Polymerase High Fidelity kit (Invitrogen) and the oligonucleotides GFP-Bam, GFP-Xba, stop sense2, and stop anti2 as primers (oligonucleotide sequences are listed below in Table 11). GFP-Bam and GFP-Xba served as the external primers, while the primers stop sense2 and stop anti2 served as the internal primers encoding the nucleotide changes. The peGFP-NI vector (BD Biosciences), encoding a full-length eGFP gene, was used as the DNA template in two separate amplification reactions, the first utilizing the GFP-Bam and stop anti2 oligonucleotides as primers and the second using the GFP-Xba and stop sense2 oligonucleotides as primers. This generated two amplification products whose sequences overlapped. These products were combined and used as template in a third amplification reaction, using the external GFP-Bam and GFP-Xba oligonucleotides as primers, to regenerate a modified eGFP gene in which the sequence GACCACAT (SEQ ID NO: 124) at nucleotides 280-287 was replaced with the sequence TAACAC (SEQ ID NO: 125). The PCR conditions for all amplification reactions were as follows: the template was initially denatured for 2 minutes at 94 degrees and followed by 25 cycles of amplification by incubating the reaction for 30 sec. at 94 degrees C., 45 sec. at 46 degrees C., and 60 sec. at 68 degrees C. A final round of extension was carried out at 68 degrees C. for 10 minutes. The sequence of the final amplification product is shown in FIG. 23. This 795 bp fragment was cloned into the pCR(R) 4-TOPO vector using the TOPO-TA cloning kit (Invitrogen) to generate the pCR(R)4-TOPO-GFPmut construct.

TABLE 11

Oligonucleotide sequences for GFP

| Oligo | sequence 5'-3' |
|---|---|
| GFP-Bam | CGAATTCTGCAGTCGAC (SEQ ID NO: 126) |
| GFP-Xba | GATTATGATCTAGAGTCG (SEQ ID NO: 127) |
| stop sense2 | AGCCGCTACCCCTAACACGAAGCAG (SEQ ID NO: 128) |
| stop anti2 | CTGCTTCGTGTTAGGGGTAGCGGCT (SEQ ID NO: 129) |

Example 7: Design and Assembly of Zinc Finger Nucleases Targeting eGFP

Two three-finger ZFPs were designed to bind a region of the mutated GFP gene (Example 6) corresponding to nucleotides 271-294 (numbering according to FIG. 23). The binding sites for these proteins occur in opposite orientation with 6 base pairs separating the two binding sites. See FIG. 23. ZFP 287A binds nucleotides 271-279 on the non-coding strand, while ZFP 296 binds nucleotides 286-294 on the coding strand. The DNA target and amino acid sequence for the recognition regions of the ZFPs are listed below, and in Table 12:

```
287A:
F1 (GCGg)
                                    (SEQ ID NO: 130)
RSDDLTR

F2 (GTA)
                                    (SEQ ID NO: 131)
QSGALAR

F3 (GGG)
                                    (SEQ ID NO: 132)
RSDHLSR

296S:
F1 (GCA)
                                    (SEQ ID NO: 133)
QSGSLTR

F2 (GCA)
                                    (SEQ ID NO: 134)
QSGDLTR

F3 (GAA)
                                    (SEQ ID NO: 135)
QSGNLAR
```

TABLE 12

Zinc finger designs for the GFP gene

| Protein | Target sequence | F1 | F2 | F3 |
|---|---|---|---|---|
| 287A | GGGGTAGCGg (SEQ ID NO: 136) | RSDDLTR (SEQ ID NO: 137) | QSGALAR (SEQ ID NO: 138) | RSDHLSR (SEQ ID NO: 139) |
| 296S | GAAGCAGCA (SEQ ID NO: 140) | QSGSLTR (SEQ ID NO: 141) | QSGDLTR (SEQ ID NO: 142) | QSGNLAR (SEQ ID NO: 143) |

Note:
The zinc finger amino acid sequences shown above (in one-letter code) represent residues −1 through +6, with respect to the start of the alpha-helical portion of each zinc finger. Finger F1 is closest to the amino terminus of the protein, and Finger F3 is closest to the carboxy terminus.

Sequences encoding these proteins were generated by PCR assembly (e.g., U.S. Pat. No. 6,534,261), cloned between the KpnI and BamHI sites of the pcDNA3.1 vector (Invitrogen), and fused in frame with the catalytic domain of the FokI endonuclease (amino acids 384-579 of the sequence of Looney et al. (1989) *Gene* 80:193-208). The resulting constructs were named pcDNA3.1-GFP287-FokI and pcDNA3.1-GFP296-FokI (FIG. 24).

Example 8: Targeted In Vitro DNA Cleavage by Designed Zinc Finger Nucleases

The pCR(R)4-TOPO-GFPmut construct (Example 6) was used to provide a template for testing the ability of the 287 and 296 zinc finger proteins to specifically recognize their target sites and cleave this modified form of eGFP in vitro.

A DNA fragment containing the defective eGFP-encoding insert was obtained by PCR amplification, using the T7 and T3 universal primers and pCR(R)4-TOPO-GFPmut as template. This fragment was end-labeled using $\gamma$-$^{32}$P-ATP and T4 polynucleotide kinase. Unincorporated nucleotide was removed using a microspin G-50 column (Amersham).

An in vitro coupled transcription/translation system was used to express the 287 and 296 zinc finger nucleases described in Example 7. For each construct, 200 ng linearized plasmid DNA was incubated in 20 μL TnT mix and incubated at 30° C. for 1 hour and 45 minutes. TnT mix contains 100 μl TnT lysate (which includes T7 RNA polymerase, Promega, Madison, Wis.) supplemented with 2 μl Methionine (1 mM) and 2.5 μl ZnCl$_2$ (20 mM).

For analysis of DNA cleavage, aliquots from each of the 287 and 296 coupled transcription/translation reaction mixtures were combined, then serially diluted with cleavage buffer. Cleavage buffer contains 20 mM Tris-HCl pH 8.5, 75 mM NaCl, 10 mM MgCl$_2$, 10 μM ZnCl$_2$, 1 mM DTT, 5% glycerol, 500 μg/ml BSA. 5 μl of each dilution was combined with approximately 1 ng DNA substrate (end-labeled with $^{32}$P using T4 polynucleotide kinase as described above), and each mixture was further diluted to generate a 20 μl cleavage reaction having the following composition: 20 mM Tris-HCl pH 8.5, 75 mM NaCl, 10 mM MgCl$_2$, 10 μM ZnCl$_2$, 1 mM DTT, 5% glycerol, 500 μg/ml BSA. Cleavage reactions were incubated for 1 hour at 37° C. Protein was extracted by adding 10 μl phenol-chloroform solution to each reaction, mixing, and centrifuging to separate the phases. Ten microliters of the aqueous phase from each reaction was analyzed by electrophoresis on a 10% polyacrylamide gel.

Figure 25:
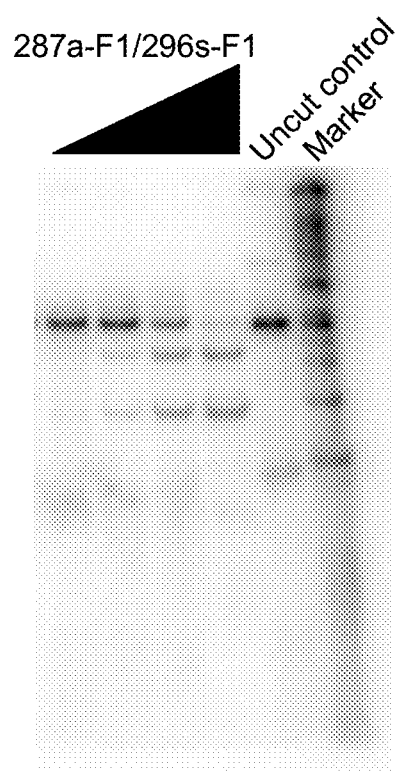
FIG. 25 shows an autoradiogram of a 10% acrylamide gel used to analyze targeted DNA cleavage of a mutant eGFP gene by zinc finger endonucleases. See Example 8 for details.

The gel was subjected to autoradiography, and the results of this experiment are shown in FIG. 25. The four left-most lanes show the results of reactions in which the final dilution of each coupled transcription/translation reaction mixture (in the cleavage reaction) was 1/156.25, 1/31.25, 1/12.5 and 1/5, respectively, resulting in effective volumes of 0.032, 0.16, 04. and 1 ul, respectively of each coupled transcription/translation reaction. The appearance of two DNA fragments having lower molecular weights than the starting fragment (lane labeled "uncut control" in FIG. 25) is correlated with increasing amounts of the 287 and 296 zinc finger endonucleases in the reaction mixture, showing that DNA cleavage at the expected target site was obtained.

Figure 26:
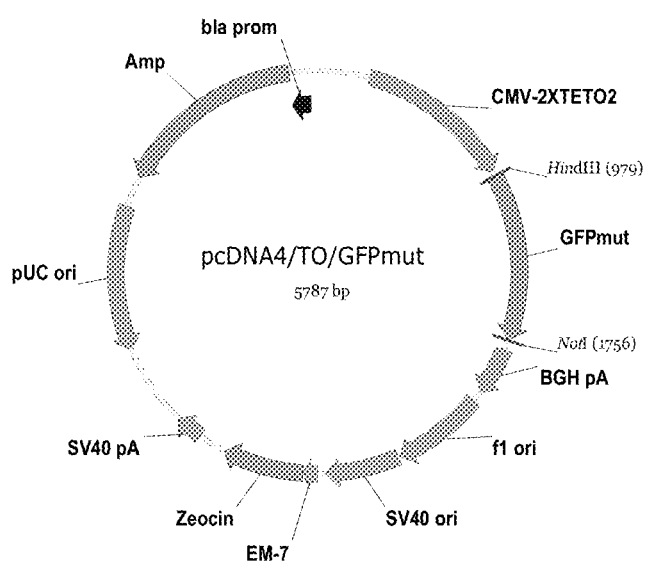
FIG. 26 shows the structure of plasmid pcDNA4/TO/GFPmut (see Example 9).

Example 9: Generation of Stable Cell Lines Containing an Integrated Defective eGFP Gene A DNA fragment encoding the mutated eGFP, eGFPmut, was cleaved out of the pCR(R)4-TOPO-GFPmut vector (Example 6) and cloned into the HindIII and NotI sites of pcDNA4/TO, thereby placing this gene under control of a tetracycline-inducible CMV promoter. The resulting plasmid was named pcDNA4/TO/GFPmut (FIG. 26). T-Rex 293 cells (Invitrogen) were grown in Dulbecco's modified Eagle's medium (DMEM) (Invitrogen) supplemented with 10% Tet-free fetal bovine serum (FBS) (HyClone). Cells were plated into a 6-well dish at 50% confluence, and two wells were each transfected with pcDNA4/TO/GFPmut. The cells were allowed to recover for 48 hours, then cells from both wells were combined and split into 10×15-cm² dishes in selective medium, i.e., medium supplemented with 400 ug/ml Zeocin (Invitrogen). The medium was changed every 3 days, and after 10 days single colonies were isolated and expanded further. Each clonal line was tested individually for doxycycline(dox)-inducible expression of the eGFPmut gene by quantitative RT-PCR (TaqMan®).

For quantitative RT-PCR analysis, total RNA was isolated from dox-treated and untreated cells using the High Pure Isolation Kit (Roche Molecular Biochemicals), and 25 ng of total RNA from each sample was subjected to real time quantitative RT-PCR to analyze endogenous gene expression, using TagMan® assays. Probe and primer sequences are shown in Table 13. Reactions were carried out on an ABI 7700 SDS machine (PerkinElmer Life Sciences) under the following conditions. The reverse transcription reaction was performed at 48° C. for 30 minutes with MultiScribe reverse transcriptase (PerkinElmer Life Sciences), followed by a 10-minute denaturation step at 95° C. Polymerase chain reaction (PCR) was carried out with AmpliGold DNA polymerase (PerkinElmer Life Sciences) for 40 cycles at 95° C. for 15 seconds and 60° C. for 1 minute. Results were analyzed using the SDS version 1.7 software and are shown in FIG. 27, with expression of the eGFPmut gene normalized to the expression of the human GAPDH gene. A number of cell lines exhibited doxycycline-dependent expression of eGFP; line 18 (T18) was chosen as a model cell line for further studies.

TABLE 13

| Oligonucleotides for mRNA analysis | |
|---|---|
| Oligonucleotide | Sequence |
| eGFP primer 1 (5T) | CTGCTGCCCGACAACCA (SEQ ID NO: 144) |
| eGFP primer 2 (3T) | CCATGTGATCGCGCTTCTC (SEQ ID NO: 145) |
| eGFP probe | CCCAGTCCGCCCTGAGCAAAGA (SEQ ID NO: 146) |
| GAPDH primer 1 | CCATGTTCGTCATGGGTGTGA (SEQ ID NO: 147) |
| GAPDH primer 2 | CATGGACTGTGGTCATGAGT (SEQ ID NO: 148) |
| GAPDH probe | TCCTGCACCACCAACTGCTTAGCA (SEQ ID NO: 149) |

Figure 28:
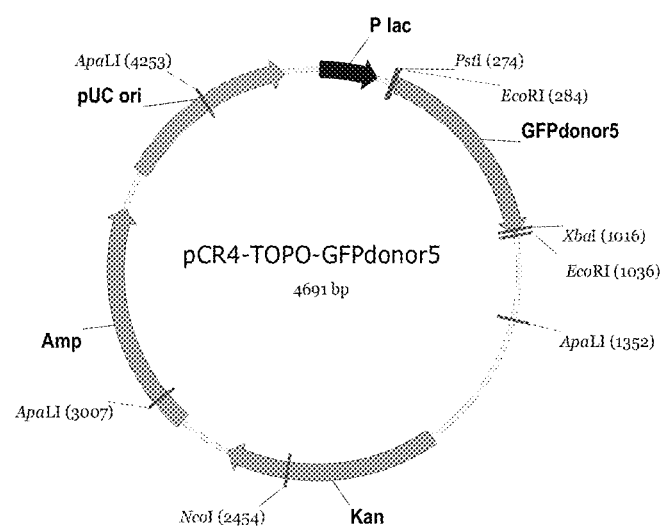
FIG. 28 shows the structure of plasmid pCR(R)4-TOPO-GFPdonor5. See Example 10 for details.

Example 10: Generation of a Donor Sequence for Correction of a Defective Chromosomal eGFP Gene A donor construct containing the genetic information for correcting the defective eGFPmut gene was constructed by PCR. The PCR reaction was carried out as described above, using the peGFP-NI vector as the template. To prevent background expression of the donor construct in targeted recombination experiments, the first 12 bp and start codon were removed from the donor by PCR using the primers GFPnostart and GFP-Xba (sequences provided in Table 14). The resulting PCR fragment (734 bp) was cloned into the pCR(R)4-TOPO vector, which does not contain a mammalian cell promoter, by TOPO-TA cloning to create pCR(R) 4-TOPO-GFPdonor5 (FIG. 28). The sequence of the eGFP insert of this construct (corresponding to nucleotides 64-797 of the sequence shown in FIG. 22) is shown in FIG. 29 (SEQ ID NO:20).

TABLE 14

| Oligonucleotides for construction of donor molecule | |
|---|---|
| Oligonucleotide | Sequence 5'-3' |
| GFPnostart | GGCGAGGAGCTGTTCAC (SEQ ID NO: 150) |
| GFP-Xba | GATTATGATCTAGAGTCG (SEQ ID NO: 151) |

Example 11: Correction of a Mutation in an Integrated Chromosomal eGFP Gene by Targeted Cleavage and Recombination The T18 stable cell line (Example 9) was transfected with one or both of the ZFP-FokI expression plasmid (pcDNA3.1-GFP287-FokI and pcDNA3.1-GFP296-FokI, Example 7) and 300 ng of the donor plasmid pCR(R)4-TOPO-GFPdonor5 (Example 10) using LipofectAMINE 2000 Reagent (Invitrogen) in Opti-MEM I reduced serum medium, according to the manufacturer's protocol. Expression of the defective chromosomal eGFP gene was induced 5-6 hours after transfection by the addition of 2 ng/ml doxycycline to the culture medium. The cells were arrested in the G2 phase of the cell cycle by the addition, at 24 hours post-transfection, of 100 ng/ml Nocodazole (FIG. 30) or 0.2 uM Vinblastine (FIG. 31). G2 arrest was allowed to continue for 24-48 hours, and was then released by the removal of the medium. The cells were washed with PBS and the medium was replaced with DMEM containing tetracycline-free FBS and 2 ng/ml doxycycline. The cells were allowed to recover for 24-48 hours, and gene correction efficiency was measured by monitoring the number of cells exhibiting eGFP fluorescence, by fluorescence-activated cell sorting (FACS) analysis. FACS analysis was carried out using a Beckman-Coulter EPICS XL-MCL instrument and System II Data Acquisition and Display software, version 2.0. eGFP fluorescence was detected by excitation at 488 nm with an argon laser and monitoring emissions at 525 nm (x-axis). Background or autofluorescence was measured by monitoring emissions at 570 nm (y-axis). Cells exhibiting high fluorescent emission at 525 nm and low emission at 570 nm (region E) were scored positive for gene correction.

Figure 30:
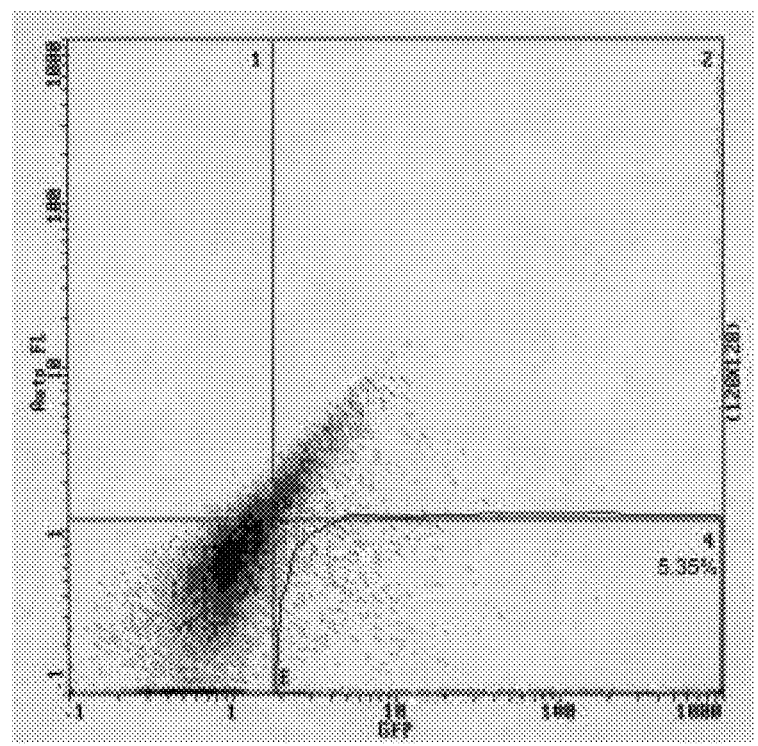
FIG. 30 shows a FACS trace of T18 cells transfected with plasmids encoding two ZFP nucleases and a plasmid encoding a donor sequence, that were arrested in the G2 phase of the cell cycle 24 hours post-transfection with 100 ng/ml nocodazole for 48 hours. The medium was replaced and the cells were allowed to recover for an additional 48 hours, and gene correction was measured by FACS analysis. See Example 11 for details.
Figure 31:
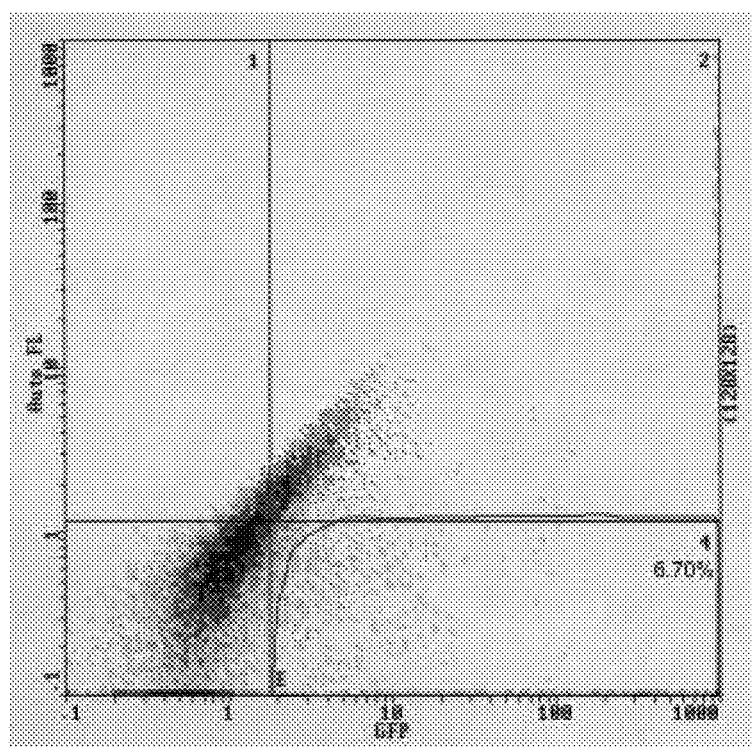
FIG. 31 shows a FACS trace of T18 cells transfected with plasmids encoding two ZFP nucleases and a plasmid encoding a donor sequence, that were arrested in the G2 phase of the cell cycle 24 hours post-transfection with 0.2 uM vinblastine for 48 hours. The medium was replaced and the cells were allowed to recover for an additional 48 hours, and gene correction was measured by FACS analysis. See Example 11 for details.

The results are summarized in Table 15 and FIGS. 30 and 31. FIGS. 30 and 31 show results in which T18 cells were transfected with the pcDNA3.1-GFP287-FokI and pcDNA3.1-GFP296-FokI plasmids encoding ZFP nucleases and the pCR(R)4-TOPO-GFPdonor5 plasmid, eGFP expression was induced with doxycycline, and cells were arrested in G2 with either nocodazole (FIG. 30) or vinblastine (FIG. 31). Both figures show FACS traces, in which cells exhibiting eGFP fluorescence are represented in the lower right-hand portion of the trace (identified as Region E, which is the portion of Quadrant 4 underneath the curve). For transfected cells that had been treated with nocodazole, 5.35% of the cells exhibited GFP fluorescence, indicative of correction of the mutant chromosomal eGFP gene (FIG. 30), while 6.7% of cells treated with vinblastine underwent eGFP gene correction (FIG. 31). These results are summarized, along with additional control experiments, in Rows 1-8 of Table 15.

In summary, these experiments show that, in the presence of two ZFP nucleases and a donor sequence, approximately 1% of treated cells underwent gene correction, and that this level of correction was increased 4-5 fold by arresting treated cells in the G2 phase of the cell cycle.

TABLE 15

Correction of a defective chromosomal eGFP gene

| Expt. | Treatment[1] | Percent cells with corrected eGFP gene[2] |
|---|---|---|
| 1 | 300 ng donor only | 0.01 |
| 2 | 100 ng ZFP 287 + 300 ng donor | 0.16 |
| 3 | 100 ng ZFP 296 + 300 ng donor | 0.6 |
| 4 | 50 ng ZFP 287 + 50 ng ZFP 296 + 300 ng donor | 1.2 |
| 5 | as 4 + 100 ng/ml nocodazole | 5.35 |
| 6 | as 4 + 0.2 uM vinblastine | 6.7 |
| 7 | no donor, no ZFP, 100 ng/ml nocodazole | 0.01 |
| 8 | no donor, no ZFP, 0.2 uM vinblastine | 0.0 |
| 9 | 100 ng ZFP287/Q486E + 300 ng donor | 0.0 |
| 10 | 100 ng ZFP296/E490K + 300 ng donor | 0.01 |
| 11 | 50 ng 287/Q486E + 50 ng 296/E490K + 300 ng donor | 0.62 |
| 12 | as 11 + 100 ng/ml nocodazole | 2.37 |
| 13 | as 11 + 0.2 uM vinblastine | 2.56 |

Notes:
[1]T18 cells, containing a defective chromosomal eGFP gene, were transfected with plasmids encoding one or two ZFP nucleases and/or a donor plasmid encoding a nondefective eGFP sequence, and expression of the chromosomal eGFP gene was induced with doxycycline. Cells were optionally arrested in G2 phase of the cell cycle after eGFP induction. FACS analysis was conducted 5 days after transfection.
[2]The number is the percent of total fluorescence exhibiting high emission at 525 nm and low emission at 570 nm (region E of the FACS trace).

Example 12: Correction of a Defective Chromosomal Gene Using Zinc Finger Nucleases with Sequence Alterations in the Dimerization Interface Zinc finger nucleases whose sequences had been altered in the dimerization interface were tested for their ability to catalyze correction of a defective chromosomal eGFP gene. The protocol described in Example 11 was used, except that the nuclease portion of the ZFP nucleases (i.e., the FokI cleavage half-domains) were altered as described in Example 5. Thus, an E490K cleavage half-domain was fused to the GFP296 ZFP domain (Table 12), and a Q486E cleavage half-domain was fused to the GFP287 ZFP (Table 12).

The results are shown in Rows 9-11 of Table 15 and indicate that a significant increase in the frequency of gene correction was obtained in the presence of two ZFP nucleases having alterations in their dimerization interfaces, compared to that obtained in the presence of either of the nucleases alone. Additional experiments, in which T18 cells were transfected with donor plasmid and plasmids encoding the 287/Q486E and 296/E490K zinc finger nucleases, then arrested in G2 with nocodazole or vinblastine, showed a further increase in frequency of gene correction, with over 2% of cells exhibiting eGFP fluorescence, indicative of a corrected chromosomal eGFP gene (Table 15, Rows 12 and 13).

Example 13: Effect of Donor Length on Frequency of Gene Correction

In an experiment similar to those described in Example 11, the effect of the length of donor sequence on frequency of targeted recombination was tested. T18 cells were transfected with the two ZFP nucleases, and eGFP expression was induced with doxycycline, as in Example 11. Cells were also transfected with either the pCR(R)4-TOPO-GFPdonor5 plasmid (FIG. 28) containing a 734 bp eGFP insert (FIG. 29) as in Example 11, or a similar plasmid containing a 1527 bp sequence insert (FIG. 32) homologous to the mutated chromosomal eGFP gene. Additionally, the effect of G2 arrest with nocodazole on recombination frequency was assessed.

In a second experiment, donor lengths of 0.7, 1.08 and 1.5 kbp were compared. T18 cells were transfected with 50 ng of the 287-FokI and 296-FokI expression plasmids (Example 7, Table 12) and 500 ng of a 0.7 kbp, 1.08 kbp, or 1.5 kbp donors, as described in Example 11. Four days after transfection, cells were assayed for correction of the defective eGFP gene by FACS, monitoring GFP fluorescence.

The results of these two experiments, shown in Table 16, show that longer donor sequence increases the frequency of targeted recombination (and, hence, of gene correction) and confirm that arrest of cells in the G2 phase of the cell cycle also increases the frequency of targeted recombination.

TABLE 16

Effect of donor length and cell-cycle arrest on targeted recombination frequency

| | Experiment 1 Nocodazole concentration: | | Experiment 2 |
|---|---|---|---|
| Donor length (kb) | 0 ng/ml | 100 ng/ml | — |
| 0.7 | 1.41 | 5.84 | 1.2 |
| 1.08 | not done | not done | 2.2 |
| 1.5 | 2.16 | 8.38 | 2.3 |

Note:
Numbers represent percentage of total flourescence in Region E of the FACS trace (see Example 11) which is an indication of the fraction of cells that have undergone targeted recombination to correct the defective chromosomal eGFP gene.

Example 14: Editing of the Endogenous Human IL-2Rγ Gene by Targeted Cleavage and Recombination Using Zinc Finger Nucleases Two expression vectors, each encoding a ZFP-nuclease targeted to the human IL-2Rγ gene, were constructed. Each ZFP-nuclease contained a zinc finger protein-based DNA binding domain (see Table 17) fused to the nuclease domain of the type IIS restriction enzyme FokI (amino acids 384-579 of the sequence of Wah et al. (1998) *Proc. Natl. Acad. Sci. USA* 95:10564-10569) via a four amino acid ZC linker (see Example 4). The nucleases were designed to bind to positions in exon 5 of the chromosomal IL-2Rγ gene surrounding codons 228 and 229 (a mutational hotspot in the gene) and to introduce a double-strand break in the DNA between their binding sites.

TABLE 17

Zinc Finger Designs for exon 5 of the IL2Rγ Gene

| Target sequence | F1 | F2 | F3 | F4 |
|---|---|---|---|---|
| ACTCTGTGGAAG (SEQ ID NO: 152) 5-8G | RSDNLSV (SEQ ID NO: 153) | RNAHRIN (SEQ ID NO: 154) | RSDTLSE (SEQ ID NO: 155) | ARSTRTN (SEQ ID NO: 156) |
| AAAGCGGCTCCG (SEQ ID NO: 157) 5-9D | RSDTLSE (SEQ ID NO: 158) | ARSTRTT (SEQ ID NO: 159) | RSDSLSK (SEQ ID NO: 160) | QRSNLKV (SEQ ID NO: 161) |

Note:
The zinc finger amino acid sequences shown above (in one-letter code) represent residues -1 through +6, with respect to the start of the alpha-helical portion of each zinc finger. Finger F1 is closest to the amino terminus of the protein.

The complete DNA-binding portion of each of the chimeric endonucleases was as follows:

```
Nuclease targeted to
                                          (SEQ ID NO: 152)
ACTCTGTGGAAG (SEQ ID NO: 162)
MAERPFQCRICMRNFSRSDNLSVHIRTHTGEKPFACDICGRKFARN
AHRINHTKIHTGSQKPFQCRICMRNFSRSDTLSEHIRTHTGEKPFA
CDICGRKFAARSTRTNHTKIHLRGS Nuclease targeted to
                                          (SEQ ID NO: 157)
AAAGCGGCTCCG (SEQ ID NO: 163)
MAERPFQCRICMRNFSRSDTLSEHIRTHTGEKPFACDICGRKFAAR
STRTTHTKIHTGSQKPFQCRICMRNFSRSDSLSKHIRTHTGEKPFA
CDICGRKFAQRSNLKVHTKIHLRGS
```

Human embryonic kidney 293 cells were transfected (Lipofectamine 2000; Invitrogen) with two expression constructs, each encoding one of the ZFP-nucleases described in the preceding paragraph. The cells were also transfected with a donor construct carrying as an insert a 1,543 bp fragment of the IL2Rγ locus corresponding to positions 69195166-69196708 of the "minus" strand of the X chromosome (UCSC human genome release July 2003), in the pCR4Blunt Topo (Invitrogen) vector. The IL-2Rγ insert sequence contained the following two point mutations in the sequence of exon 5 (underlined):

```
                                          (SEQ ID NO: 164)
      F  R  V  R  S  R  F  N  P  L  C  G  S (SEQ ID NO: 165)
      TTTCGTGTTCGGAGCCGGTTTAACCCGCTCTGTGGAAGT
```

The first mutation (CGC→CGG) does not change the amino acid sequence (upper line) and serves to adversely affect the ability of the ZFP-nuclease to bind to the donor DNA, and to chromosomal DNA following recombination. The second mutation (CCA→CCG) does not change the amino acid sequence and creates a recognition site for the restriction enzyme BsrBI.

Figure 33:
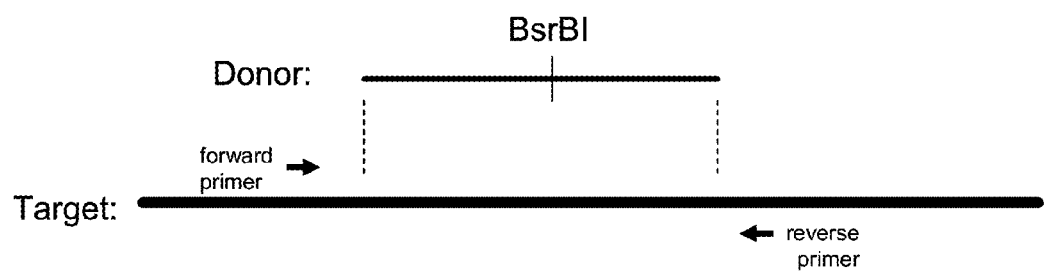
FIG. 33 shows a schematic diagram of an assay used to measure the frequency of editing of the endogenous human IL-2Rγ gene. See Example 14 for details.

Either 50 or 100 nanograms of each ZFP-nuclease expression construct and 0.5 or 1 microgram of the donor construct were used in duplicate transfections. The following control experiments were also performed: transfection with an expression plasmid encoding the eGFP protein; transfection with donor construct only; and transfection with plasmids expressing the ZFP nucleases only. Twenty four hours after transfection, vinblastine (Sigma) was added to 0.2 µM final concentration to one sample in each set of duplicates, while the other remained untreated. Vinblastine affects the cell's ability to assemble the mitotic spindle and therefore acts as a potent $G_2$ arresting agent. This treatment was performed to enhance the frequency of targeting because the homology-directed double-stranded break repair pathway is more active than non-homologous end joining in the $G_2$ phase of the cell cycle. Following a 48 hr period of treatment with 0.2 µM vinblastine, growth medium was replaced, and the cells were allowed to recover from vinblastine treatment for an additional 24 hours. Genomic DNA was then isolated from all cell samples using the DNEasy Tissue Kit (Qiagen). Five hundred nanograms of genomic DNA from each sample was then assayed for frequency of gene targeting, by testing for the presence of a new BsrBI site in the chromosomal IL-2Rγ locus, using the assay described schematically in FIG. 33.

Figure 34:
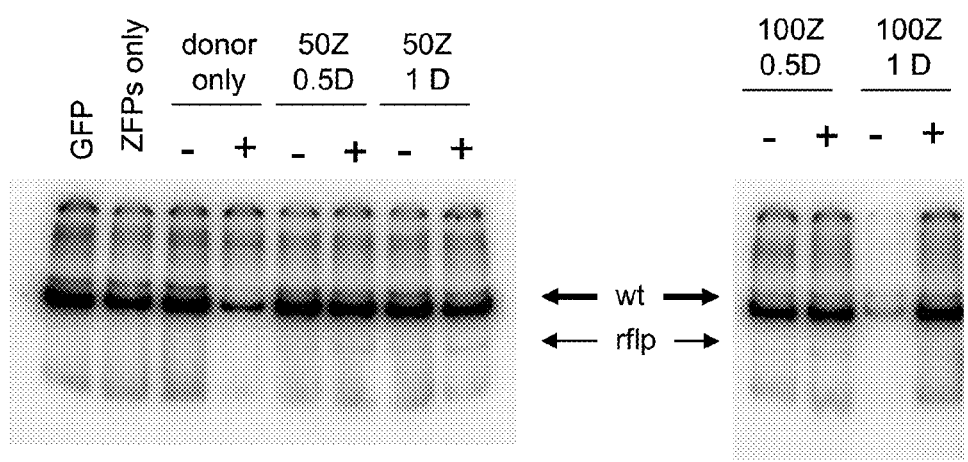
FIG. 34 shows autoradiograms of acrylamide gels used in an assay to measure the frequency of editing of an endogenous cellular gene by targeted cleavage and homologous recombination. The lane labeled "GFP" shows assay results from a control in which cells were transfected with an eGFP-encoding vector; the lane labeled "ZFPs only" shows results from another control experiment in which cells were transfected with the two ZFP/nuclease-encoding plasmids (50 ng of each) but not with a donor sequence. Lanes labeled "donor only" show results from a control experiment in which cells were transfected with 1 ug of donor plasmid but not with the ZFP/nuclease-encoding plasmids. In the experimental lanes, 50Z refers to cells transfected with 50 ng of each ZFP/nuclease expression plasmid, 100Z refers to cells transfected with 100 ng of each ZFP/nuclease expression plasmid, 0.5D refers to cells transfected with 0.5 μg of the donor plasmid, and 1D refers to cells transfected with 1.0 μg of the donor plasmid. "+" refers to cells that were exposed to 0.2 μM vinblastine; "−" refer to cells that were not exposed to vinblastine. "wt" refers to the fragment obtained after BsrBI digestion of amplification products obtained from chromosomes containing the wild-type chromosomal IL-2Rγ gene; "rflp" refers to the two fragments (of approximately equal molecular weight) obtained after BsrBI digestion of amplification products obtained from chromosomes containing sequences from the donor plasmid which had integrated by homologous recombination.

In brief, 20 cycles of PCR were performed using the primers shown in Table 18, each of which hybridizes to the chromosomal IL-2Rγ locus immediately outside of the region homologous to the 1.5 kb donor sequence. Twenty microcuries each of $\alpha\text{-}^{32}\text{P-dCTP}$ and $\alpha\text{-}^{32}\text{P-dATP}$ were included in each PCR reaction to allow detection of PCR products. The PCR reactions were desalted on a G-50 column (Amersham), and digested for 1 hour with 10 units of BsrBI (New England Biolabs). The digestion products were resolved on a 10% non-denaturing polyacrylamide gel (BioRad), and the gel was dried and autoradiographed (FIG. 34). In addition to the major PCR product, corresponding to the 1.55 kb amplified fragment of the IL2Rγ locus ("wt" in FIG. 34), an additional band ("rflp" in FIG. 34) was observed in lanes corresponding to samples from cells that were transfected with the donor DNA construct and both ZFP-nuclease constructs. This additional band did not appear in any of the control lanes, indicating that ZFP nuclease-facilitated recombination of the BsrBI RFLP-containing donor sequence into the chromosome occurred in this experiment.

Additional experiments, in which trace amounts of a RFLP-containing IL-2Rγ DNA sequence was added to human genomic DNA (containing the wild-type IL-2Rγ gene), and the resultant mixture was amplified and subjected to digestion with a restriction enzyme which cleaves at the RFLP, have indicated that as little as 0.5% RFLP-containing sequence can be detected quantitatively using this assay.

TABLE 18

Oligonucleotides for analysis of the human IL-2Rγ gene

| Oligonucleotide | Sequence |
|---|---|
| Ex5_1.5detF1 | GATTCAACCAGACAGATAGAAGG (SEQ ID NO: 166) |
| Ex5_1.5detR1 | TTACTGTCTCATCCTTTACTCC (SEQ ID NO: 167) |

Example 15: Targeted Recombination at the IL-2Rγ Locus in K562 Cells

K562 is a cell line derived from a human chronic myelogenous leukemia. The proteins used for targeted cleavage were FokI fusions to the 5-8G and 5-9D zinc finger DNA-binding domains (Example 14, Table 17). The donor sequence was the 1.5 kbp fragment of the human IL-2Rγ gene containing a BsrBI site introduced by mutation, described in Example 14.

K562 cells were cultured in RPMI Medium 1640 (Invitrogen), supplemented with 10% fetal bovine serum (FBS) (Hyclone) and 2 mM L-glutamine. All cells were maintained at 37° C. in an atmosphere of 5% $CO_2$. These cells were transfected by Nucleofection™ (Solution V, Program T16) (Amaxa Biosystems), according to the manufacturers' protocol, transfecting 2 million cells per sample. DNAs for transfection, used in various combinations as described below, were a plasmid encoding the 5-8G ZFP-FokI fusion endonuclease, a plasmid encoding the 5-9D ZFP-FokI fusion endonuclease, a plasmid containing the donor sequence (described above and in Example 14) and the peGFP-N1 vector (BD Biosciences) used as a control.

In the first experiment, cells were transfected with various plasmids or combinations of plasmids as shown in Table 19.

TABLE 19

| Sample # | p-eGFP-N1 | p5-8G | p5-9D | donor | vinblastine |
|---|---|---|---|---|---|
| 1 | 5 µg | — | — | — | — |
| 2 | — | — | — | 50 µg | — |
| 3 | — | — | — | 50 µg | yes |
| 4 | — | 10 µg | 10 µg | — | — |
| 5 | — | 5 µg | 5 µg | 25 µg | — |
| 6 | — | 5 µg | 5 µg | 25 µg | yes |
| 7 | — | 7.5 µg | 7.5 µg | 25 µg | — |
| 8 | — | 7.5 µg | 7.5 µg | 25 µg | yes |
| 9 | — | 7.5 µg | 7.5 µg | 50 µg | — |
| 10 | — | 7.5 µg | 7.5 µg | 50 µg | yes |

Vinblastine-treated cells were exposed to 0.2 uM vinblastine at 24 hours after transfection for 30 hours. The cells were collected, washed twice with PBS, and re-plated in growth medium. Cells were harvested 4 days after transfection for analysis of genomic DNA.

Genomic DNA was extracted from the cells using the DNEasy kit (Qiagen). One hundred nanograms of genomic DNA from each sample were used in a PCR reaction with the following primers:

```
Exon 5 forward:
                            (SEQ ID NO: 168)
GCTAAGGCCAAGAAAGTAGGGCTAAAG Exon 5 reverse:
                            (SEQ ID NO: 169)
TTCCTTCCATCACCAAACCCTCTTG
```

These primers amplify a 1,669 bp fragment of the X chromosome corresponding to positions 69195100-69196768 on the "−" strand (UCSC human genome release July 2003) that contain exon 5 of the IL2Rγ gene. Amplification of genomic DNA which has undergone homologous recombination with the donor DNA yields a product containing a BsrBI site; whereas the amplification product of genomic DNA which has not undergone homologous recombination with donor DNA will not contain this restriction site.

Ten microcuries each of $\alpha$-$^{32}$PdCTP and $\alpha$-$^{32}$PdATP were included in each amplification reaction to allow visualization of reaction products. Following 20 cycles of PCR, the reaction was desalted on a Sephadex G-50 column (Pharmacia), and digested with 10 Units of BsrBI (New England Biolabs) for 1 hour at 37° C. The reaction was then resolved on a 10% non-denaturing PAGE, dried, and exposed to a PhosphorImager screen.

Figure 35:
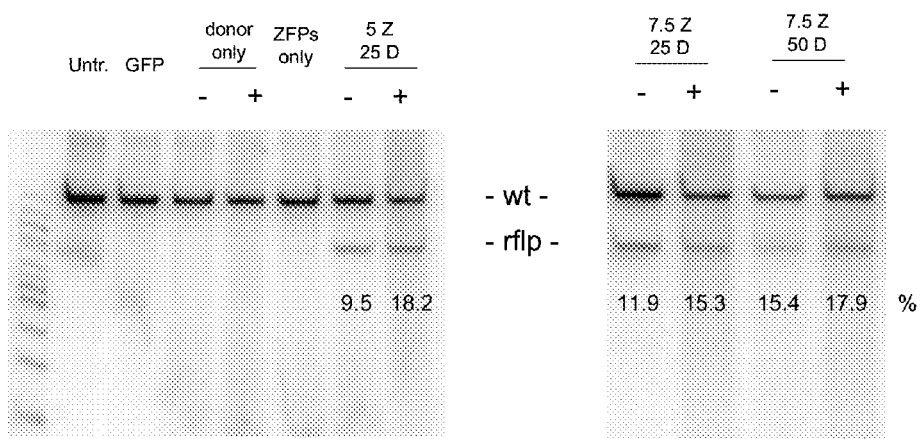
FIG. 35 shows an autoradiographic image of a four-hour exposure of a gel used in an assay to measure targeted recombination at the human IL-2Rγ locus in K562 cells. "wt" identifies a band that is diagnostic for chromosomal DNA containing the native K562 IL-2Rγ sequence; "rflp" identifies a doublet diagnostic for chromosomal DNA containing the altered IL-2Rγ sequence present in the donor DNA molecule. The symbol "+" above a lane indicates that cells were treated with 0.2 uM vinblastine; the symbol "−" indicates that cells were not treated with vinblastine. The numbers in the "ZFP+donor" lanes indicate the percentage of total chromosomal DNA containing sequence originally present in the donor DNA molecule, calculated using the "peak finder, automatic baseline" function of Molecular Dynamics' ImageQuant v. 5.1 software as described in Ch. 8 of the manufacturer's manual (Molecular Dynamics ImageQuant User's Guide; part 218-415). "Untr" indicates untransfected cells. See Example 15 for additional details.

The results of this experiment are shown in FIG. 35. When cells were transfected with the control GFP plasmid, donor plasmid alone or the two ZFP-encoding plasmids in the absence of donor, no BsrBI site was present in the amplification product, as indicated by the absence of the band marked "rflp" in the lanes corresponding to these samples in FIG. 35. However, genomic DNA of cells that were transfected with the donor plasmid and both ZFP-encoding plasmids contained the BsrBI site introduced by homologous recombination with the donor DNA (band labeled "rflp"). Quantitation of the percentage of signal represented by the RFLP-containing DNA, shown in FIG. 35, indicated that, under optimal conditions, up to 18% of all IL-2Rγ genes in the transfected cell population were altered by homologous recombination.

A second experiment was conducted according to the protocol just described, except that the cells were expanded for 10 days after transfection. DNAs used for transfection are shown in Table 20.

TABLE 20

| Sample # | p-eGFP-N1 | p5-8G | p5-9D | donor | vinblastine |
|---|---|---|---|---|---|
| 1 | 50 µg | — | — | — | — |
| 2 | — | — | — | 50 µg | — |
| 3 | — | — | — | 50 µg | yes |
| 4 | — | 7.5 µg | 7.5 µg | — | — |
| 5 | — | 5 µg | 5 µg | 25 µg | — |
| 6 | — | 5 µg | 5 µg | 25 µg | yes |
| 7 | — | 7.5 µg | 7.5 µg | 50 µg | — |
| 8 | — | 7.5 µg | 7.5 µg | 50 µg | yes |

Figure 36:
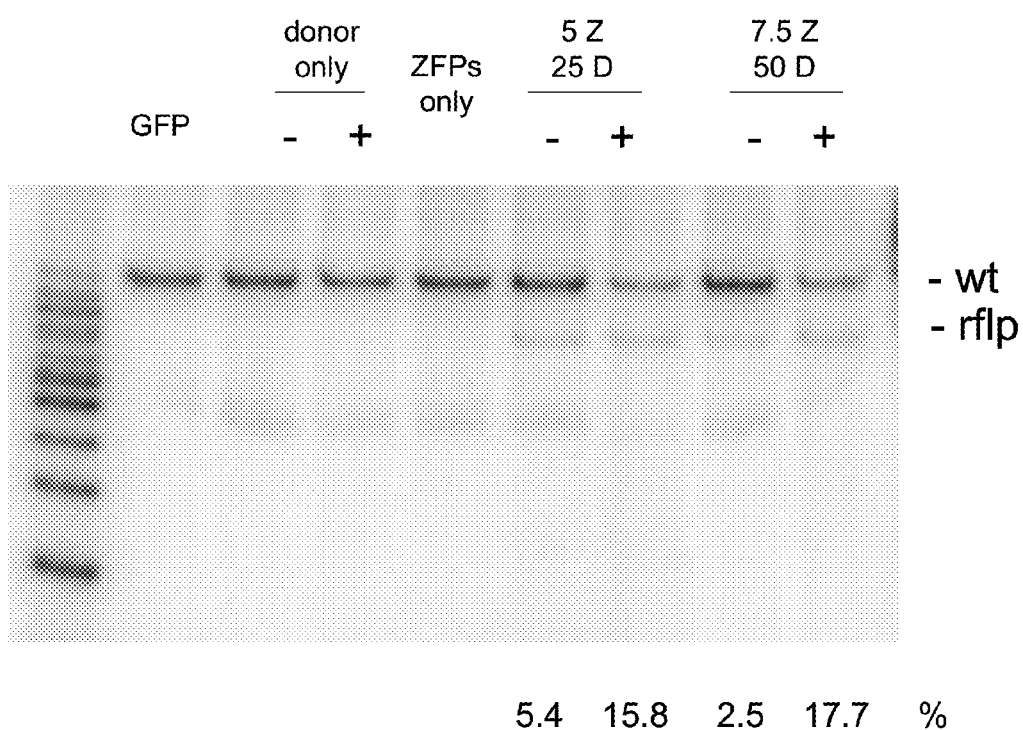
FIG. 36 shows an autoradiographic image of a four-hour exposure of a gel used in an assay to measure targeted recombination at the human IL-2Rγ locus in K562 cells. "wt" identifies a band that is diagnostic for chromosomal DNA containing the native K562 IL-2Rγ sequence; "rflp" identifies a band that is diagnostic for chromosomal DNA containing the altered IL-2Rγ sequence present in the donor DNA molecule. The symbol "+" above a lane indicates that cells were treated with 0.2 uM vinblastine; the symbol "−" indicates that cells were not treated with vinblastine. The numbers beneath the "ZFP+donor" lanes indicate the percentage of total chromosomal DNA containing sequence originally present in the donor DNA molecule, calculated as described in Example 35. See Example 15 for additional details.

Analysis of BsrBI digestion of amplified DNA, shown in FIG. 36, again demonstrated that up to 18% of IL-2Rγ genes had undergone sequence alteration through homologous recombination, after multiple rounds of cell division. Thus, the targeted recombination events are stable.

In addition, DNA from transfected cells in this second experiment was analyzed by Southern blotting. For this analysis, twelve micrograms of genomic DNA from each sample were digested with 100 units EcoRI, 50 units BsrBI, and 40 units of DpnI (all from New England Biolabs) for 12 hours at 37° C. This digestion generates a 7.7 kbp Eco RI fragment from the native IL-2Rγ gene (lacking a BsrBI site) and fragments of 6.7 and 1.0 kbp from a chromosomal IL-2Rγ gene whose sequence has been altered, by homologous recombination, to include the BsrBI site. DpnI, a methylation-dependent restriction enzyme, was included to destroy the dam-methylated donor DNA. Unmethylated K562 cell genomic DNA is resistant to DpnI digestion.

Following digestion, genomic DNA was purified by phenol-chloroform extraction and ethanol precipitation, resuspended in TE buffer, and resolved on a 0.8% agarose gel along with a sample of genomic DNA digested with EcoRI and SphI to generate a size marker. The gel was processed for alkaline transfer following standard procedure and DNA was transferred to a nylon membrane (Schleicher and Schuell). Hybridization to the blot was then performed by using a radiolabelled fragment of the IL-2Rγ locus corresponding to positions 69198428-69198769 of the "−" strand of the X chromosome (UCSC human genome July 2003 release). This region of the gene is outside of the region homologous to donor DNA. After hybridization, the membrane was exposed to a PhosphorImager plate and the data quantitated using Molecular Dynamics software. Alteration of the chromosomal IL-2Rγ sequence was measured by analyzing the intensity of the band corresponding to the EcoRI-BsrBI fragment (arrow next to autoradiograph; BsrBI site indicated by filled triangle in the map above the autoradiograph).

Figure 37:
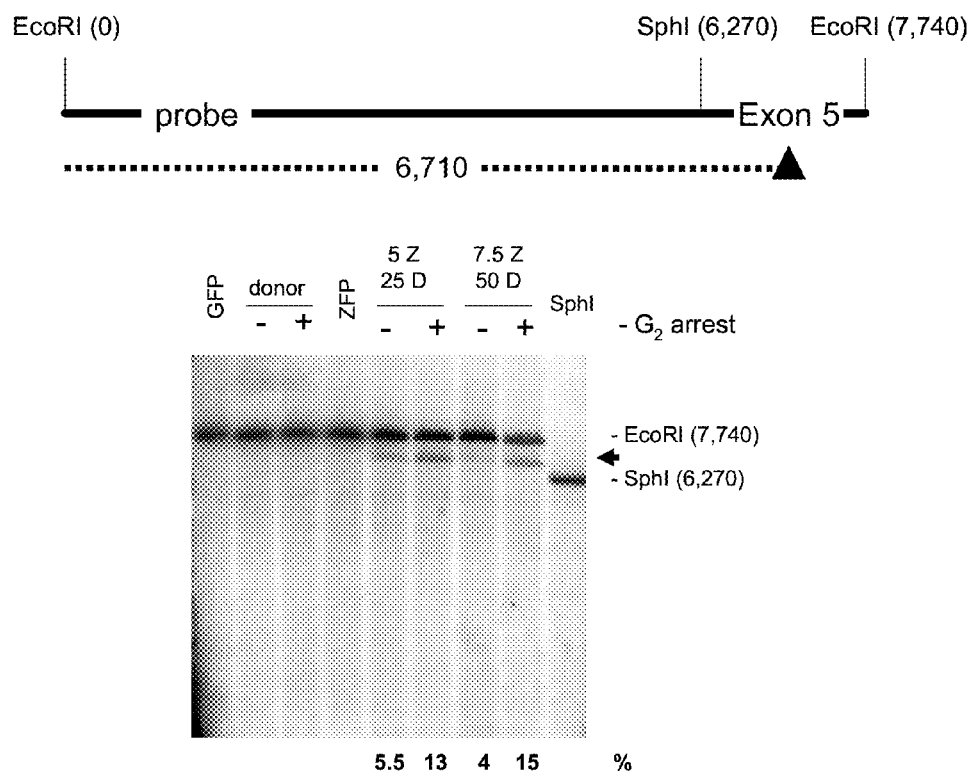
FIG. 37 shows an autoradiogram of a four-hour exposure of a DNA blot probed with a fragment specific to the human IL-2Rγ gene. The arrow to the right of the image indicates the position of a band corresponding to genomic DNA whose sequence has been altered by homologous recombination. The symbol "+" above a lane indicates that cells were treated with 0.2 uM vinblastine; the symbol "−" indicates that cells were not treated with vinblastine. The numbers beneath the "ZFP+donor" lanes indicate the percentage of total chromosomal DNA containing sequence originally present in the donor DNA molecule, calculated as described in Example 35. See Example 15 for additional details.

The results, shown in FIG. 37, indicate up to 15% of chromosomal IL-2Rγ sequences were altered by homologous recombination, thereby confirming the results obtained by PCR analysis that the targeted recombination event was stable through multiple rounds of cell division. The Southern blot results also indicate that the results shown in FIG. 36 do not result from an amplification artifact.

Example 16: Targeted Recombination at the IL-2Rγ Locus in CD34-Positive Hematopoietic Stem Cells Genetic diseases (e.g., severe combined immune deficiency (SCID) and sickle cell anemia) can be treated by homologous recombination-mediated correction of the specific DNA sequence alteration responsible for the disease. In certain cases, maximal efficiency and stability of treatment would result from correction of the genetic defect in a pluripotent cell. To this end, this example demonstrates alteration of the sequence of the IL-2Rγ gene in human CD34-positive bone marrow cells. CD34+ cells are pluripotential hematopoietic stem cells which give rise to the erythroid, myeloid and lymphoid lineages.

Bone marrow-derived human CD34 cells were purchased from AllCells, LLC and shipped as frozen stocks. These cells were thawed and allowed to stand for 2 hours at 37° C. in an atmosphere of 5% $CO_2$ in RPMI Medium 1640 (Invitrogen), supplemented with 10% fetal bovine serum (FBS) (Hyclone) and 2 mM L-glutamine. Cell samples ($1 \times 10^6$ or $2 \times 10^6$ cells) were transfected by Nucleofection™ (amaxa biosystems) using the Human CD34 Cell Nucleofector™ Kit, according to the manufacturers' protocol. After transfection, cells were cultured in RPMI Medium 1640 (Invitrogen), supplemented with 10% FBS, 2 mM L-glutamine, 100 ng/ml granulocyte-colony stimulating factor (G-CSF), 100 ng/ml stem cell factor (SCF), 100 ng/ml thrombopoietin (TPO), 50 ng/ml Flt3 Ligand, and 20 ng/ml Interleukin-6 (IL-6). The caspase inhibitor zVAD-FMK (Sigma-Aldrich) was added to a final concentration of 40 uM in the growth medium immediately after transfection to block apoptosis. Additional caspase inhibitor was added 48 hours later to a final concentration of 20 uM to further prevent apoptosis. These cells were maintained at 37° C. in an atmosphere of 5% $CO_2$ and were harvested 3 days post-transfection.

Cell numbers and DNAs used for transfection are shown in Table 21.

TABLE 21

| Sample | # cells | p-eGFP-N1[1] | Donor[2] | p5-8G[3] | p5-9D[3] |
|---|---|---|---|---|---|
| 1 | $1 \times 10^6$ | 5 ug | — | — | — |
| 2 | $2 \times 10^6$ | — | 50 ug | — | — |
| 3 | $2 \times 10^6$ | — | 50 ug | 7.5 ug | 7.5 ug |

[1]This is a control plasmid encoding an enhanced green fluorescent protein.
[2]The donor DNA is a 1.5 kbp fragment containing sequences from exon 5 of the IL-2Rγ gene with an introduced BsrBI site (see Example 14).
[3]These are plasmids encoding FokI fusions with the 5-8 G and 5-9D zinc finger DNA binding domains (see Table 17).

Genomic DNA was extracted from the cells using the MasterPure DNA Purification Kit (Epicentre). Due to the presence of glycogen in the precipitate, accurate quantitation of this DNA used as input in the PCR reaction is impossible; estimates using analysis of ethidium bromide-stained agarose gels indicate that ca. 50 ng genomic DNA was used in each sample. Thirty cycles of PCR were then performed using the following primers, each of which hybridizes to the chromosomal IL-2Rγ locus immediately outside of the region homologous to the 1.5 kb donor:

```
ex5_1.5detF3
                              (SEQ ID NO: 170)
GCTAAGGCCAAGAAAGTAGGGCTAAAG ex5_1.5detR3
                              (SEQ ID NO: 171)
TTCCTTCCATCACCAAACCCTCTTG
```

Twenty microcuries each of $\alpha$-$^{32}$PdCTP and $\alpha$-$^{32}$PdATP were included in each PCR reaction to allow detection of PCR products. To provide an in-gel quantitation reference, the existence of a spontaneously occurring SNP in exon 5 of the IL-2Rgamma gene in Jurkat cells was exploited: this SNP creates a RFLP by destroying a MaeII site that is present in normal human DNA. A reference standard was therefore created by adding 1 or 10 nanograms of normal human genomic DNA (obtained from Clontech, Palo Alto, Calif.) to 100 or 90 ng of Jurkat genomic DNA, respectively, and performing the PCR as described above. The PCR reactions were desalted on a G-50 column (Amersham), and digested for 1 hour with restriction enzyme: experimental samples were digested with 10 units of BsrBI (New England Biolabs); the "reference standard" reactions were digested with MaeII. The digestion products were resolved on a 10% non-denaturing PAGE (BioRad), the gel dried and analyzed by exposure to a PhosphorImager plate (Molecular Dynamics).

Figure 38:
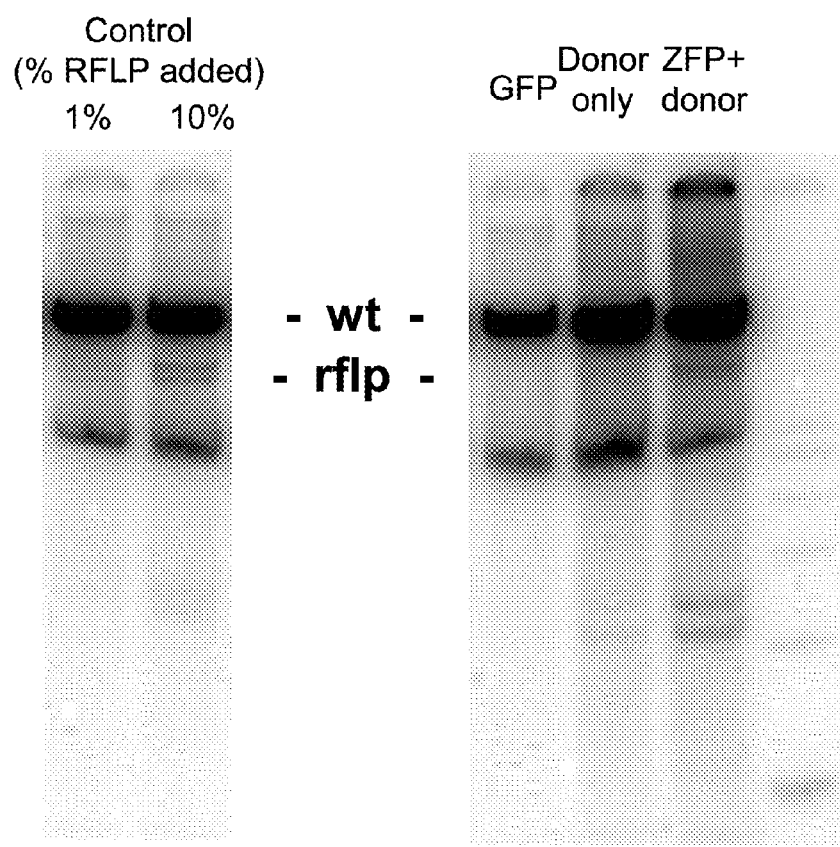
FIG. 38 shows autoradiographic images of gels used in an assay to measure targeted recombination at the human IL-2Rγ locus in CD34[+] human bone marrow cells. The left panel shows a reference standard in which the stated percentage of normal human genomic DNA (containing a MaeII site) was added to genomic DNA from Jurkat cells (lacking a MaeII site), the mixture was amplified by PCR to generate a radiolabelled amplification product, and the amplification product was digested with MaeII. "wt" identifies a band representing undigested DNA, and "rflp" identifies a band resulting from MaeII digestion.

The results are shown in FIG. 38. In addition to the major PCR product, corresponding to the 1.6 kb fragment of the IL2Rγ locus ("wt" in the right-hand panel of FIG. 38), an additional band (labeled "rflp") was observed in lanes corresponding to samples from cells that were transfected with plasmids encoding both ZFP-nucleases and the donor DNA construct. This additional band did not appear in the control lanes, consistent with the idea that ZFP-nuclease assisted gene targeting of exon 5 of the common gamma chain gene occurred in this experiment.

Although accurate quantitation of the targeting rate is complicated by the proximity of the RFLP band to the wild-type band; the targeting frequency was estimated, by comparison to the reference standard (left panel), to be between 1-5%.

Example 17: Donor-Target Homology Effects

The effect, on frequency of homologous recombination, of the degree of homology between donor DNA and the chromosomal sequence with which it recombines was examined in T18 cell line, described in Example 9. This line contains a chromosomally integrated defective eGFP gene, and the donor DNA contains sequence changes, with respect to the chromosomal gene, that correct the defect.

Accordingly, the donor sequence described in Example 10 was modified, by PCR mutagenesis, to generate a series of ~700 bp donor constructs with different degrees of non-homology to the target. All of the modified donors contained sequence changes that corrected the defect in the chromosomal eGFP gene and contained additional silent mutations (DNA mutations that do not change the sequence of the encoded protein) inserted into the coding region surrounding the cleavage site. These silent mutations were intended to prevent the binding to, and cleavage of, the donor sequence by the zinc finger-cleavage domain fusions, thereby reducing competition between the intended chromosomal target and the donor plasmid for binding by the chimeric nucleases. In addition, following homologous recombination, the ability of the chimeric nucleases to bind and re-cleave the newly-inserted chromosomal sequences (and possibly stimulating another round of recombination, or causing non-homologous end joining or other double-strand break-driven alterations of the genome) would be minimized.

Four different donor sequences were tested. Donor 1 contains 8 mismatches with respect to the chromosomal defective eGFP target sequence, Donor 2 has 10 mismatches, Donor 3 has 6 mismatches, and Donor 5 has 4 mismatches. Note that the sequence of donor 5 is identical to wild-type eGFP sequence, but contains 4 mismatches with respect to the defective chromosomal eGFP sequence in the T18 cell line. Table 22 provides the sequence of each donor between nucleotides 201-242. Nucleotides that are divergent from the sequence of the defective eGFP gene integrated into the genome of the T18 cell line are shown in bold and underlined. The corresponding sequences of the defective chromosomal eGFP gene (GFP mut) and the normal eGFP gene (GFP wt) are also shown.

TABLE 22

| Donor | Sequence | SEQ ID NO. |
|---|---|---|
| Donor 1 | CTTCAGCCGCTATCCAGACCACATGAAACAACA CGACTTCTT | 172 |
| Donor 2 | CTTCAGCCGGTATCCAGACCACATGAAACAACA TGACTTCTT | 173 |
| Donor 3 | CTTCAGCCGCTACCCAGACCACATGAAACAGCA CGACTTCTT | 174 |
| Donor 5 | CTTCAGCCGCTACCCCGACCACAT**GAAGCAGCA CGACTTCTT | 175 |
| GFP mut | CTTCAGCCGCTACCCCTAACAC--GAAGCAGCA CGACTTCTT | 176 |
| GFP wt | CTTCAGCCGCTACCCCGACCACAT**GAAGCAGCA CGACTTCTT | 177 |

The T18 cell line was transfected, as described in Example 11, with 50 ng of the 287-FokI and 296-FokI expression constructs (Example 7 and Table 12) and 500 ng of each donor construct. FACS analysis was conducted as described in Example 11.

The results, shown in Table 23, indicate that a decreasing degree of mismatch between donor and chromosomal target sequence (i.e., increased homology) results in an increased frequency of homologous recombination as assessed by restoration of GFP function.

TABLE 23[1]

| Donor | # mismatches | Percent cells with corrected eGFP gene[2] |
|---|---|---|
| Donor 2 | 10 | 0.45% |
| Donor 1 | 8 | 0.53% |
| Donor 3 | 6 | 0.89% |
| Donor 5 | 4 | 1.56% |

[1]T18 cells, containing a defective chromosomal eGFP gene, were transfected with plasmids encoding two ZFP nucleases and with donor plasmids encoding a nondefective eGFP sequence having different numbers of sequence mismatches with the chromosomal target sequence. Expression of the chromosomal eGFP gene was induced with doxycycline and FACS analysis was conducted 5 days after transfection.
[2]The number is the percent of total fluorescence exhibiting high emission at 525 nm and low emission at 570 nm (region E of the FACS trace).

The foregoing results show that levels of homologous recombination are increased by decreasing the degree of target-donor sequence divergence. Without wishing to be bound by any particular theory or to propose a particular mechanism, it is noted that greater homology between donor and target could facilitate homologous recombination by increasing the efficiency by which the cellular homologous recombination machinery recognizes the donor molecule as a suitable template. Alternatively, an increase in donor homology to the target could also lead to cleavage of the donor by the chimeric ZFP nucleases. A cleaved donor could help facilitate homologous recombination by increasing the rate of strand invasion or could aid in the recognition of the cleaved donor end as a homologous stretch of DNA during homology search by the homologous recombination machinery. Moreover, these possibilities are not mutually exclusive.

Example 18: Preparation of siRNA

To test whether decreasing the cellular levels of proteins involved in non-homologous end joining (NHEJ) facilitates targeted homologous recombination, an experiment in which levels of the Ku70 protein were decreased through siRNA inhibition was conducted. siRNA molecules targeted to the Ku70 gene were generated by transcription of Ku70 cDNA followed by cleavage of double-stranded transcript with Dicer enzyme.

Briefly, a cDNA pool generated from 293 and U2OS cells was used in five separate amplification reactions, each using a different set of amplification primers specific to the Ku70 gene, to generate five pools of cDNA fragments (pools A-E), ranging in size from 500-750 bp. Fragments in each of these five pools were then re-amplified using primers containing the bacteriophage T7 RNA polymerase promoter element, again using a different set of primers for each cDNA pool. cDNA generation and PCR reactions were performed using the Superscript Choice cDNA system and Platinum Taq High Fidelity Polymerase (both from Invitrogen, Carlsbad, Calif.), according to manufacturers protocols and recommendations.

Each of the amplified DNA pools was then transcribed in vitro with bacteriophage T7 RNA polymerase to generate five pools (A-E) of double stranded RNA (dsRNA), using the RNAMAXX in vitro transcription kit (Stratagene, San Diego, Calif.) according to the manufacturer's instructions. After precipitation with ethanol, the RNA in each of the pools was resuspended and cleaved in vitro using recombinant Dicer enzyme (Stratagene, San Diego, Calif.) according to the manufacturer's instructions. 21-23 bp siRNA products in each of the five pools were purified by a two-step method, first using a Microspin G-25 column (Amershan), followed by a Microcon YM-100 column (Amicon). Each pool of siRNA products was transiently transfected into the T7 cell line using Lipofectamone 2000®.

Western blots to assay the relative effectiveness of the siRNA pools in suppressing Ku70 expression were performed approximately 3 days post-transfection. Briefly, cells were lysed and disrupted using RIPA buffer (Santa Cruz Biotechnology), and homogenized by passing the lysates through a QIAshredder (Qiagen, Valencia, Calif.). The clarified lysates were then treated with SDS PAGE sample buffer (with β mercaptoethanol used as the reducing agent) and boiled for 5 minutes. Samples were then resolved on a 4-12% gradient NUPAGE gel and transferred onto a PVDF membrane. The upper portion of the blot was exposed to an anti-Ku70 antibody (Santa Cruz sc-5309) and the lower portion exposed to an anti-TF IIB antibody (Santa Cruz sc-225, used as an input control). The blot was then exposed to horseradish peroxidase-conjugated goat anti-mouse secondary antibody and processed for electrochemiluminescent (ECL) detection using a kit from Pierce Chemical Co. according to the manufacturer's instructions.

FIG. 39 shows representative results following transfection of two of the siRNA pools (pools D and E) into T7 cells. Transfection with 70 ng of siRNA E results in a significant decrease in Ku70 protein levels (FIG. 39, lane 3).

Example 19: Increasing the Frequency of Homologous Recombination by Inhibition of Expression of a Protein Involved in Non-Homologous End Joining Repair of a double-stranded break in genomic DNA can proceed along two different cellular pathways; homologous recombination (HR) or non-homologous end joining (NHEJ). Ku70 is a protein involved in NHEJ, which binds to the free DNA ends resulting from a double-stranded break in genomic DNA. To test whether lowering the intracellular concentration of a protein involved in NHEJ increases the frequency of HR, small interfering RNAs (siRNAs), prepared as described in Example 18, were used to inhibit expression of Ku70 mRNA, thereby lowering levels of Ku70 protein, in cells co-transfected with donor DNA and with plasmids encoding chimeric nucleases.

For these experiments, the T7 cell line (see Example 9 and FIG. 27) was used. These cells contain a chromosomally-integrated defective eGFP gene, but have been observed to exhibit lower levels of targeted homologous recombination than the T18 cell line used in Examples 11-13.

T7 cells were transfected, as described in Example 11, with either 70 or 140 ng of one of two pools of dicer product targeting Ku70 (see Example 18). Protein blot analysis was performed on extracts derived from the transfected cells to determine whether the treatment of cells with siRNA resulted in a decrease in the levels of the Ku70 protein (see previous Example). FIG. 39 shows that levels of the Ku70 protein were reduced in cells that had been treated with 70 ng of siRNA from pool E.

Separate cell samples in the same experiment were co-transfected with 70 or 140 ng of siRNA (pool D or pool E) along with 50 ng each of the 287-FokI and 296-FokI expression constructs (Example 7 and Table 12) and 500 ng of the 1.5 kbp GFP donor (Example 13), to determine whether lowering Ku70 levels increased the frequency of homologous recombination. The experimental protocol is described in Table 24. Restoration of eGFP activity, due to homologous recombination, was assayed by FACS analysis as described in Example 11.

TABLE 24

| Expt. # | Donor[1] | ZFNs[2] | siRNA[3] | % correction[4] |
|---|---|---|---|---|
| 1 | 500 ng | — | — | 0.05 |
| 2 | — | 50 ng each | — | 0.01 |
| 3 | 500 ng | 50 ng each | — | 0.79 |
| 4 | 500 ng | 50 ng each | 70 ng pool D | 0.68 |
| 5 | 500 ng | 50 ng each | 140 ng pool D | 0.59 |
| 6 | 500 ng | 50 ng each | 70 ng pool E | 1.25 |
| 7 | 500 ng | 50 ng each | 140 ng pool E | 0.92 |

[1]A plasmid containing a 1.5 kbp sequence encoding a functional eGFP protein which is homologous to the chromosomally integrated defective eGFP gene
[2]Plasmids encoding the eGFP-targeted 287 and 296 zinc finger protein/FokI fusion endonucleases
[3]See Example 18
[4]Percent of total fluorescence exhibiting high emission at 525 nm and low emission at 570 nm (region E of the FACS trace, see Example 11).

The percent correction of the defective eGFP gene in the transfected T7 cells (indicative of the frequency of targeted homologous recombination) is shown in the right-most column of Table 24. The highest frequency of targeted recombination is observed in Experiment 6, in which cells were transfected with donor DNA, plasmids encoding the two eGFP-targeted fusion nucleases and 70 ng of siRNA Pool E. Reference to Example 18 and FIG. 39 indicates that 70 ng of Pool E siRNA significantly depressed Ku70 protein levels. Thus, methods that reduce cellular levels of proteins involved in NHEJ can be used as a means of facilitating homologous recombination.

Example 20: Zinc Finger-FokI Fusion Nucleases Targeted to the Human β-Globin Gene A number of four-finger zinc finger DNA binding domains, targeted to the human β-globin gene, were designed and plasmids encoding each zinc finger domain, fused to a FokI cleavage half-domain, were constructed. Each zinc finger domain contained four zinc fingers and recognized a 12 bp target site in the region of the human β-globin gene encoding the mutation responsible for Sickle Cell Anemia. The binding affinity of each of these proteins to its target sequence was assessed, and four proteins exhibiting strong binding (sca-r29b, sca-36a, sca-36b, and sca-36c) were used for construction of FokI fusion endonucleases.

The target sites of the ZFP DNA binding domains, aligned with the sequence of the human β-globin gene, are shown below. The translational start codon (ATG) is in bold and underlined, as is the A-T substitution causing Sickle Cell Anemia.

sca-36a
(SEQ ID NO: 178)
GAAGTCTGCCGT sca-36b
(SEQ ID NO: 179)
GAAGTCtGCCGTT sca-36c
(SEQ ID NO: 180)
GAAGTCtGCCGTT

CAAACAGACACCATGGTGCATCTGACTCCTGT GGAGAAGTCTGCCGTTA CTG (SEQ ID NO: 181)
GTTTGTCTGTGGTACCACGTAGACTGAGGACACCTCTTCAGACGGCAAT GAC sca-r29b
(SEQ ID NO: 182)
ACGTAGaCTGAGG Amino acid sequences of the recognition regions of the zinc fingers in these four proteins are shown in Table 25. The complete amino acid sequences of these zinc finger domains are shown in FIG. 40. The sca-36a domain recognizes a target site having 12 contiguous nucleotides (shown in upper case above), while the other three domain recognize a thirteen nucleotide sequence consisting of two six-nucleotide target sites (shown in upper case) separated by a single nucleotide (shown in lower case). Accordingly, the sca-r29b, sca-36b and sca-36c domains contain a non-canonical inter-finger linker having the amino acid sequence TGGGGSQKP (SEQ ID NO:183) between the second and the third of their four fingers.

TABLE 25

| ZFP | F1 | F2 | F3 | F4 |
|---|---|---|---|---|
| sca-r29b | QSGDLTR (SEQ ID NO: 184) | TSANLSR (SEQ ID NO: 185) | DRSALSR (SEQ ID NO: 186) | QSGHLSR (SEQ ID NO: 187) |
| sca-36a | RSQTRKT (SEQ ID NO: 188) | QKRNRTK (SEQ ID NO: 189) | DRSALSR (SEQ ID NO: 190) | QSGNLAR (SEQ ID NO: 191) |
| sca-36b | TSGSLSR (SEQ ID NO: 192) | DRSDLSR (SEQ ID NO: 193) | DRSALSR (SEQ ID NO: 194) | QSGNLAR (SEQ ID NO: 195) |
| sca-36c | TSSSLSR (SEQ ID NO: 196) | DRSDLSR (SEQ ID NO: 197) | DRSALSR (SEQ ID NO: 198) | QSGNLAR (SEQ ID NO: 199) |

Example 21: In Vitro Cleavage of a DNA Target Sequence by β-Globin-Targeted ZFP/FokI Fusion Endonucleases Fusion proteins containing a FokI cleavage half-domain and one the four ZFP DNA binding domains described in the previous example were tested for their ability to cleave DNA in vitro with the predicted sequence specificity. These ZFP domains were cloned into the pcDNA3.1 expression vector via KpnI and BamHI sites and fused in-frame to the FokI cleavage domain via a 4 amino acid ZC linker, as described above. A DNA fragment containing 700 bp of the human β-globin gene was cloned from genomic DNA obtained from K562 cells. The isolation and sequence of this fragment was described in Example 3, supra.

To produce fusion endonucleases (ZFNs) for the in vitro assay, circular plasmids encoding FokI fusions to sca-r29b, sca-36a, sca-36b, and sca-36c protein were incubated in an in vitro transcription/translation system. See Example 4. A total of 2 ul of the TNT reaction (2 ul of a single reaction when a single protein was being assayed or 1 ul of each reaction when a pair of proteins was being assayed) was added to 13 ul of the cleavage buffer mix and 3 ul of labeled probe (~1 ng/ul). The probe was end-labeled with $^{32}$P using polynucleotide kinase. This reaction was incubated for 1 hour at room temperature to allow binding of the ZFNs. Cleavage was stimulated by the addition of 8 ul of 8 mM MgCl$_2$, diluted in cleavage buffer, to a final concentration of approximately 2.5 mM. The cleavage reaction was incubated for 1 hour at 37° C. and stopped by the addition of 11 ul of phenol/chloroform. The DNA was isolated by phenol/chloroform extraction and analyzed by gel electrophoresis, as described in Example 4. As a control, 3 ul of probe was analyzed on the gel to mark the migration of uncut DNA (labeled "U" in FIG. 41).

The results are shown in FIG. 41. Incubation of the target DNA with any single zinc finger/FokI fusion resulted in no change in size of the template DNA. However, the combination of the sca-r29b nuclease with either of the sca-36b or sca-36c nucleases resulted in cleavage of the target DNA, as evidenced by the presence of two shorter DNA fragments (rightmost two lanes of FIG. 41).

Example 22: ZFP/FokI Fusion Endonucleases, Targeted to the β-Globin Gene, Tested in a Chromosomal GFP Reporter System A DNA fragment containing the human β-globin gene sequence targeted by the ZFNs described in Example 20 was synthesized and cloned into a SpeI site in an eGFP reporter gene thereby, disrupting eGFP expression. The fragment contained the following sequence, in which the nucleotide responsible for the sickle cell mutation is in bold and underlined):

(SEQ ID NO: 200)
CTAGACACCATGGTGCATCTGACTCCTGTGGAGAAGTCTGCCGTTACT

GCCCTAG

This disrupted eGFP gene containing inserted β-globin sequences was cloned into pcDNA4/TO (Invitrogen, Carlsbad, Calif.) using the HindIII and NotI sites, and the resulting vector was transfected into HEK293 TRex cells (Invitrogen). Individual stable clones were isolated and grown up, and the clones were tested for targeted homologous recombination by transfecting each of the sca-36 proteins (sca-36a, sca-36b, sca-36c) paired with sca-29b (See Example 20 and Table 25 for sequences and binding sites of these chimeric nucleases). Cells were transfected with 50 ng of plasmid encoding each of the ZFNs and with 500 ng of the 1.5-kb GFP Donor (Example 13). Five days after transfection, cells were tested for homologous recombination at the inserted defective eGFP locus. Initially, cells were examined by fluorescence microscopy for eGFP function. Cells exhibiting fluorescence were then analyzed quantitatively using a FACS assay for eGFP fluorescence, as described in Example 11.

The results showed that all cell lines transfected with sca-29b and sca-36a were negative for eGFP function, when assayed by fluorescence microscopy. Some of the lines transfected with sca-29b paired with either sca-36b or sca-36c were positive for eGFP expression, when assayed by fluorescence microscopy, and were therefore further analyzed by FACS analysis. The results of FACS analysis of two of these lines are shown in Table 26, and indicate that zinc finger nucleases targeted to β-globin sequences are capable of catalyzing sequence-specific double-stranded DNA cleavage to facilitate homologous recombination in living cells.

TABLE 26

| | DNA transfected: | | | | |
|---|---|---|---|---|---|
| Cell line | sca-29b | sca-36a | sca-36b | sca-36c | % corr.[1] |
| #20 | + | + | | | 0 |
| | + | | + | | 0.08 |
| | + | | | + | 0.07 |
| #40 | + | + | | | 0 |
| | + | | + | | 0.18 |
| | + | | | + | 0.12 |

[1]Percent of total fluorescence exhibiting high emission at 525 nm and low emission at 570 nm (region E of the FACS trace, see Example 11).

Example 23: Effect of Transcription Level on Targeted Homologous Recombination Since transcription of a chromosomal DNA sequence involves alterations in its chromatin structure (generally to make the transcribed sequences more accessible), it is possible that an actively transcribed gene might be a more favorable substrate for targeted homologous recombination. This idea was tested using the T18 cell line (Example 9) which contains chromosomal sequences encoding a defective eGFP gene whose transcription is under the control of a doxycycline-inducible promoter.

Separate samples of T18 cells were transfected with plasmids encoding the eGFP-targeted 287 and 296 zinc finger/FokI fusion proteins (Example 7) and a 1.5 kbp donor DNA molecule containing sequences that correct the defect in the chromosomal eGFP gene (Example 9). Five hours after transfection, transfected cells were treated with different concentrations of doxycycline, then eGFP mRNA levels were measured 48 hours after addition of doxycycline. eGFP fluorescence at 520 nm (indicative of targeted recombination of the donor sequence into the chromosome to replace the inserted β-globin sequences) was measured by FACS at 4 days after transfection.

The results are shown in FIG. 42. Increasing steady-state levels of eGFP mRNA normalized to GAPDH mRNA (equivalent, to a first approximation, to the rate of transcription of the defective chromosomal eGFP gene) are indicated by the bars. The number above each bar indicate the percent of cells exhibiting eGFP fluorescence. The results show that increasing transcription rate of the target gene is accompanied by higher frequencies of targeted recombination. This suggests that targeted activation of transcription (as disclosed, e.g. in co-owned U.S. Pat. Nos. 6,534,261 and 6,607,882) can be used, in conjunction with targeted DNA cleavage, to stimulate targeted homologous recombination in cells.

Example 24: Generation of a Cell Line Containing a Mutation in the IL-2Rγ Gene

K562 cells were transfected with plasmids encoding the 5-8GL0 and the 5-9DL0 zinc finger nucleases (ZFNs) (see Example 14; Table 17) and with a 1.5 kbp DraI donor construct. The DraI donor is comprised of a sequence with homology to the region encoding the 5$^{th}$ exon of the IL2Rγ gene, but inserts an extra base between the ZFN-binding sites to create a frameshift and generate a DraI site.

24 hours post-transfection, cells were treated with 0.2 uM vinblastine (final concentration) for 30 hours. Cells were washed three times with PBS and re-plated in medium. Cells were allowed to recover for 3 days and an aliquot of cells were removed to perform a PCR-based RFLP assay, similar to that described in Example 14, testing for the presence of a DraI site. It was determined the gene correction frequency within the population was approximately 4%.

Cells were allowed to recover for an additional 2 days and 1600 individual cells were plated into 40×96-well plates in 100 ul of medium.

The cells are grown for about 3 weeks, and cells homozygous for the DraI mutant phenotype are isolated. The cells are tested for genome modification (by testing for the presence of a DraI site in exon 5 of the IL-2Rγ gene) and for levels of IL-2Rγ mRNA (by real-time PCR) and protein (by Western blotting) to determine the effect of the mutation on gene expression. Cells are tested for function by FACS analysis.

Cells containing the DraI frameshift mutation in the IL-2Rγ gene are transfected with plasmids encoding the 5-8GL0 and 5-9DL0 fusion proteins and a 1.5 kb BsrBI donor construct (Example 14) to replace the DraI frameshift mutation with a sequence encoding a functional protein. Levels of homologous recombination greater than 1% are obtained in these cells, as measured by assaying for the presence of a BsrBI site as described in Example 14. Recovery of gene function is demonstrated by measuring mRNA and protein levels and by FACS analysis.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

The invention claimed is:

1. An isolated cell comprising
   (i) an exogenous non-naturally occurring nuclease comprising
      first and second heterodimerizing FokI cleavage domains, wherein one of the first and second cleavage domains comprises a substitution mutation of amino acid 490 of the wild-type dimerization interface, and
      a zinc finger DNA-binding protein that is heterologous to the first and second cleavage domains, wherein the zinc finger DNA-binding protein binds to a sequence in an HLA gene, and
   (ii) an inactivated endogenous HLA gene, wherein the endogenous HLA gene comprises on or more nucleotide insertions, deletions or substitutions such that it is inactivated.

2. The cell of claim 1, wherein the cell is a stem cell.

3. The cell of claim 1, wherein the cell further comprises a transgene.

4. A method of grafting a cell into a host, the method comprising, administering a cell according to claim 1 to the host.

5. The method of claim 4, where the cell further comprises a transgene.

6. The method of claim 4, wherein the inactivated HLA gene encodes a Major Histocompatibility Complex (MHC) class 1 protein.

7. The method of claim 6, wherein the inactivated HLA gene encodes an MHC β subunit gene (β2 microglobulin).

8. The method of claim 6, wherein the cell is a stem cell.

* * * * *